(12) United States Patent
    Clark

(10) Patent No.: US 11,751,894 B2
(45) Date of Patent: *Sep. 12, 2023

(54) OBSTRUCTION RETRIEVAL DEVICES

(71) Applicant: Timothy William Ingraham Clark, Philadelphia, PA (US)

(72) Inventor: Timothy William Ingraham Clark, Philadelphia, PA (US)

(*) Notice: Subject to any disclaimer, the term of this patent is extended or adjusted under 35 U.S.C. 154(b) by 166 days.

This patent is subject to a terminal disclaimer.

(21) Appl. No.: 17/107,038

(22) Filed: Nov. 30, 2020

(65) Prior Publication Data
    US 2021/0077135 A1    Mar. 18, 2021

Related U.S. Application Data

(63) Continuation of application No. 16/678,460, filed on Nov. 8, 2019, now Pat. No. 10,881,420, which is a
(Continued)

(51) Int. Cl.
    *A61B 17/221* (2006.01)
    *A61B 17/00* (2006.01)

(52) U.S. Cl.
    CPC .. *A61B 17/221* (2013.01); *A61B 2017/00526* (2013.01); *A61B 2017/00867* (2013.01);
    (Continued)

(58) Field of Classification Search
    CPC .......... A61B 17/221; A61B 17/320725; A61B 17/32075; A61B 2017/00526;
    (Continued)

(56) References Cited

U.S. PATENT DOCUMENTS 4,425,908 A    1/1984 Simon
5,376,100 A    12/1994 Lefebvre
(Continued)

OTHER PUBLICATIONS

International Search Report and Written Opinion received in International Application No. PCT/US2020/025361, dated Jun. 9, 2020 (10 pages).
(Continued)

*Primary Examiner* — Mohamed G Gabr
(74) *Attorney, Agent, or Firm* — Edell, Shapiro & Finnan, LLC

(57) ABSTRACT

Retrieval assemblies configured to capture an obstruction located in a bodily duct of a patient and associated methods of manufacture are provided. According to one implementation a retrieval assembly is provided that includes a distal collar fixed stationary on an elongate wire, a proximal collar slideable along a portion of the length of the elongate wire, and a plurality of shape memory elongate capturing elements that each has a proximal end coupled to the proximal collar and a distal end coupled to the distal collar. The retrieval device is configured to automatically transition from a radially constrained state to an expanded rest state with the proximal collar located nearer the distal collar when in the expanded rest state. As the retrieval device transitions from the radially constrained state to the expanded rest state, proximal portions of the capturing elements invert around the proximal collar.

11 Claims, 47 Drawing Sheets

Related U.S. Application Data continuation of application No. 16/379,080, filed on Apr. 9, 2019, now Pat. No. 10,555,745.

(52) U.S. Cl.
 CPC ............... *A61B 2017/2215* (2013.01); *A61B 2017/2217* (2013.01); *A61F 2210/0014* (2013.01)

(58) Field of Classification Search
 CPC .. A61B 2017/00867; A61B 2017/2212; A61B 2017/2215; A61B 2017/2217; A61F 2210/0014
 See application file for complete search history.

(56) References Cited

U.S. PATENT DOCUMENTS

| | | | |
|---|---|---|---|
| 6,458,139 B1 | 10/2002 | Palmer et al. | |
| 6,695,813 B1* | 2/2004 | Boyle | A61F 2/01 606/198 |
| 8,777,976 B2 | 7/2014 | Brady et al. | |
| 9,427,300 B2 | 8/2016 | Angel et al. | |
| 9,777,976 B2 | 10/2017 | Moskovitch | |
| 9,827,084 B2 | 11/2017 | Bonnette et al. | |
| 10,555,745 B1* | 2/2020 | Clark | A61B 17/221 |
| 10,588,649 B2 | 3/2020 | Brady et al. | |
| 2002/0062135 A1* | 5/2002 | Mazzocchi | A61B 17/12109 606/200 |
| 2002/0138094 A1* | 9/2002 | Borillo | A61F 2/013 606/200 |
| 2004/0093012 A1* | 5/2004 | Cully | B23P 11/00 606/200 |
| 2004/0153117 A1 | 8/2004 | Clubb et al. | |
| 2006/0030877 A1 | 2/2006 | Martinez et al. | |
| 2009/0209987 A1 | 8/2009 | Mathews et al. | |
| 2010/0268264 A1* | 10/2010 | Bonnette | A61F 2/0108 606/200 |
| 2011/0125181 A1 | 5/2011 | Brady et al. | |
| 2012/0239064 A1 | 9/2012 | Cartier et al. | |
| 2017/0265982 A1 | 9/2017 | Cully et al. | |

OTHER PUBLICATIONS

Japanese Office Action with English translation, Application No. 2021-560637, dated Oct. 14, 2022, 15 pages.
European Search Report, EP20787544, dated Dec. 12, 2022, 9 pages.

* cited by examiner

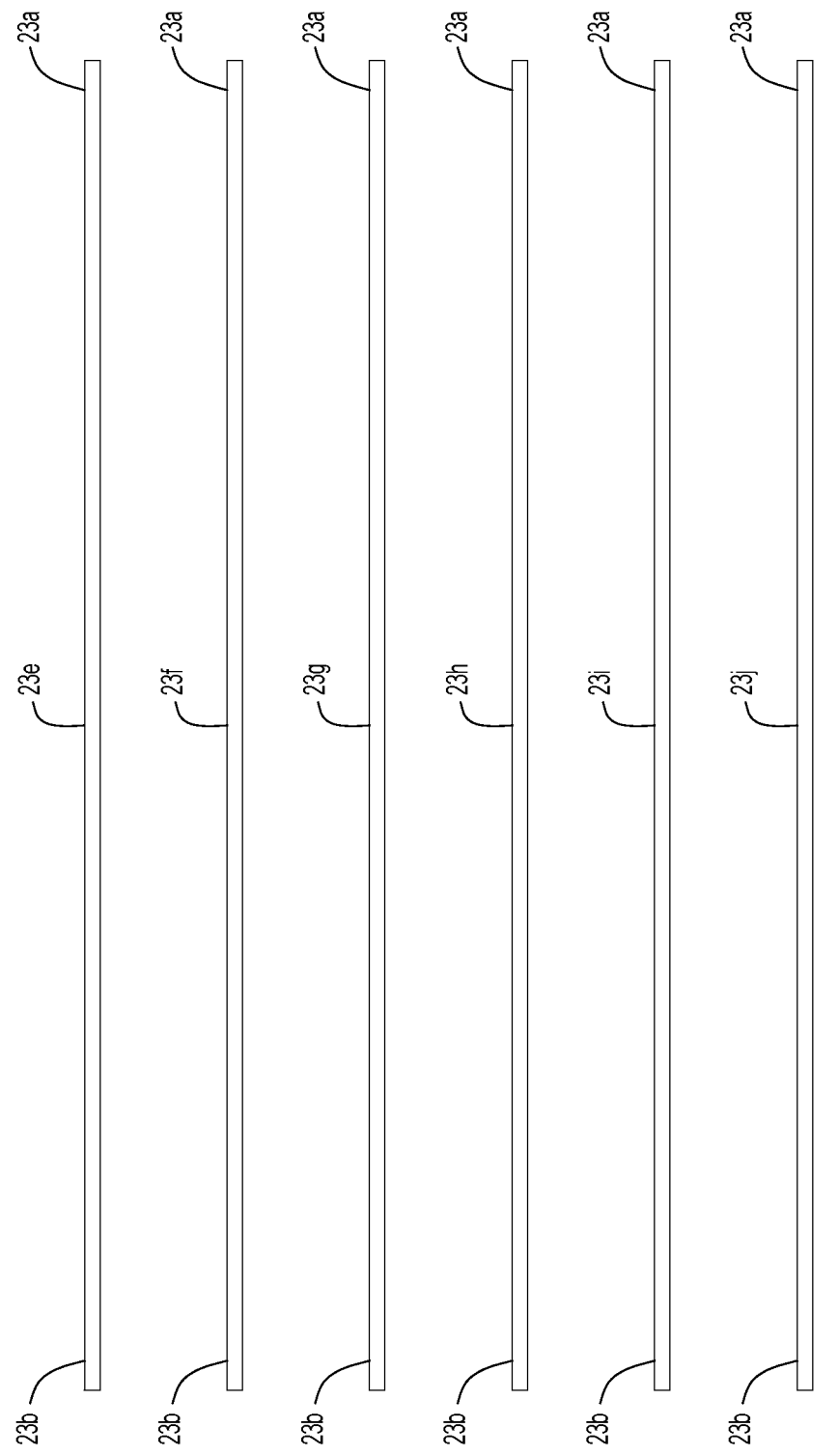

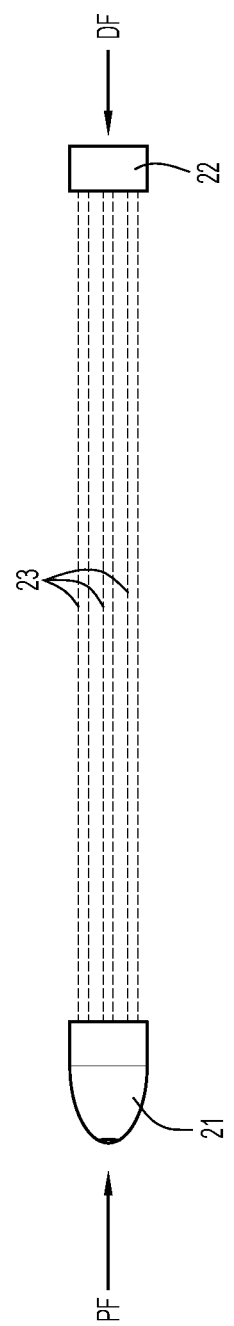

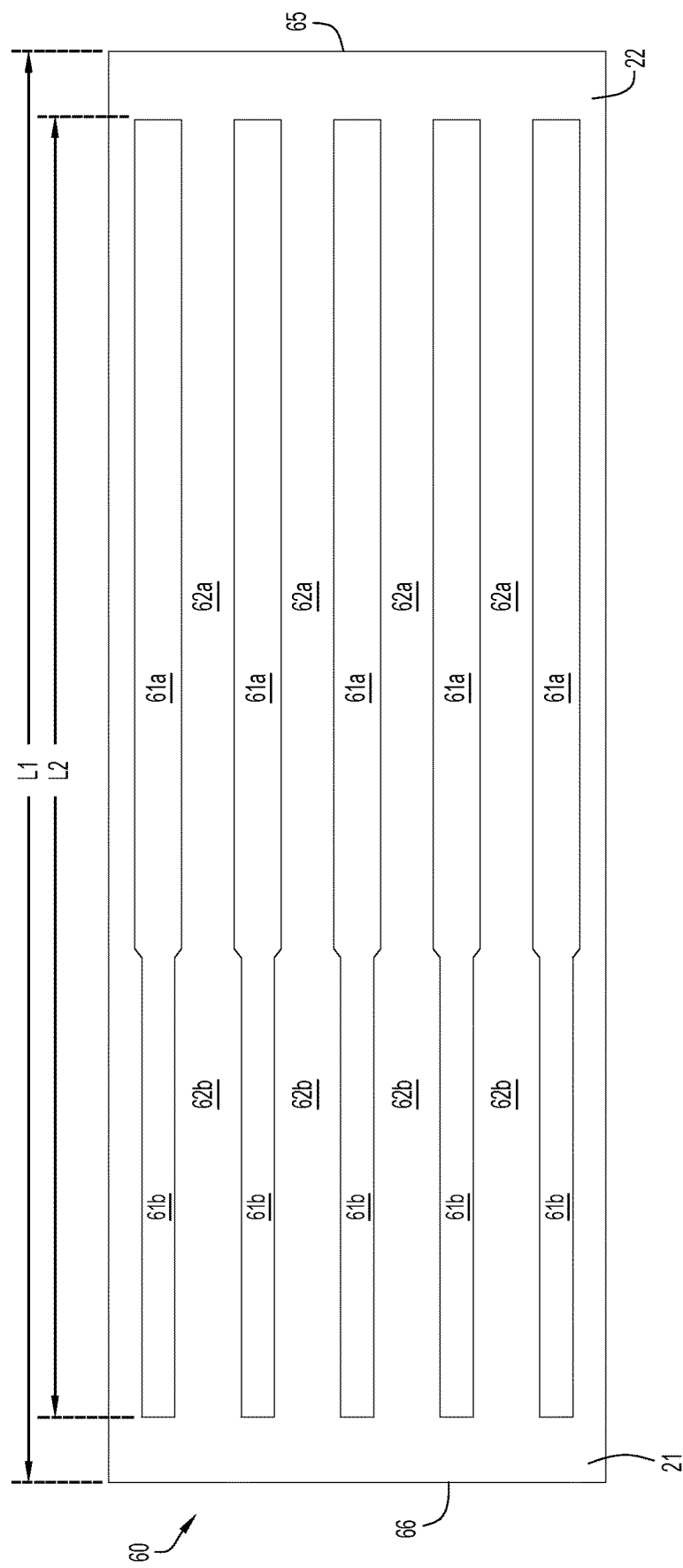

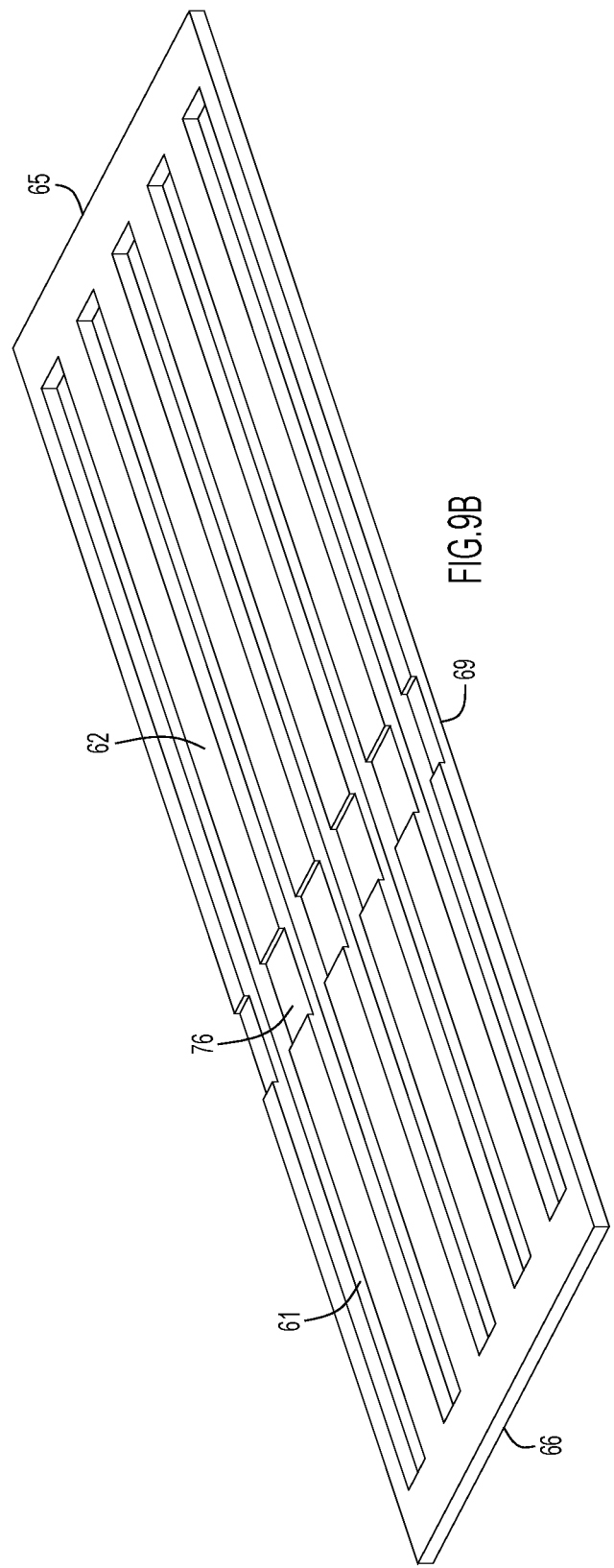
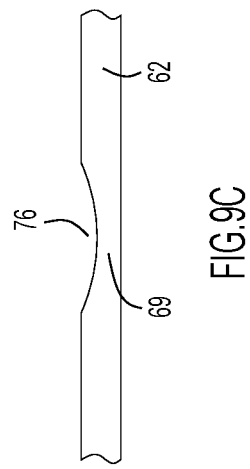
FIG.9B
FIG.9C

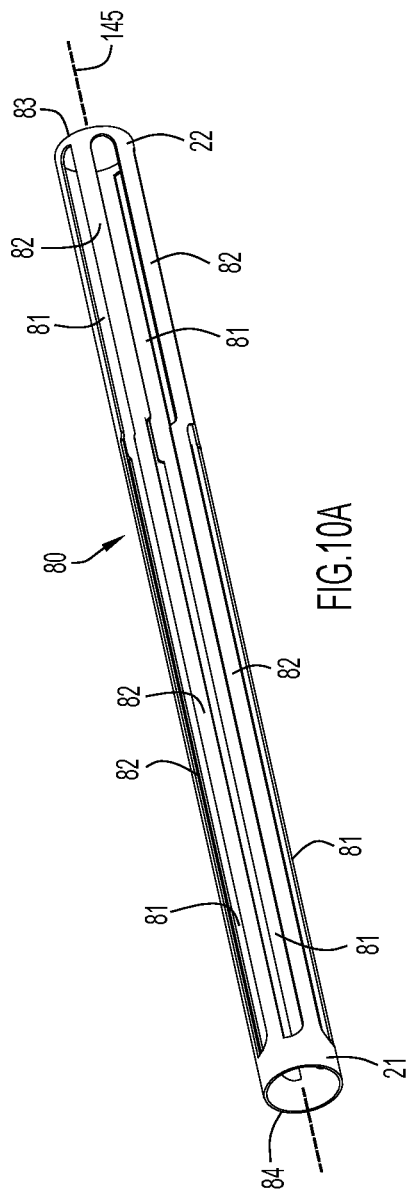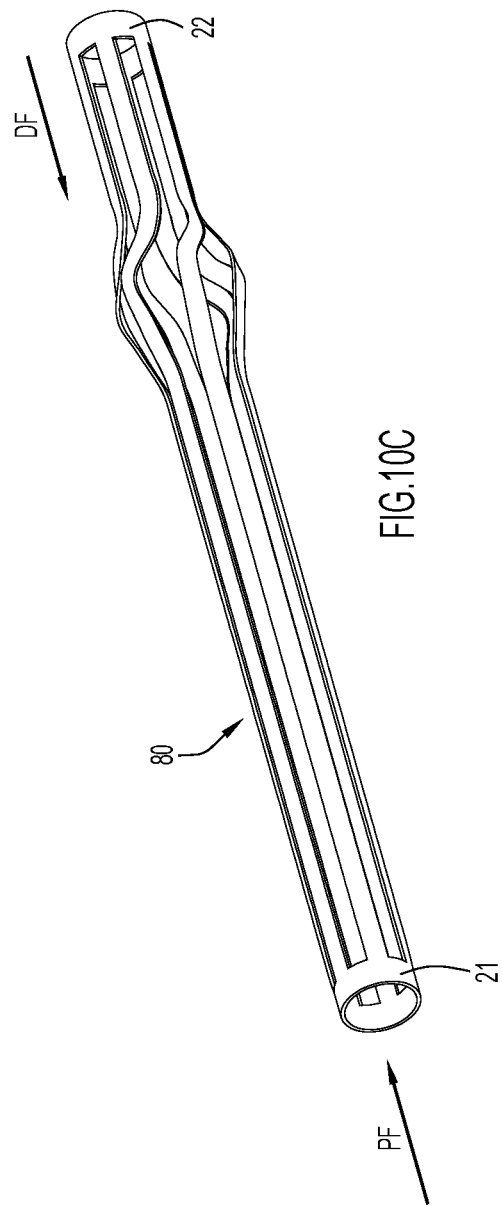

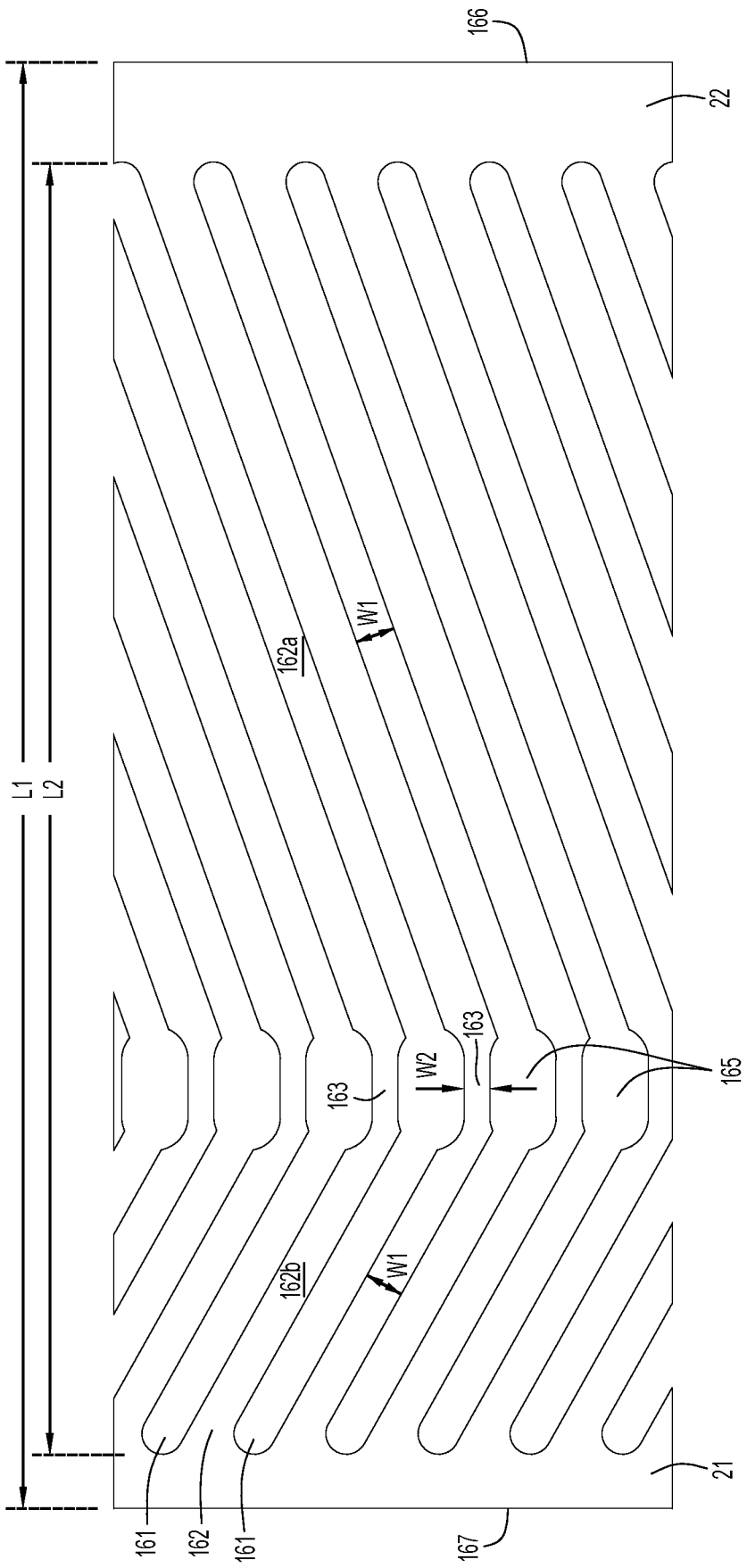

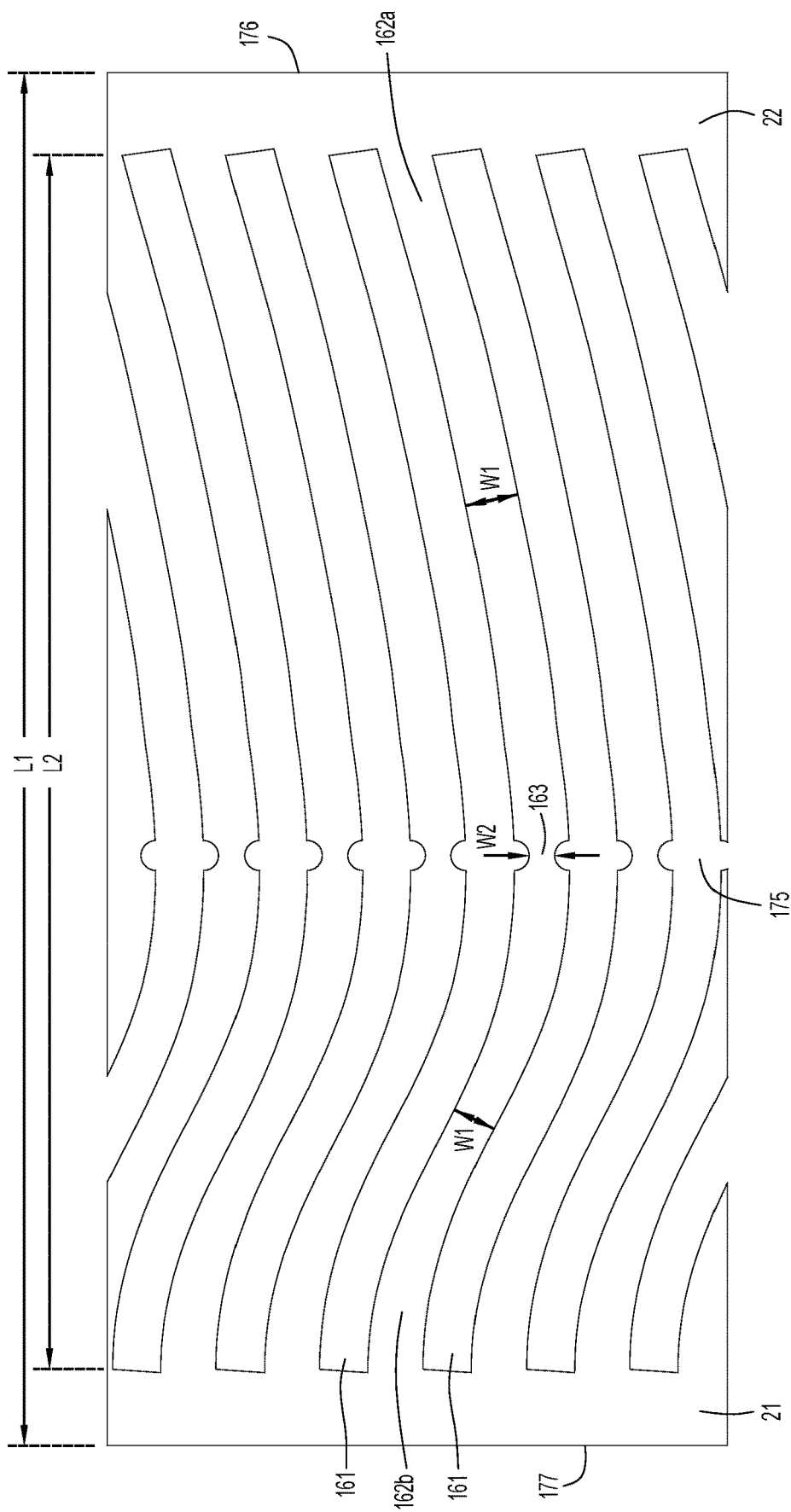

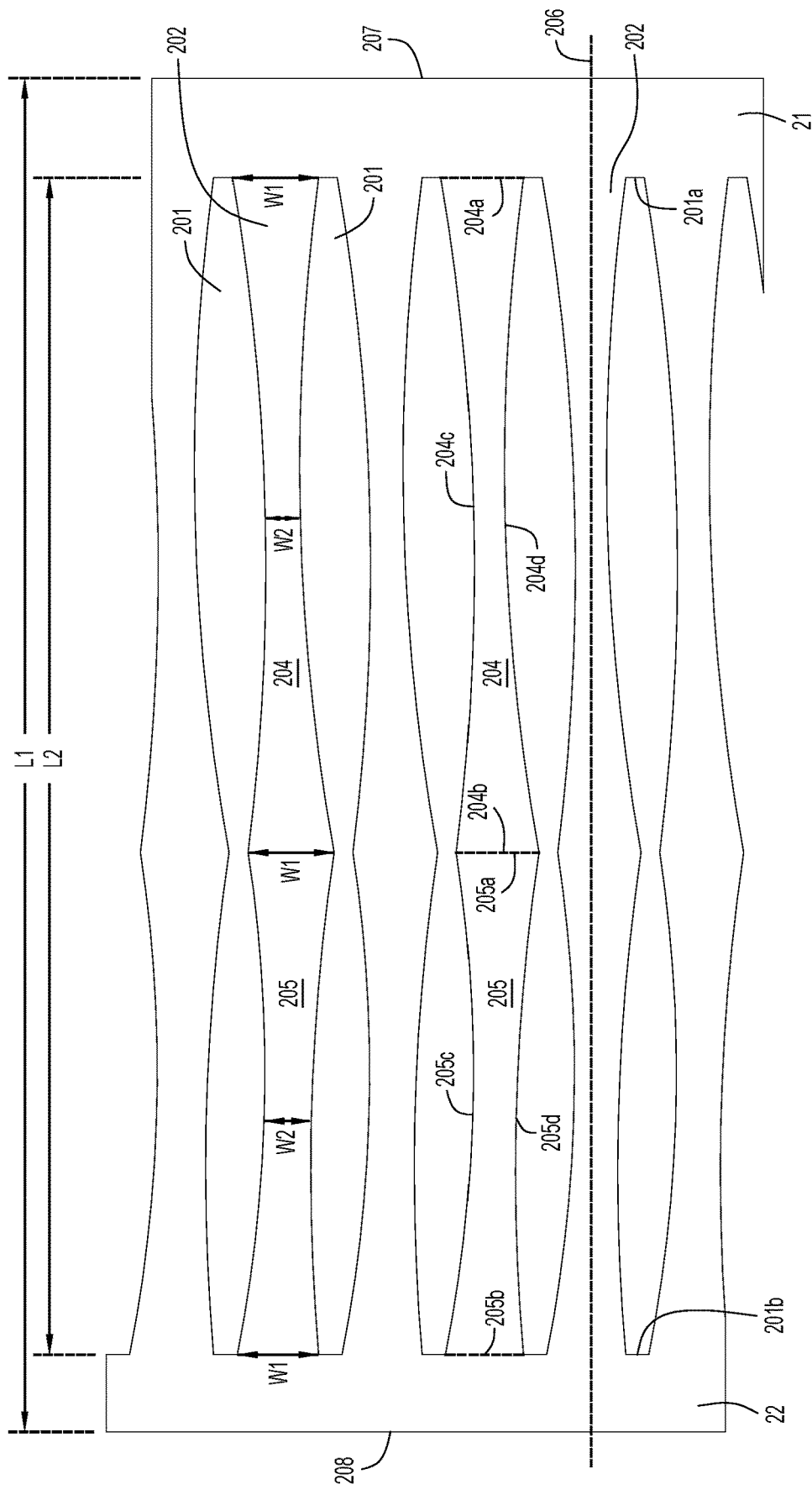

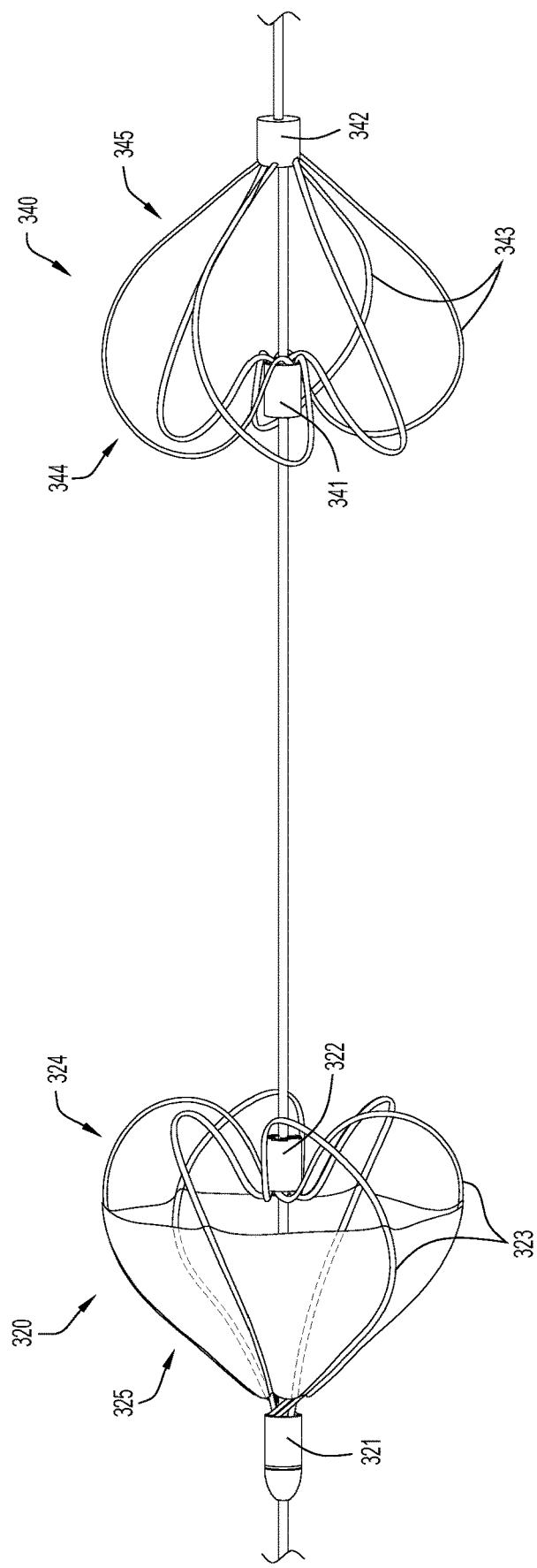

OBSTRUCTION RETRIEVAL DEVICES

CROSS-REFERENCE TO RELATED APPLICATIONS

This application is a continuation of U.S. patent application Ser. No. 16/678,460, filed Nov. 8, 2019, which is a continuation of U.S. patent application Ser. No. 16/379,080 filed Apr. 9, 2019, which is now U.S. Pat. No. 10,555,745, issued on Feb. 11, 2020.

FIELD

The present invention relates to devices, assemblies and methods for removing obstructions from a bodily duct of a patient, such as, for example, removing clots located within the vasculature of a patient.

BACKGROUND

Existing clot retrieval devices are based on the concept of passing a guidewire through or near the center of the thrombus until the guidewire is beyond the thrombus, passing a delivery catheter over the guidewire across the thrombus and then exchanging the guidewire for a retriever. The delivery catheter is thereby withdrawn, exposing the retriever to the clot to enable capture after expansion of the retriever. This is followed by withdrawal of the clot-containing retriever device into an aspiration catheter positioned proximal to the clot of sufficient diameter to enable retrieval of the device with retention of the clot. One such retrieval device is the Solitaire™ revascularization device.

Most clot capturing elements of current retrievers are made of Nitinol and passively expand into and through the clot using the intrinsic radial force of the device prior to retraction of the device to remove the thrombus. This radial force is through thermally-induced, martensitic transformation of the Nitinol elements of the device by a predetermined shape change in the geometry of the Nitinol. By necessity, this expansion produces shearing and fracturing of the thrombus, since the clot capturing elements cannot expand through the clot to contact the vessel wall without producing linear defects within the clot. This clot shearing and fracturing can in turn increase the risk of distal embolization.

An estimated 700,000 patients in the U.S. and 950,000 in Europe suffer ischemic strokes each year, the majority of which are large vessel occlusions (LVOs). Some of the pivotal randomized prospective clinical trials to date have established the superiority of radially expandable retriever devices over drug therapy alone for LVOs of the anterior cerebral circulation. These clinical trials include: MR CLEAN, with published analysis appearing in the New England Journal of Medicine 2015; SWIFT PRIME, with published analysis appearing in the New England Journal of Medicine 2015; ESCAPE, with published analysis appearing in the New England Journal of Medicine 2015; EXTEND IA, with published analysis appearing in the New England Journal of Medicine 2015; REVASCAT, with published analysis appearing in the New England Journal of Medicine 2015 and THRACE, with published analysis appearing in Lancet Neurology 2016.

The published analyses of these trials have not emphasized the number of new ischemic strokes in the interventional arms of these studies compared to standard medical therapy. These new strokes are attributed to distal embolization, vessel spasm or dissection. In the MR CLEAN study, 5.6% (13 of 233) of patients in the retriever arm had clinical signs of a new ischemic stroke in a different vascular territory compared to 0.4% (1 of 267) in the control group, representing a 14-fold relative risk. In the REVASCAT study, 4.9% of patients had distal embolization into a new vascular territory compared to none in the control group, and 12.7% had local arterial complications attributed to passage of the retriever device (3.9% dissection, 4.9% perforation, and 3.9% vasospasm requiring treatment) compared to none in the control group. In the THRACE study, 6% had distal embolization in a new territory, and 26% experienced vasospasm, dissection or perforation. None of these events occurred in the control group.

The number of additional passes (withdrawal of the retriever across the initial clot-containing segment of the vessel) has also been underemphasized in the clinical trials of these devices to date. Each pass of a retriever requires manipulation and advancement of a catheter and guidewire across the segment of the thrombus-containing artery to enable repeat delivery/deployment of the retriever, thereby creating potential vessel injury in the form of vasospasm, dissection or perforation. In a recent study, as many as 5 separate retriever passes were required for intended thrombus removal (REVIVE 2018) with a mean of 2.2 passes. The Instructions for Use (IFU) for the Solitaire™ thrombectomy device (sold by Medtronic) instructs physicians to perform no more than three recovery attempts in the same vessel. The IFU for the Trevo™ thrombectomy device (sold by Stryker) instructs physicians to exercise caution when withdrawing the device through an area or arterial vasospasm. The 3D Revascularization device (sold by Penumbra) enables up to 5 passes of the retriever device, each of which requires re-crossing of the target vessel (e.g. M1 segment of the middle cerebral artery) with a catheter and guidewire.

SUMMARY

Obstruction retrieval devices, assemblies and methods are disclosed herein along with methods of manufacturing retrieval devices. Although the example implementations disclosed herein are directed to the removal of blood clots located within an artery of a patient, it is appreciated that the devices, assemblies and methods are applicable to the retrieval of other types of obstructions located in other bodily ducts of the patient.

According to some implementations a clot retrieval assembly is provided that includes an elongate wire and a retrieval device mounted on the elongate wire. According to some implementations the retrieval device includes a distal collar fixed stationary on the elongate wire and a proximal collar that is slideable along a portion of the length of the elongate wire. Extending between the proximal and distal collars are a plurality of shape memory elongate clot capturing elements that each has a proximal end coupled to the proximal collar and a distal end coupled to the distal collar. According to some implementations the retrieval device is configured to assume a radially constrained state, an expanded rest state and an expanded stressed state. When the retrieval device is in the radially constrained state the proximal collar is located at a first axial position on the elongate wire proximal to the distal collar and is spaced apart from the distal collar by a first distance. When the retrieval device is in the expanded rest state the proximal collar is located at a second axial position on the elongate wire proximal to the distal collar and is spaced apart from the distal collar by a second distance that is less than the first distance. When the retrieval device is in the expanded stressed state the proximal collar is located at a third axial position on the elongate wire proximal to the distal collar and is spaced apart from the distal collar by a third distance that is less than the second distance.

When the retrieval device is in the radially constrained state and the constraining force is removed, the shape memory characteristic of the elongate clot capturing elements causes the retrieval device to transition from the radially constrained state to the expanded rest state. The retrieval device is configured such that during its transition from the radially constrained state to the expanded rest state an inversion of the elongate clot capturing elements occurs in a proximal section of the retrieval device that results in the elongate clot capturing elements assuming arched configurations. During the inversion the proximal collar transitions to the second axial position on the elongate wire and after the inversion is at least partially surrounded by the arched clot capturing elements.

Upon a distal force being applied to the proximal side of the retrieval device, or applied to a proximal end of the proximal collar, the retrieval device transitions from the expanded rest state to the expanded stressed state. The shortening of the distance between the proximal and distal collars urges the arched clot capturing elements to expand radially outward and/or causes the stiffness of the elongate clot capturing elements that form the arches to increase as a result of a more pronounced bending of the shape memory elongate clot capturing elements. In either event, the retrieval device's clot capturing capability is enhanced by an increase in radial force being applied by the arched clot capturing elements and/or by an increased rigidity of the arched clot capturing elements.

According to some implementations the shape memory elongate clot capturing elements are independent elements that are fixed at their proximal ends to the proximal collar and at their distal ends to the distal collar. According to other implementations the proximal collar, distal collar and shape memory elongate clot capturing elements are integrally formed (i.e. made from a single piece of material).

According to some implementations the retrieval device is delivered to the site of the clot in its radially constrained state inside a delivery catheter. According to some implementations the retrieval device is deployed inside the vasculature of the patient at a location distal to the clot. During deployment the proximal end portions of the clot capturing elements invert around the proximal collar as explained above. After deployment of the retrieval device inside the artery of the patient, the elongate wire is withdrawn proximally by the clinician to cause the proximal end portion of the retrieval device to engage the clot. This results in a distal force being applied to the proximal side of the retrieval device and causes the proximal collar to be moved distally closer to the distal collar. As a result of the proximal collar's ability to slide distally on the elongate wire after the retrieval device has been deployed, the radial force exerted by the arched clot capturing elements can vary during the retrieval process. This variable radial force characteristic enhances the clot capturing capability of the retrieval device as explained above.

These and other implementations along with their advantages and features will become evident in view of the drawings and the detailed description.

BRIEF DESCRIPTION OF THE DRAWINGS

FIG. 6 illustrates a plurality of independent clot capturing elements having proximal and distal ends that are respectively configured to reside in the radially dispersed openings of the proximal and distal collars shown in FIGS. 5B and 4A.

FIG. 7A show the components of FIGS. 4B, 5D and 6 in a first assembled state.

FIG. 8E shows the tubular member like that of FIG. 8B with the proximal and distal end sections of the clot capturing elements having different widths.

FIG. 9B illustrates a flattened view of the tube of FIG. 9A after the formation of slots therein.

FIG. 9C shows a cross-sectional view of a clot capturing element with a curved recess formed therein.

FIG. 10A illustrates a tubular member from which a retrieval device is unitarily made according to another implementation.

FIG. 10C shows the tubular member of FIG. 10A upon there being an axial force applied to one or both of the proximal and distal collars to cause the proximal end portion of the tubular member to invert.

FIG. 16B shows the tubular member of FIG. 16A cut along its axial length and laid flat on a surface.

FIG. 17B shows the tubular member of FIG. 17A cut along its axial length and laid flat on a surface.

FIG. 18B shows the tubular member of FIG. 18A cut along its axial length and laid flat on a surface.

FIG. 20B illustrates an enlarged view of the proximal and distal retrieval devices shown in FIG. 20A.

DETAILED DESCRIPTION

Figure 1A:
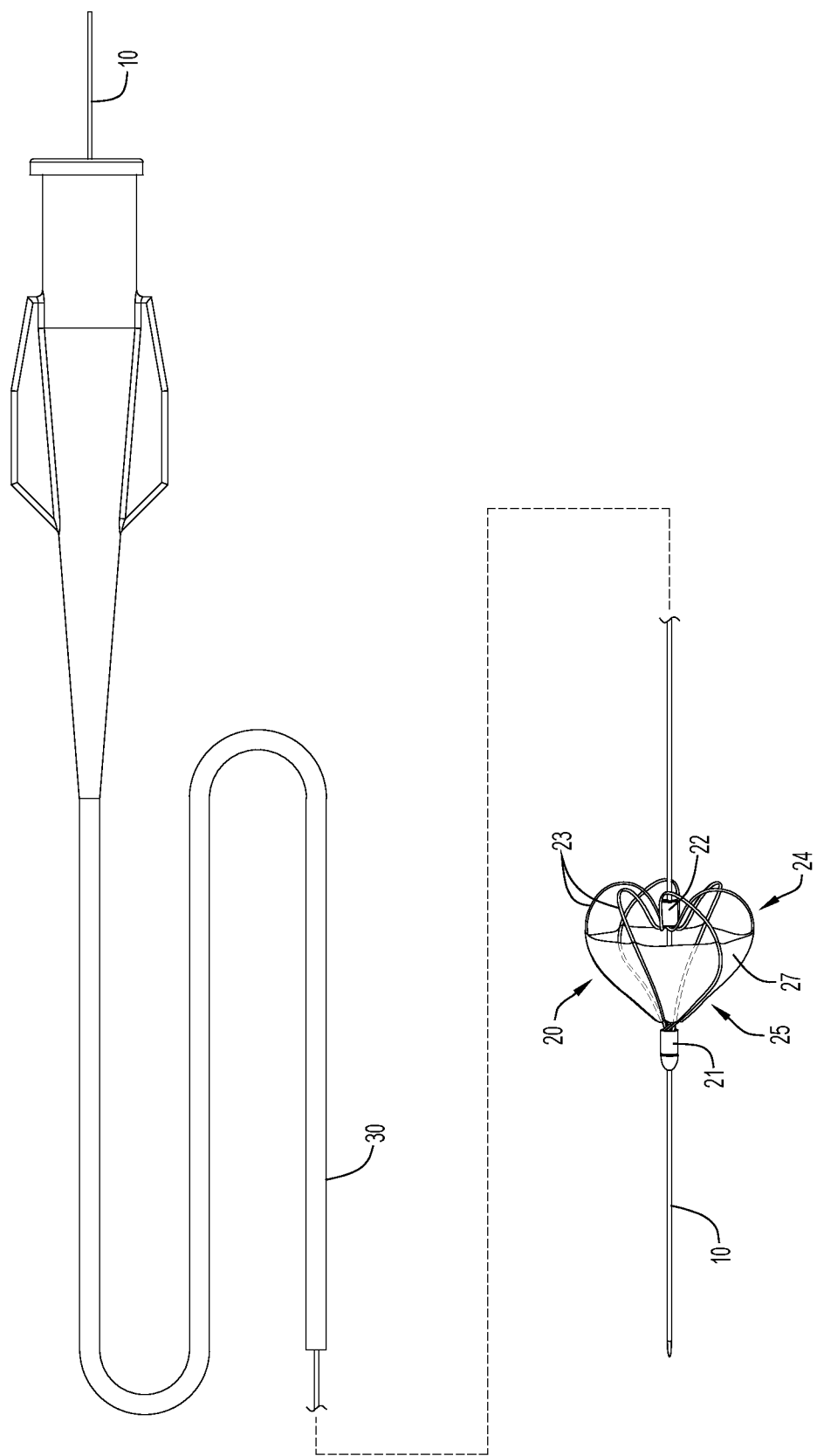
FIG. 1A illustrates an obstruction retrieval assembly according to one implementation with the retrieval device in an expanded state.

FIG. 1A illustrates an assembly useful in removing obstructions located within a bodily duct of a patient, such as, for example, the removal of blood clots located in the cerebral anatomy. According to some implementations the assembly includes a retrieval device 20 that is affixed to an elongate wire 10. In use, the retrieval device 20 is delivered to the site of an obstruction while being radially constrained inside a delivery catheter 30 as shown in FIG. 2B. Methods of delivering the retrieval device to the obstruction site and thereafter retrieving the obstruction are disclosed in more detail below.

As discussed above, although the example implementations disclosed herein are directed to the removal of blood clots located within the vasculature of a patient, it is appreciated that the devices, assemblies and methods are applicable to the retrieval of other types of obstructions located in other bodily cavities of the patient.

Figure 1B:
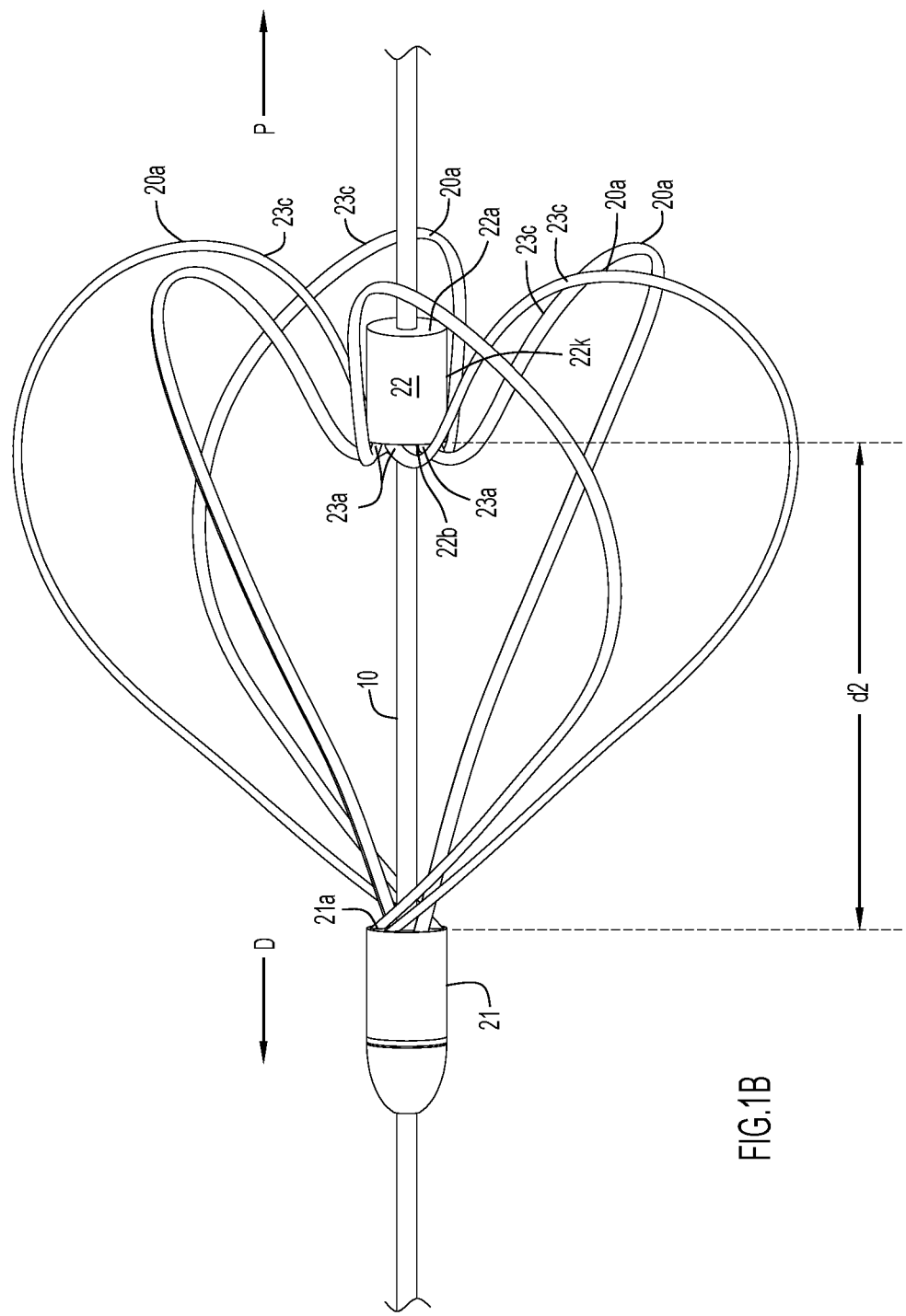
FIG. 1B illustrates an enlarged view of the retrieval device shown in FIG. 1A with the distal cover removed and the proximal collar located a first distance from the distal collar.
Figure 1C:
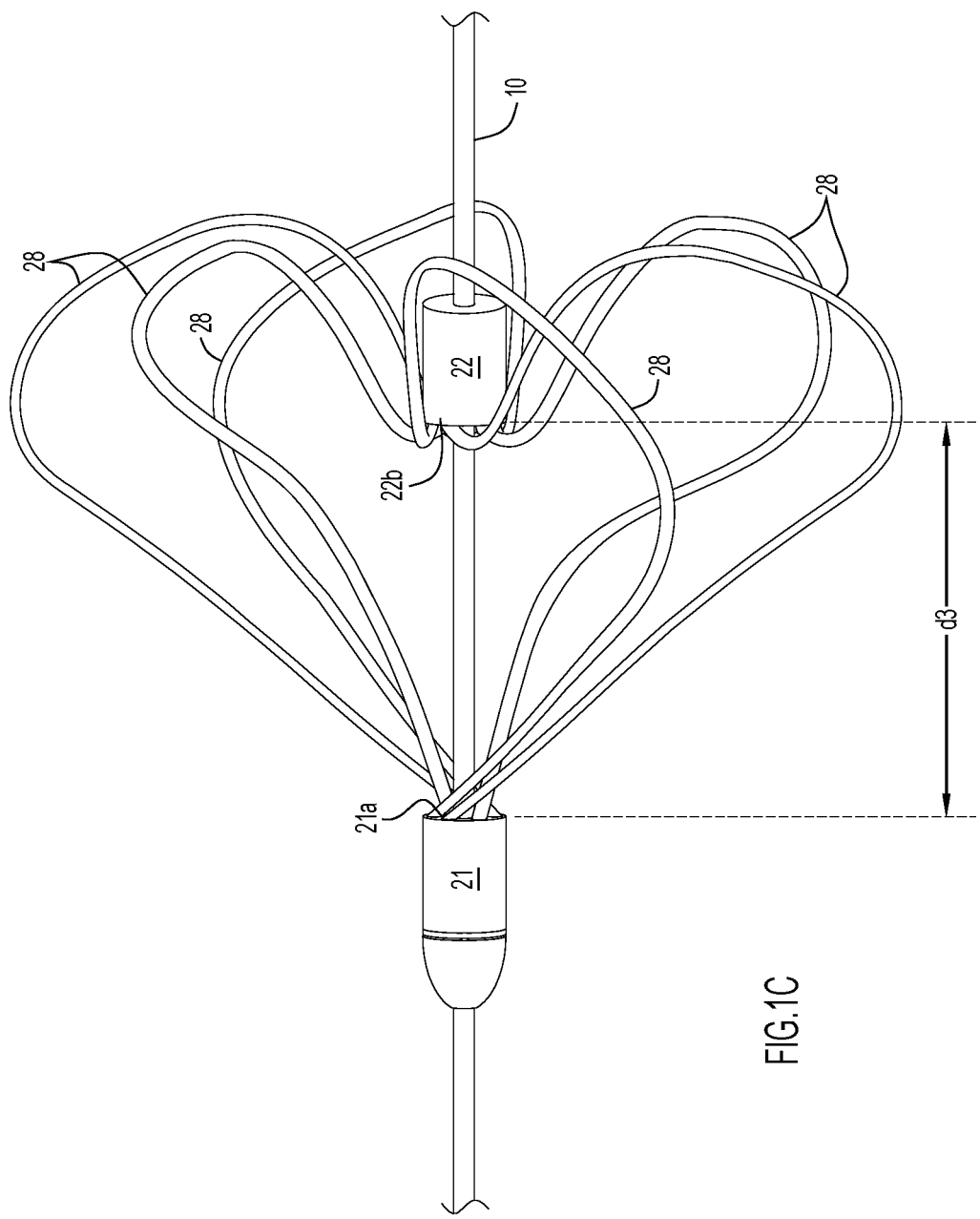
FIG. 1C illustrates an enlarged view of the retrieval device shown in FIG. 1A with the distal cover removed and the proximal collar located a second distance from the distal collar that is less than the first distance.

According to some implementations the retrieval device 20 includes a distal collar 21 fixed stationary to the elongate wire 10, and a proximal collar 22 that is slideable on the elongate wire 10. Extending between the proximal and distal collars are multiple shape memory elongate clot capturing elements 23 that are configured to engage the obstruction when the retrieval device 20 is in an expanded/deployed state as shown in FIGS. 1A-C. When the retrieval device is an expanded/deployed state, the shape memory elongate clot capturing elements 23 may assume a curved configuration like those shown in the figures or different than those shown in the figures. Hereinafter, when a shape memory elongate clot capturing element 23 is in its expanded/deployed state, it is referred to as "arch" or as having an "arched configuration" or "arched structure". As used herein, the terms "arch" and "arched" are not meant to denote any particular curvature of the clot capturing elements 23. Notwithstanding the foregoing, the clot capturing elements 23 assume curved configurations when the retrieval device 20 is in a deployed/expanded state sufficient to cause the clot capturing elements to engage the obstruction in a manner to facilitate an at least partial removal of the obstruction during the obstruction removal process.

In some implementations each of the shape memory elongate clot capturing elements 23 has a proximal end that is secured to the proximal collar 22 and a distal end that is secured to the distal collar 21. As shown in the figures, the proximal ends of the shape memory elongate clot capturing elements 23 may be attached to the distal end 22b of the proximal collar 22 and the distal ends of the shape memory elongate clot capturing elements 23 may be attached to the proximal end 21a of the distal collar 21. As will be discussed in more detail below, the shape memory elongate clot capturing elements 23 may comprise independent elements that are fixed to the proximal and distal collars by a bonding agent (e.g. an adhesive, solder, etc.) and/or by a bonding process (e.g. welding). The distal collar 21, proximal collar 22 and shape memory elongate clot capturing elements 23 may also be formed from a single piece of material, as will also be discussed in more detail below.

According to some implementations, when the retrieval device 20 is deployed from the delivery catheter 30 to assume an expanded state, it includes a proximal inverted portion 24 and a distal non-inverted portion 25. The proximal inverted portion 24 may be characterized by a dispersion of the shape memory elongate clot capturing elements 23 around an outer perimeter surface 22k of the proximal collar 22 when the retrieval device is in a deployed state. The proximal inverted portion 24 may be characterized by at least some portions 23c of the shape memory elongate clot capturing elements 23 being located proximal to their proximal terminal ends 23a when the retrieval device is in a deployed state, the proximal terminal ends 23a being coupled to or located inside the distal end portion 22b of the proximal collar 22. The proximal inverted portion 24 may be characterized by the proximal end 22a of the proximal collar 22 being located distal to a proximal-most end 20a of the retrieval device 20 when the retrieval device is in a deployed state. The proximal inverted portion 24 may be characterized by a zigzag configuration of the shape memory elongate clot capturing elements 23 in the inverted portion. That is, a portion of a shape memory elongate clot capturing element 23 initially extends from the distal end 22b of the proximal collar 22 towards a distal direction D and then changes course to extend towards a proximal direction P and then changes course to yet again extend towards the distal direction D as most clearly shown in FIG. 1B. The proximal inverted portion 24 may comprise one or any combination of the aforestated characteristics.

As shown in FIG. 1A, according to some implementations the distal non-inverted portion 25 of the retrieval device is provided with a cover 27 made of a permeable biocompatible material that is capable of capturing fragments of the obstruction that may become dislodged during the retrieval process. According to some implementations the biocompatible material is encapsulated polytetrafluoroethylene (ePTFE) with a thickness of 0.0008 to 0.016 inches. According to some implementations the portions of the shape memory elongate clot capturing elements 23 in the non-inverted portion 25 of the retrieval device 20 do not zigzag, but extend from the proximal end 21a of the distal collar 21 continuously towards the proximal direction P.

Figure 7B:
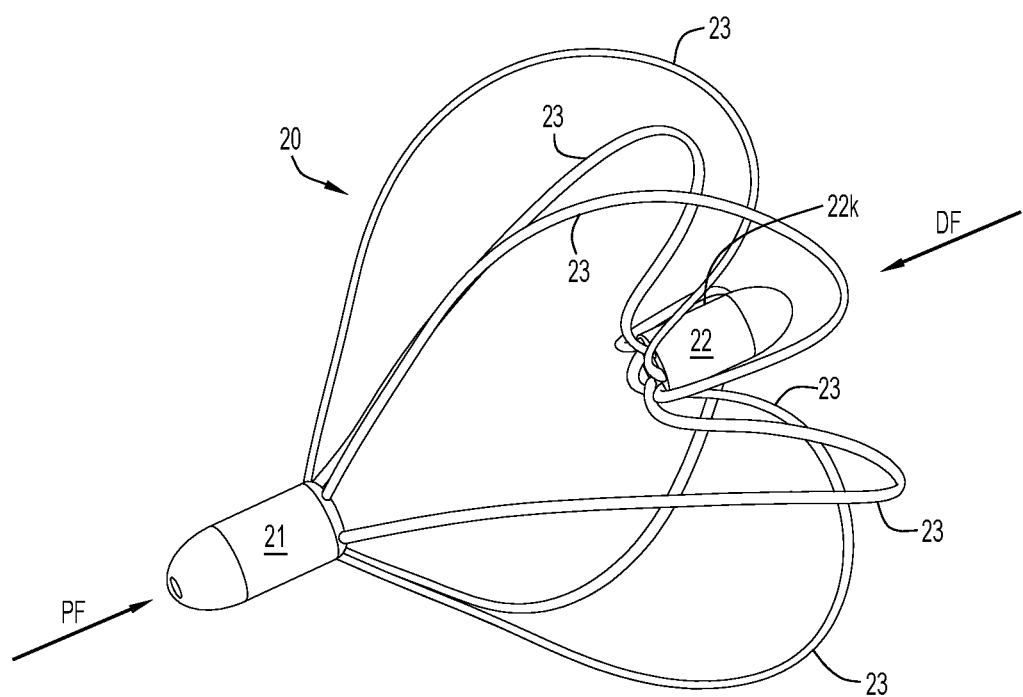
FIG. 7B shows the retrieval device of FIG. 7A upon there being an axial force applied to one or both of the proximal and distal collars to cause the proximal end portion of the retrieval device to invert.
Figure 7C:
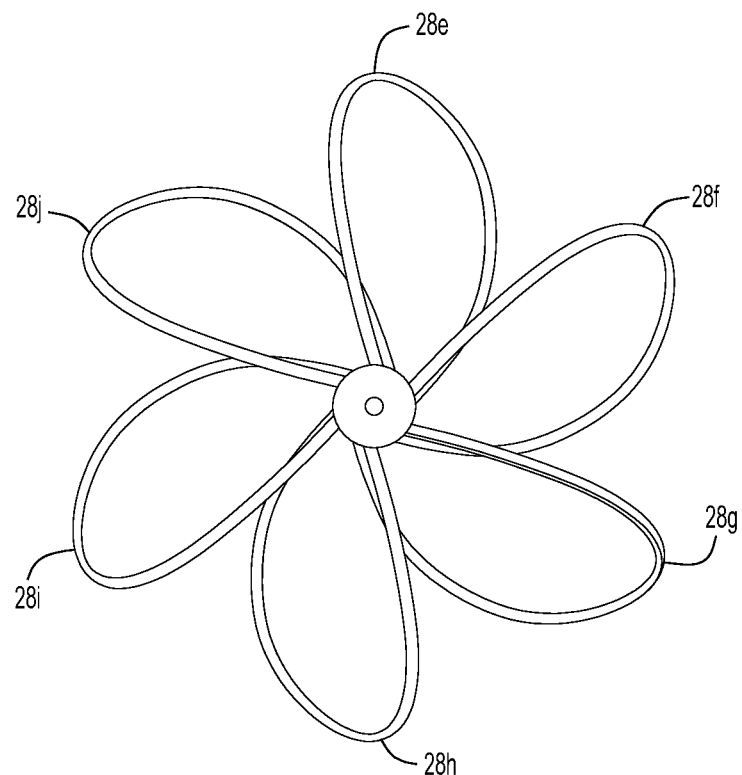
FIG. 7C shows a proximal end view of the retrieval device of FIG. 7B when one or both of the proximal and distal collars is rotated with respect to the other.
Figure 8A:
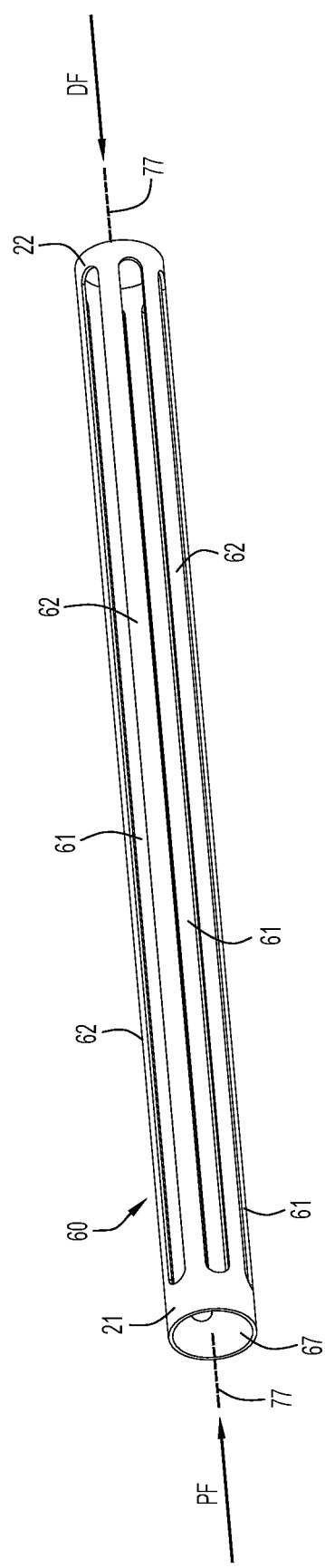
FIG. 8A illustrates a tubular member from which a retrieval device is unitarily made according to one implementation.
Figure 8B:
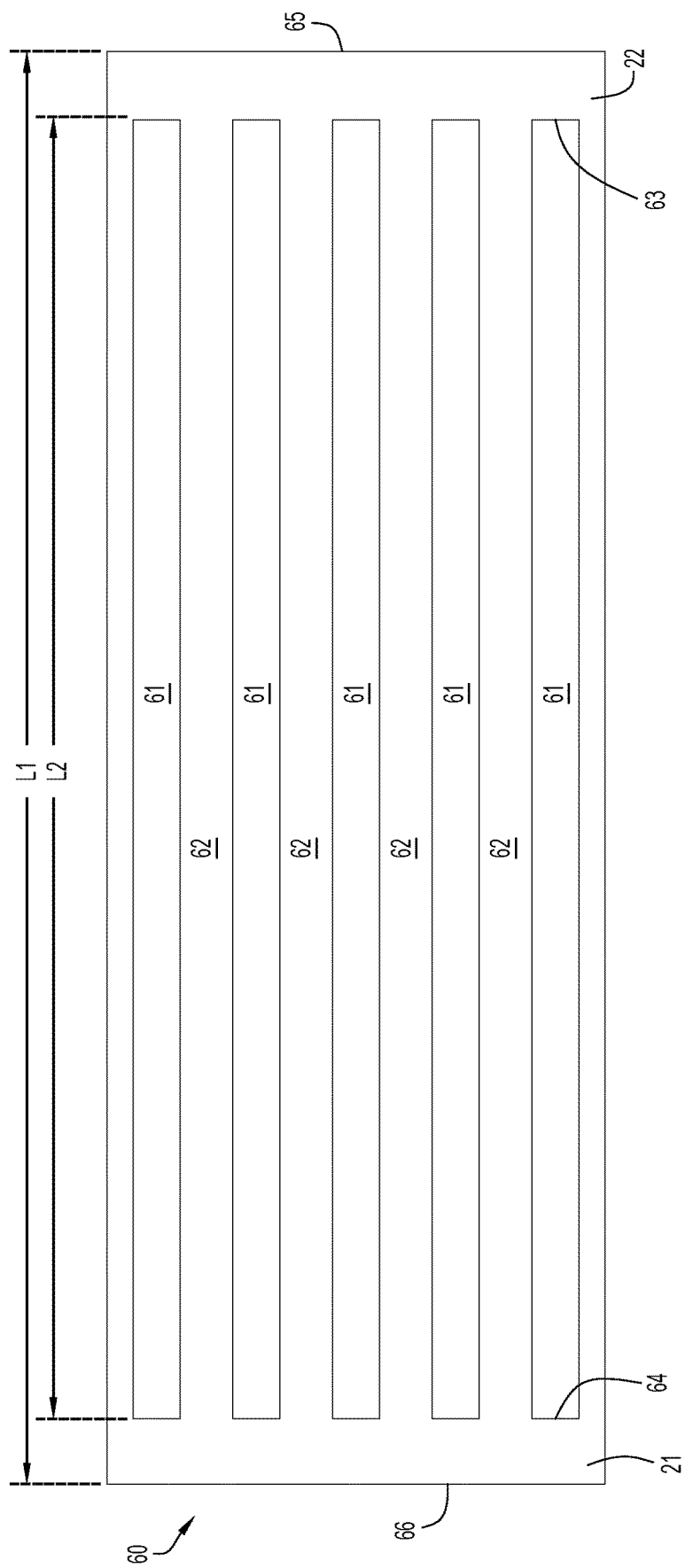
FIG. 8B shows the tubular member of FIG. 8A cut along its axial length and laid flat on a surface.
Figure 8C:
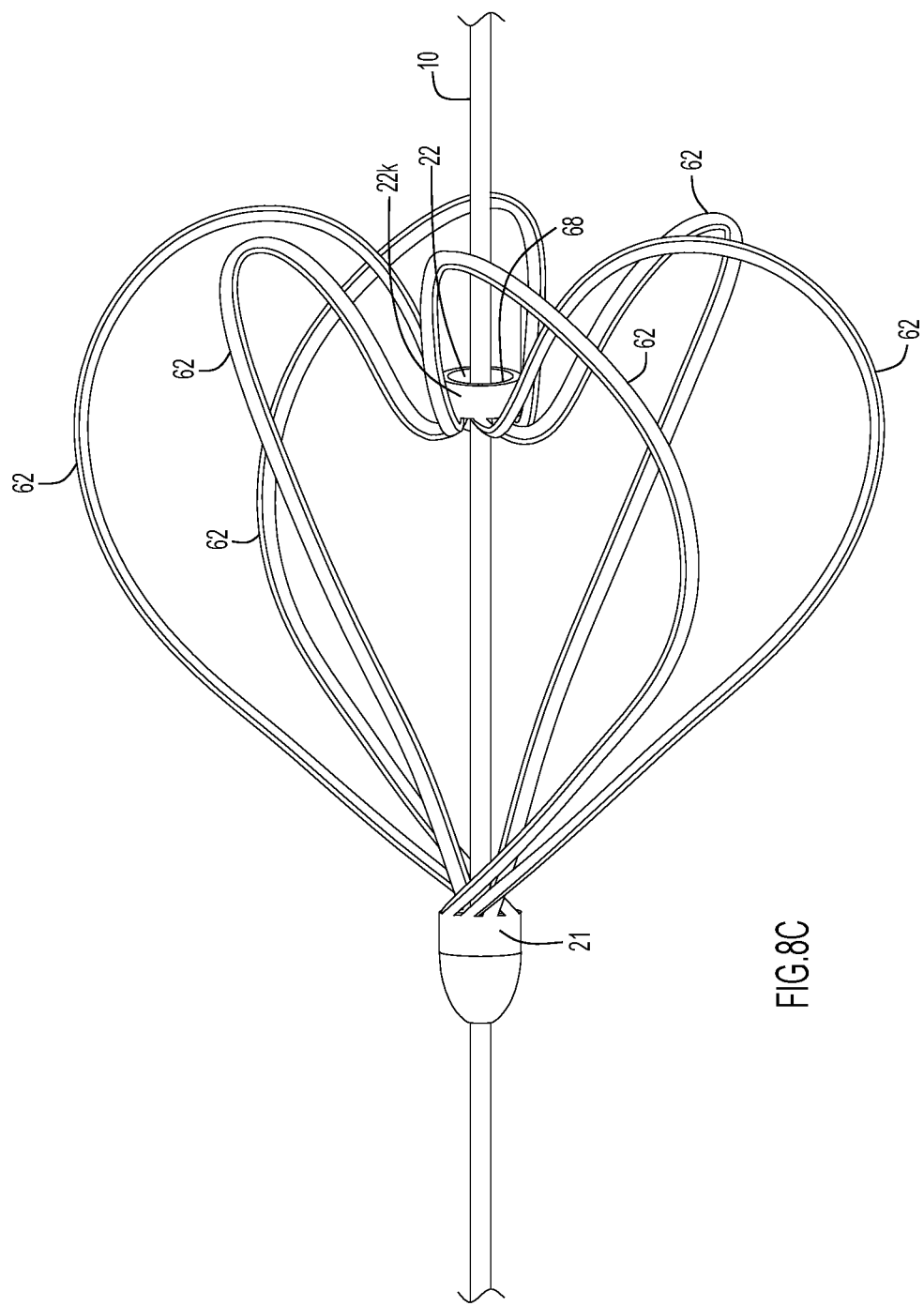
FIG. 8C shows the retrieval device having an inverted proximal end portion that is formed upon there being an axial force applied to one or both of the proximal and distal collars.
Figure 8D:
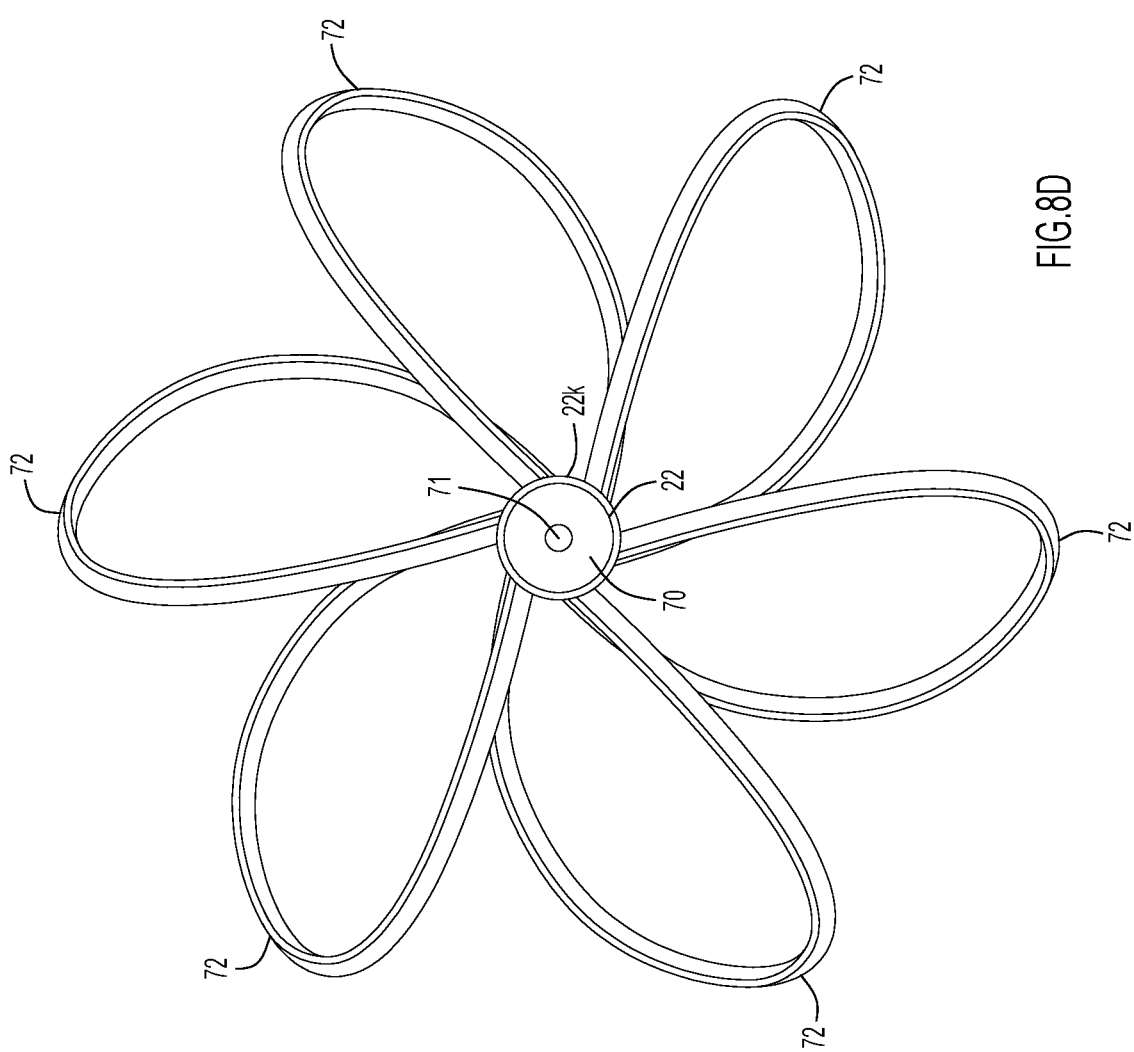
FIG. 8D shows an end view of the retrieval device of FIG. 8C after one or both of the proximal and distal collars is rotated with respect to one another to cause each of the elongate capture elements to assume an arched configuration.
Figure 10B:
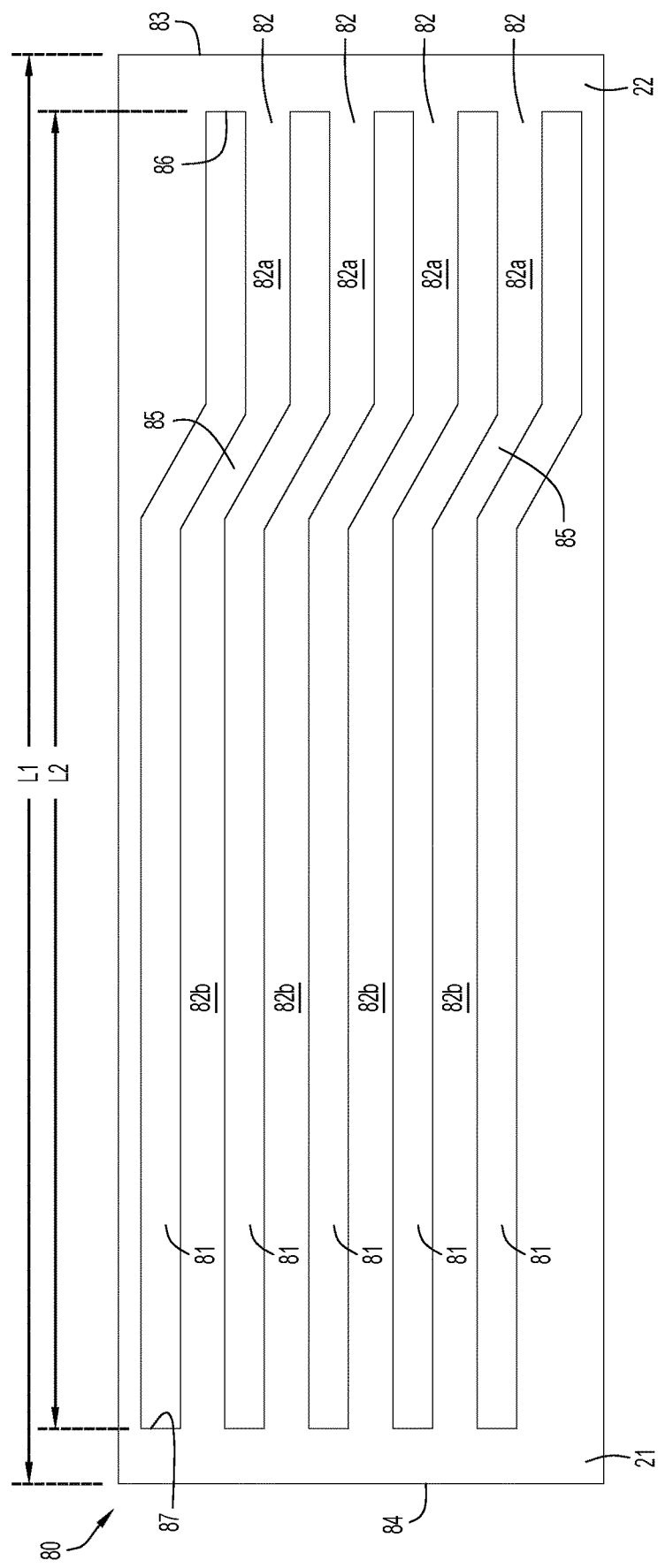
FIG. 10B shows the tubular member of FIG. 10A cut along its axial length and laid flat on a surface.
Figure 10D:
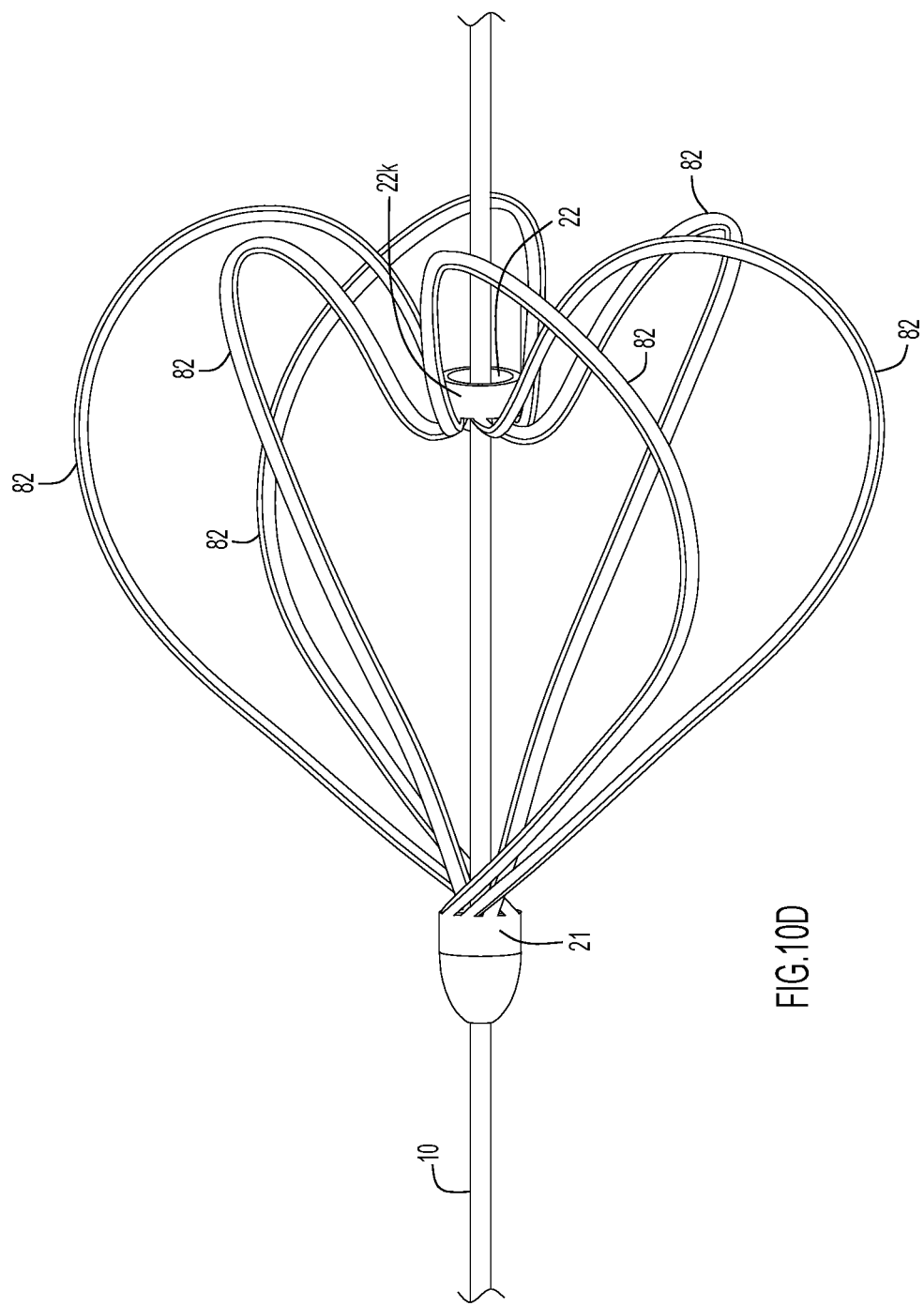
FIG. 10D shows an isometric view of a retrieval device formed from the tubular member of FIG. 10A.
Figure 10E:
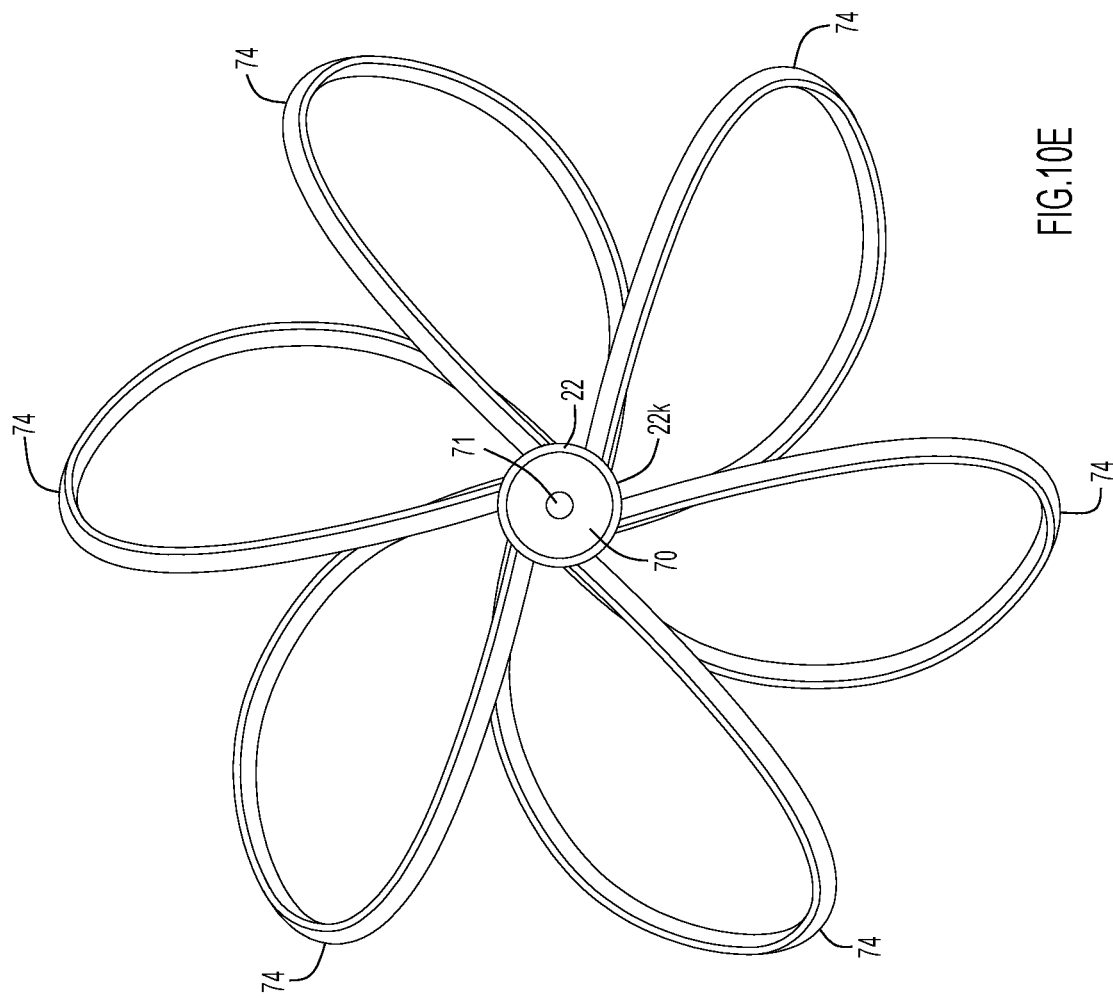
FIG. 10E is a proximal end view of the retrieval device of FIG. 10D.

According to some implementations, when the retrieval device 20 is in its expanded rest state the shape memory elongate clot capturing elements 23, as viewed from a proximal end of the retrieval device, form a plurality of arch structures like those shown in FIGS. 7C, 8D and 10E with adjoining arch structures preferably, but not necessarily, overlapping with one another.

Figure 2A:
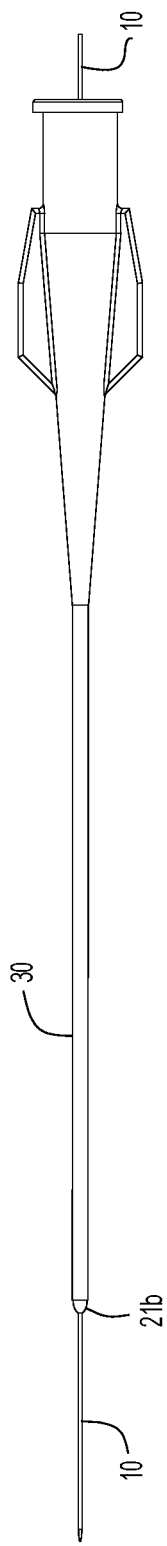
FIG. 2A shows a side view of the obstruction retrieval assembly of FIG. 1A with the retrieval device in a radially constrained state, positioned at a distal end of the delivery catheter.
Figure 2B:
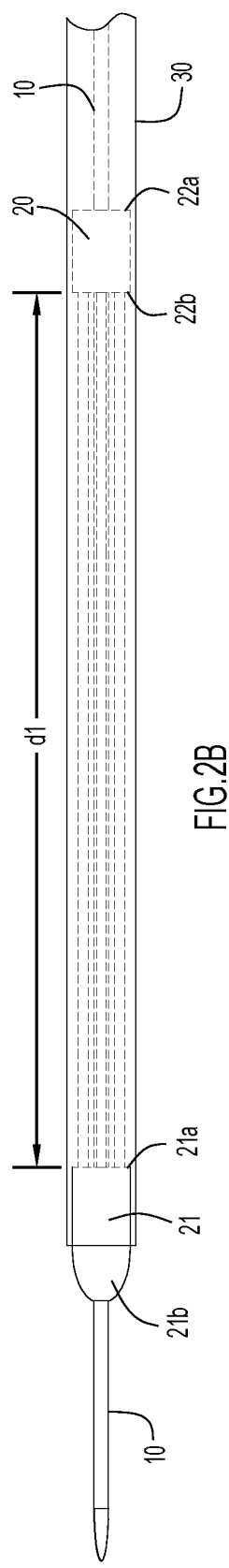
FIG. 2B is a cross-sectional side view of the distal end portion of the delivery catheter of FIG. 2A showing the retrieval device in a radially constrained state inside the delivery catheter.

FIG. 2A shows a side view of the obstruction retrieval assembly with the retrieval device 20 being located inside a distal end portion of the delivery catheter 30. FIG. 2B is a side cross-sectional view of the distal end portion of the delivery catheter 30 of FIG. 2A showing the retrieval device 20 radially constrained inside the delivery catheter. In the radially constrained state of the retrieval device 20 the proximal collar 22 is located at a first axial position on the elongate wire with the distal end 22b of the proximal collar 22 being spaced apart from the proximal end 21a of the distal collar 21 by a first distance d1. As shown in the figures, according to some implementations the distal collar 21 includes a curved/rounded atraumatic end 21b.

When the retrieval device 20 is in an unconstrained rest position, as shown in FIGS. 1A and 1B, the proximal collar 22 is located at a second axial position on the elongate wire 10 with the proximal end 21a of the distal collar 21 being located a second distance d2 away from the distal end 22b of the proximal collar 22, the second distance d2 being less than the first distance d1. When the retrieval device is in the expanded rest position, the proximal collar 22 is movable along a length of the elongate wire 10 to a third axial position such that the proximal end 21a of the distal collar 21 is located a third distance d3 away from the distal end 22b of the proximal collar 22, the third distance d3 being less than the second distance d2. The shortening of the distance between the proximal and distal collars from the second distance d2 to the third distance d3 urges the arch structures 28 to expand radially outward and/or causes the stiffness of the clot capturing elements 23 to increase as result of a more pronounced bending of the clot capturing elements. During a removal of a clot in the vasculature of a patient, a distal movement of the proximal collar 22 on the elongate wire 10 is particularly advantageous. It can result in the arch structures 28 being urged to radial expand so that they may more firmly press against the arterial wall during the clot retrieval process. A stiffening of the clot capturing elements 23 increases the rigidity of the clot capturing elements 23 making it more difficult for the arch structures 28 to prolapse during the clot retrieval process. In each case, the retrieval device's clot capturing capability is enhanced.

According to some implementations, one or both of the distal collar 21 and proximal collar 22 is made of a radiopaque material or coated with a radiopaque material that enables its location to be observed under fluoroscopy.

Figure 3:
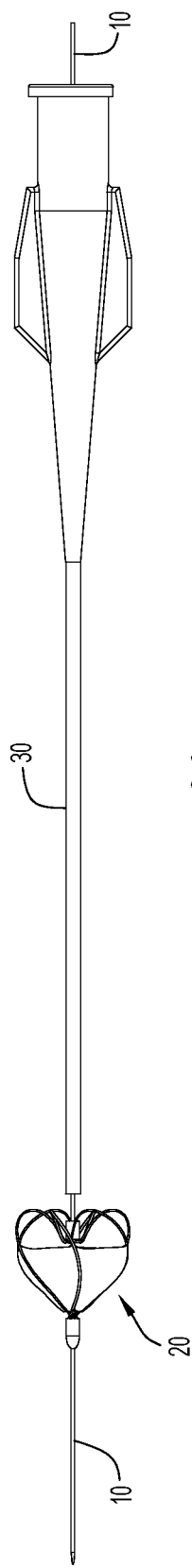
FIG. 3 shows a side view of the obstruction retrieval assembly of FIG. 2A with the delivery catheter withdrawn proximally to deploy the retrieval device.

FIG. 3 shows the retrieval device 20 in the deployed state. During use, the retrieval device 20 may be deployed out the distal end of the delivery catheter 30 by either withdrawing the delivery catheter in a proximal direction while holding the elongate wire 10 fixed or by holding the delivery catheter 30 fixed while distally advancing the elongate wire 10.

As discussed above, the distal collar 21, proximal collar 22 and shape memory elongate clot capture elements 23 of the retrieval device 20 may comprise a collection of parts that are assembled together or may be formed from a single piece of material. FIGS. 4A-7C are directed to retrieval devices comprised of a collection of parts and FIGS. 8A-19B are directed to retrieval devices of unitary construction (i.e. made from a single piece of material).

Figure 4A:
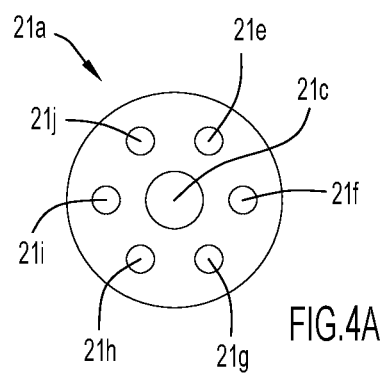
FIGS. 4A and 4B respectively show a proximal end view and a cross-sectional side view of a distal collar of a retrieval device according to one implementation.
Figure 4B:
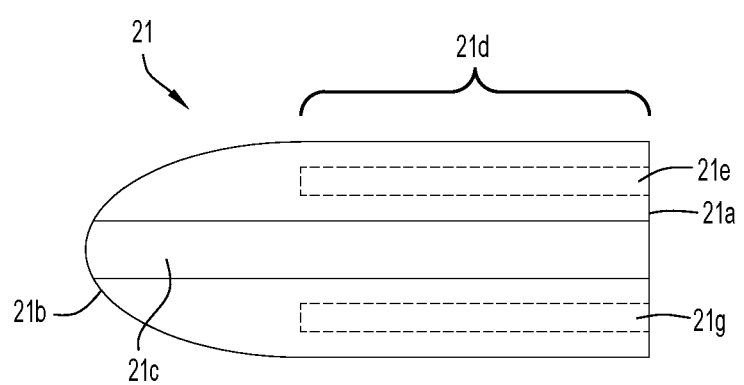

FIGS. 4A and 4B respectively show a proximal end view and a cross-sectional side view of a distal collar 21 according to one implementation. The distal collar 21 includes a central through opening 21c through which the elongate wire 10 passes when the distal collar is fixed to the elongate wire. According to some implementations the proximal end portion 21d of the collar includes a plurality of apertures 21e-j that are radially arranged about the central opening 21c. The apertures 21e-j may be blind apertures as shown in FIG. 4B or may comprise through apertures with distal openings. According to some implementations the apertures 21e-j are equidistantly spaced around the central opening 21c as shown in FIG. 4A. According to some implementations, the outer surface of the distal end 21b of the distal collar is curved to minimize tissue injury when the retriever 20 is maneuvered through the vasculature of the patient.

Figure 5A:
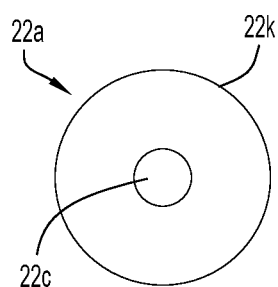
FIGS. 5A, 5B and 5C respectively show a proximal end view, distal end view and cross-sectional side view of a proximal collar of a retrieval device according to one implementation.
Figure 5B:
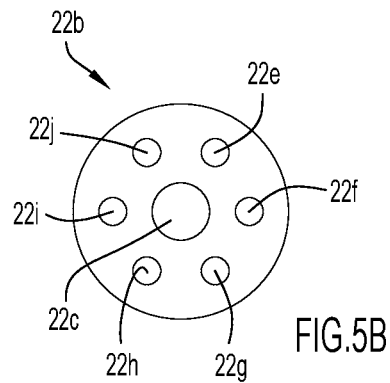
Figure 5C:
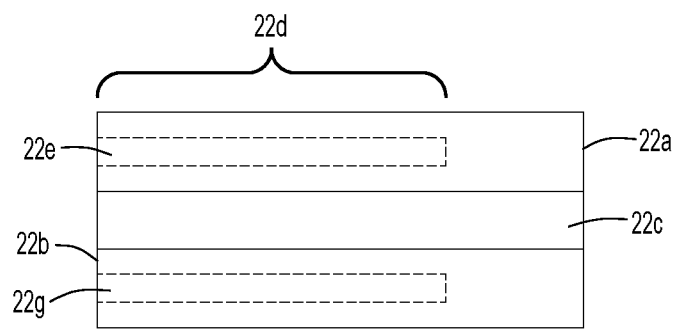

FIGS. 5A, 5B and 5C respectively show a proximal end view, distal end view and cross-sectional side view of the proximal collar 22 according to some implementations. The proximal collar 22 includes a central through opening 22c through which the elongate wire 10 passes when the proximal collar is mounted on the elongate wire in a slideable manner. According to some implementations the distal end portion 22d of the collar includes a plurality of apertures 22e-j that are radially arranged about the central opening 22c. The apertures 22e-j may be blind apertures as shown in FIG. 5C or may comprise through apertures that extend through the entire length of the collar. According to some implementations the apertures 22e-j are equidistantly spaced around the central opening 22c as shown in FIG. 5B. According to some implementations, the proximal end 22a of the proximal collar 22 is curved as shown in FIG. 5D for the purpose of minimizing tissue injury when the retriever 20 is maneuvered through the vasculature of the patient.

In the examples of FIGS. 4A-B and 5A-D each of the proximal and distal collars 22 and 21 respectively possesses six apertures 22e-j and 21e-j that are configured to respectively receive the proximal ends 23a and distal ends 23b of six shape memory elongate clot capturing elements 23e-j as shown in FIG. 6. According to some implementations the shape memory elongate clot capturing elements are fixed inside the apertures of the proximal and distal collars by use of an adhesive or other means as discussed above.

Throughout the present disclosure the example retrievers are shown to possess five or six shape memory elongate clot capturing elements. It is important to note that the retrievers may have fewer or more than five or six shape memory elongate clot capturing elements.

Figure 5D:
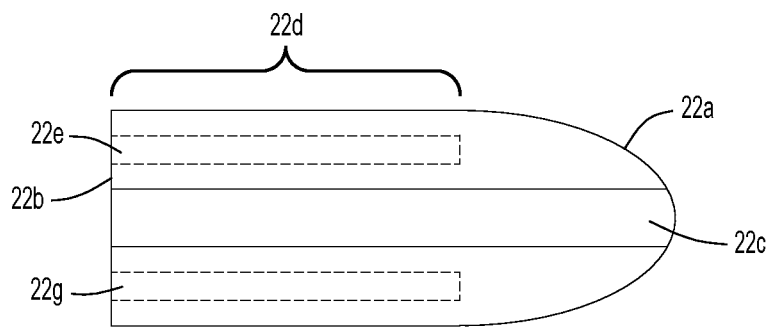
FIG. 5D is a cross-sectional side view of a proximal collar of a retrieval device having an atraumatic proximal end.

FIG. 7 shows the shape memory elongate clot capturing elements 23e-j fixed to the distal and proximal collars 21 and 22 depicted in FIGS. 4B and 5D. According to some implementations the shape memory elongate clot capturing elements 23-j are made of Nitinol and are shape-set in their respective rest state configurations as shown in FIGS. 1A and 1B by heating the clot capturing elements above their martensitic transformation temperature. Thereafter, when the clot capturing elements 23 are radially constrained and thereafter unconstrained they automatically aspire to assume their expanded rest states.

Shaping of the clot capturing elements 23 to assume their expanded rest states may include applying a distal force DF to the proximal collar 22 and/or a proximal force PF to the distal collar 21 as shown in FIG. 7A while rotating one or both of the distal and proximal collars with respect to one another in the clockwise or counter-clockwise direction. Alternatively or in conjunction with aforesaid shaping method, the clot capturing elements 23 may be constrained in their expanded rest state configurations using a specially designed fixture. In either case, the clot capturing elements 23 may be heat treated as discussed above to lock them in their expanded rest state configurations.

As shown in FIG. 7B, upon the distal force DF being applied to the proximal collar 22 and/or upon a proximal force PF being applied to the distal collar 21, an inversion occurs as the proximal collar 22 is moved nearer to the distal collar 21, resulting in the outer peripheral surface 22k of the proximal collar 22 being at least partially surrounded by bent portions of the clot capturing elements 21e j. According to one implementation, during or after the inversion, one or both of the distal collar 21 and proximal collar 22 are rotated with respect to the other to cause the clot retrieval elements to assume an arched configuration as shown in FIG. 7C with at least portions of adjacent arched structures overlapping with one another.

According to some implementations, when the retrieval device 20 has been formed into its expanded rest state, it is mounted to the elongate wire 10 and is thereafter stored in a radially constrained state inside, for example, a peel-away sheath. During a subsequent clot removal process, the retrieval device 20 is loaded into the delivery catheter 30 in its radially constrained state and made ready for deployment outside the delivery catheter into the vasculature of the patient.

Figure 19A:
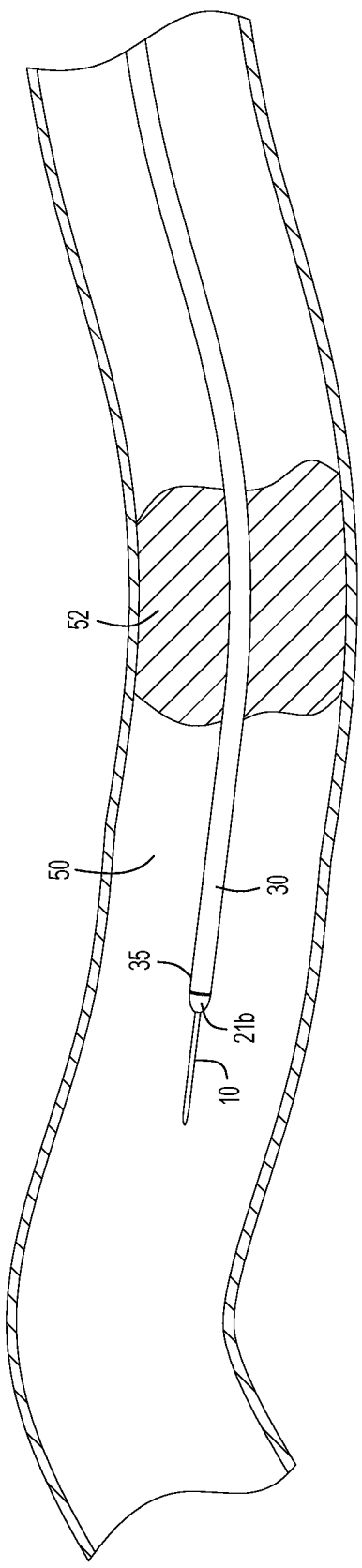
FIGS. 19A-D show a method for capturing an obstruction in a bodily duct of a patient according to one implementation.
Figure 19B:
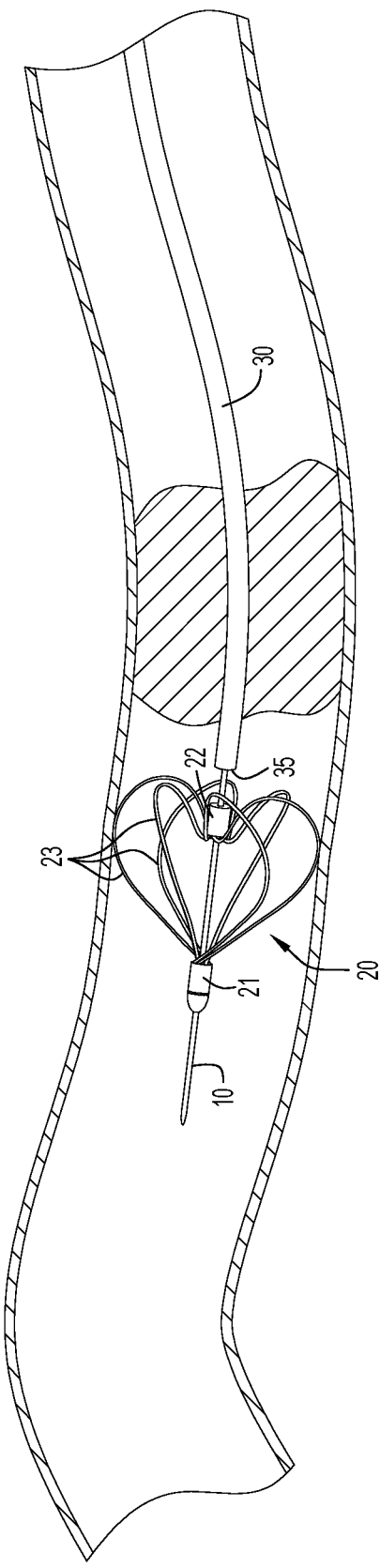

FIGS. 19A-D illustrate a method through which a clot 52 may be removed from an arterial passageway 50 of a patient. The process typically includes the delivery of a guidewire across the clot 52 and a subsequent advancement of the delivery catheter 30 over the guidewire so that a distal end portion of the delivery catheter resides distal to the clot 52. With the delivery catheter in place, the retrieval device 20 is loaded into the delivery catheter 30 as described above. According to some implementations, the retrieval device 20 is positioned in the distal end portion of the delivery catheter 30 such that only its distal curved end 21b protrudes from the distal end 35 of the delivery catheter 30 as shown in FIG. 19A. Thereafter, the retrieval device 20 is deployed from the delivery catheter 30 as shown in FIG. 19B. As discussed above, the retrieval device 20 may be deployed out the distal end of the delivery catheter 30 by either withdrawing the delivery catheter in a proximal direction while holding the elongate wire 10 fixed or by holding the delivery catheter 30 fixed while distally advancing the elongate wire 10.

Figure 19C:
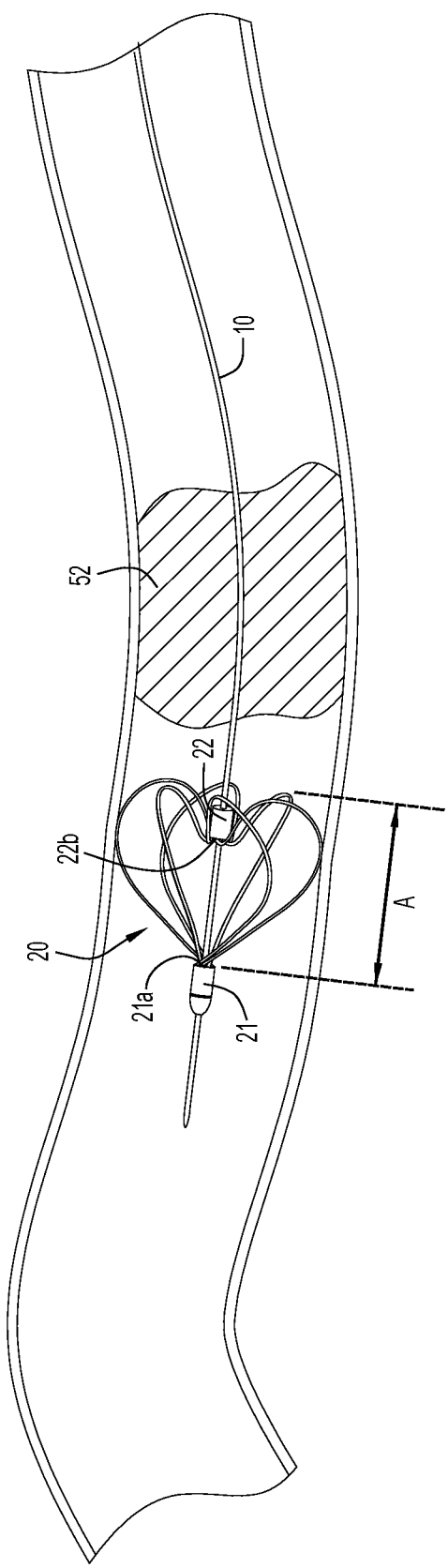
Figure 19D:
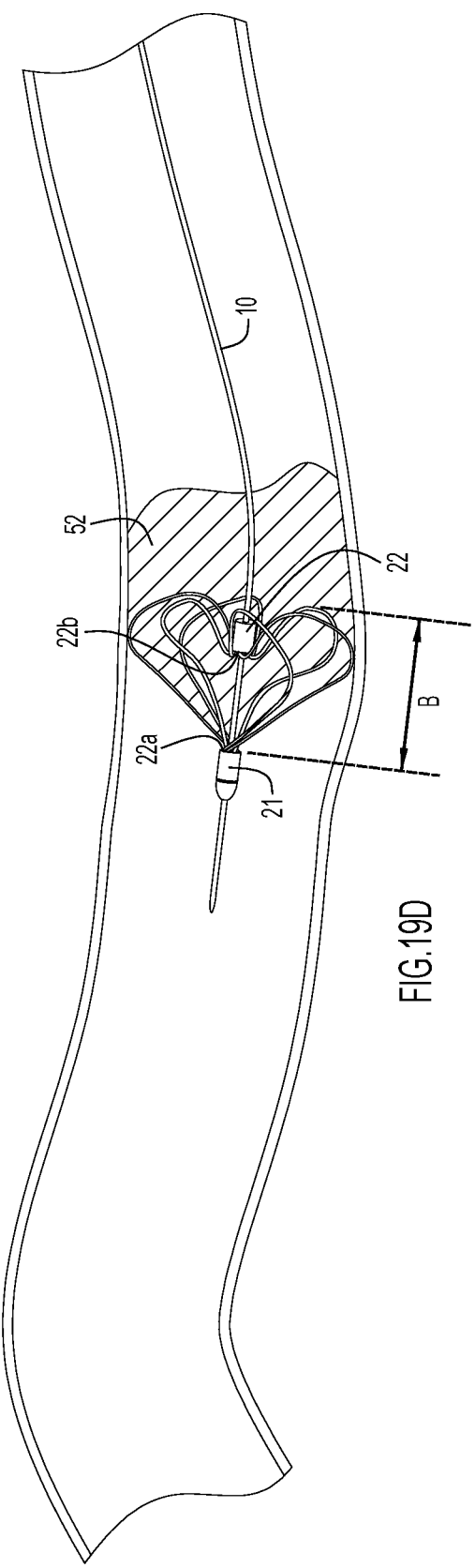

When in the deployed state inside the passageway 50 of the patient, the arched clot capturing elements 23 of the retrieval device 20 press against the arterial wall 54 of the vessel. (Note that when the retrieval device is deployed inside the arterial passageway of the patient it is sized not achieve its expanded rest state as a result of its maximum rest state diametric dimension being sized greater than the diameter of the arterial passageway.) After the retrieval device 20 is deployed inside the passageway 50, the delivery catheter 30 is withdrawn as shown in FIG. 19C with the retrieval device 20 made ready to be pulled proximally to engage the clot 52. As shown in FIG. 19C, just prior to the retrieval device 20 engaging the clot 52, the distal end 22b of the proximal collar 22 is spaced apart from the proximal end 21a of the distal collar 21 by a distance A. According to some implementations, as the retrieval device 20 is pulled proximally into the clot 52, the proximal collar 22 moves distally closer to the distal collar 21 such that the distal end 22b of the proximal collar 22 is spaced apart from the proximal end 21a of the distal collar 21 by a distance B that is less than the distance A as shown in FIG. 19D. The advantages associated with the distal movement of the proximal collar 22 on the elongate wire 10 during clot capture are discussed above.

Upon the clot 52 being captured by the retrieval device 20, removal of the clot may be accomplished, at least in part, by the elongate wire 10 being pulled proximally to move the clot to a mouth of an aspiration catheter or into the delivery catheter 30.

In some implementations the clot capturing elements 23 of retrieval device 20 are configured to sweep along the arterial wall 54 to which the clot is attached during the removal process to cause the clot, or remnants of the clot, to be moved centrally towards the center of the affected vessel 50.

Figure 1D:
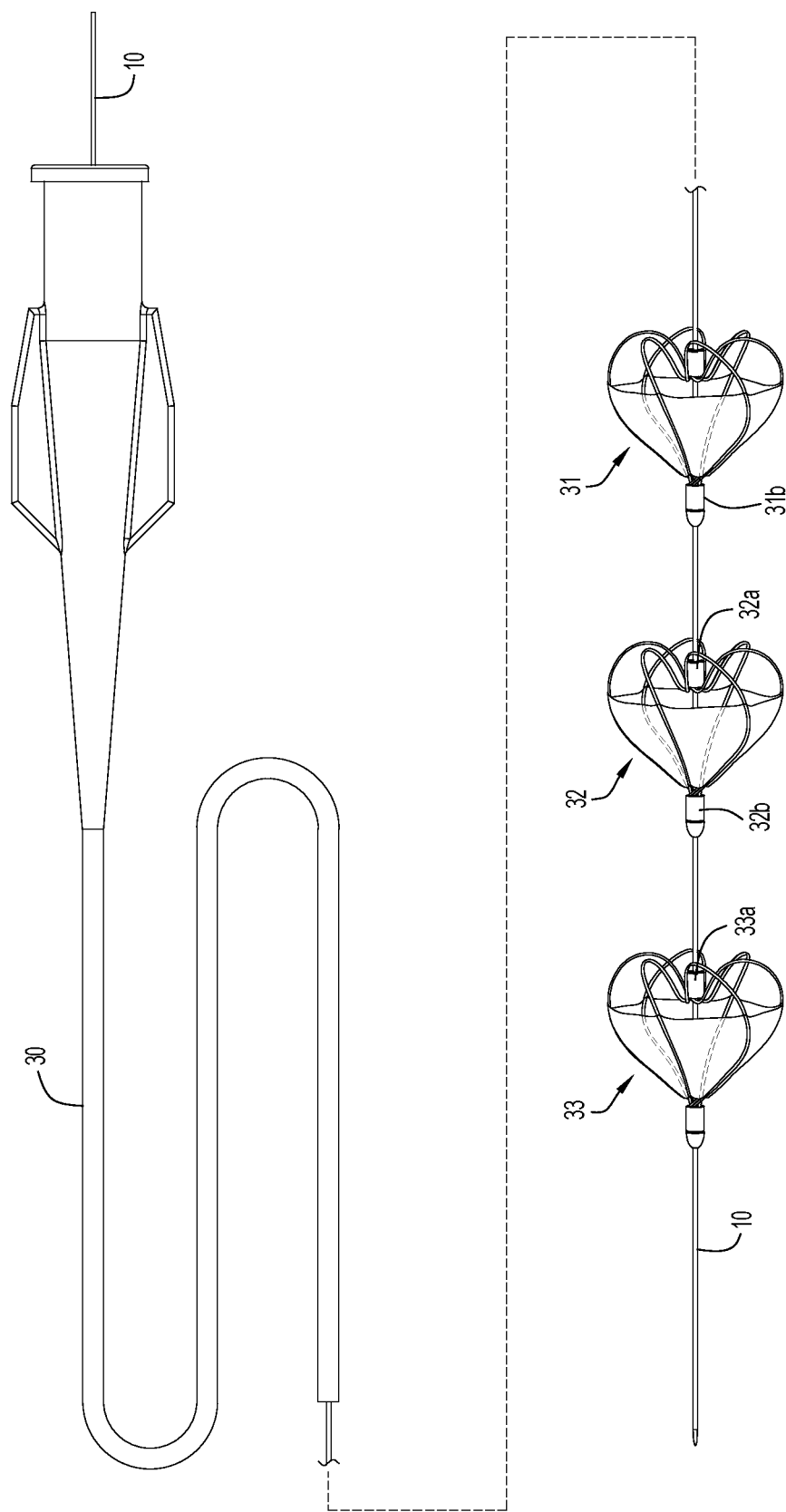
FIG. 1D illustrates an obstruction retrieval assembly like that of FIG. 1A having multiple retrieval devices.

In the implementations of FIGS. 1A and 19A-D the clot retrieval assembly includes a single retrieval device 20. According to other implementations the retrieval assembly includes multiple retrieval devices spaced apart along the axial length of the elongate wire 10. In use, the two or more retrieval devices are each deployed distal to the clot 52. The use of two or more retrieval devices allows remnants of the clot 52 not captured by a proximally disposed retrieval device to be captured by a distally disposed retrieval device. FIG. 1D shows an exemplary retrieval assembly having three retrieval devices 31, 32 and 33 in their expanded rest states disposed along a length of a distal end portion of the elongate wire 10. According to some implementations the retrieval devices 31, 32 and 33 are spaced apart and configured such that when they are stored in their radially constrained state inside a sheath or inside the delivery catheter 30, the slideable proximal collar 33a of retrieval device 33 is located distal to the fixed distal collar 32b of retrieval device 32 and the slideable proximal collar 32a of retrieval device 32 is located distal to the fixed distal collar 31b of retrieval device 31. In the example of FIG. 1D, retrieval device 32 is spaced equidistantly between retrieval devices 31 and 33. According to another implementation retrieval device 32 is located nearer to retrieval device 31 than to retrieval device 33. According to another implementation the retrieval device 32 is located nearer to retrieval device 33 than to retrieval device 31.

According to some implementations the elongate wire 10 has a length of about 200 centimeters and a diameter of between about 0.01 and 0.014 inches. The term "about" when used in conjunction with describing a dimensional characteristic herein denotes the stated dimension ±10%. (For example, the statement of the elongate wire 10 having a length of about 200 centimeters means a length of between 180 to 220 centimeters.) According to some implementations the delivery catheter 30 has a length of about 150 centimeters and an inner diameter of about 0.027 inches. According to some implementations the retrieval device 20 has a radial constrained length of between about 16 to 30 millimeters and a length of between about 8 to 15 millimeters when the retrieval device in the expanded rest state. When the retrieval device 20 is in the expanded rest state, the maximum diametric dimension of the expanded device is between about 3 to 6 millimeters. According to some implementations the shape memory elongate clot capturing elements 23 have a diameter of between about 0.0002 to 0.0008 inches. (It is important to note that the accompanying figures are not drawn to scale.)

As discussed above, according to some implementations the retrieval device 20 is of a unitary construction with the proximal collar 22, distal collar 21 and clot capturing elements 23 being made from a single piece of material. According to some implementations the single piece of material is a Nitinol tube.

FIGS. 8A-D illustrate a method of making a retrieval device according to one implementation. According to some implementations the method includes laser cutting a Nitinol tube 60 to form a plurality of circumferentially spaced-apart longitudinally slots 61 to form a plurality of spaced-apart elongate clot capturing elements 62 that extend continuously (i.e. without any breaks or interruptions) along a substantial length L1 of the tube 60. FIG. 8B shows the slotted tube 60 of FIG. 8A as if it were cut along its length and laid flat on a surface.

The slots 61 have proximal ends 63 that are spaced a distance away from the proximal end 65 of tube 60 in order to form the proximal collar 22. Likewise, the slots 61 have a distal end 64 that is spaced a distance away from the distal end 66 of tube 60 in order to form the distal collar 21. The length distance L2 between the proximal and distal ends 63 and 64 of the slot are thus less than the length L1 of the tube 60. Each of the length distances L1 and L2 is a straight line distance that runs parallel to the longitudinal axis 164 of tube 160 as shown in FIG. 8B. According to some implementations length L2 is at least 50% the length L1, and preferably at least 70% the length L1.

After the formation of the slots 61, the tube 60 may be polished to remove slag (oxides) formed during the laser cutting process. Thereafter, the device may be manipulated like that described above in conjunction with the implementations of FIGS. 7A-C to cause the clot capturing elements 62 to assume a bent configuration as shown in FIGS. 8C and 8D. According to one method, the retrieval device is formed by applying a distal force DF to the proximal collar 22 and/or applying a proximal force PF to the distal collar 21 as shown in FIG. 8A to cause an inversion of the clot capturing elements 62 at a proximal end portion of the device. Simultaneously with applying one or both of the distal force DF and proximal force PF, or at a time after the inversion has occurred, one or both of the distal collar 21 and proximal collar 22 may be rotated clockwise or counter-clockwise with respect to other to cause at least some of the clot capturing elements 62a-e to assume an arched configuration. FIG. 8D is a proximal end view of the retrieval device showing the clot capturing elements 62 in their arched configurations. According to some implementations at least some of the arched structures 72 overlap with one another as shown in FIG. 8D. According to some implementations the length of the retrieval device 20 in its expanded rest state is 40% to 70% the pre-inversion length of the tube 60.

In order to shape-set the clot capturing elements 62 into their respective expanded rest state configurations as shown in FIGS. 8C and 8D, the clot capturing elements are heat treated in their rest state configurations so that when they are radially constrained and thereafter unconstrained they are automatically urged towards their expanded rest states. As discussed above, shaping the clot capturing elements 62 may include applying a distal force DF to the proximal collar 22 and/or a proximal force PF to the distal collar 21 while simultaneously or later rotating one or both of the distal and proximal collars with respect to one another in the clockwise or counter-clockwise direction. Alternatively or in conjunction with aforesaid shaping method, the clot capturing elements 62 may be constrained in their expanded rest state configurations using a specially designed fixture. In either case, the clot capturing elements 62 are heat treated to lock them in their expanded rest state configurations.

Figure 11:
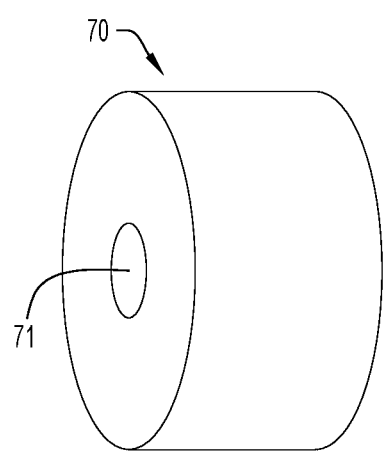
FIG. 11 illustrates an insert for placement inside the annular openings of the proximal and distal collars

According to some implementations, a cylindrical collar 70 like that shown in FIG. 11 is fitted into one or both of the annular openings 67 and 68 of the distal and proximal collars 21 and 22. The cylindrical collar 70 includes a central through opening 71 that has a smaller diameter than the diameter of the annular through openings 67 and 68. The smaller diameter opening 71 enables the retrieval device 20 to be more centrally located on the elongate wire 10 and makes for a smoother and more controlled sliding action of the proximal collar 22 on the elongate wire 10 as the retrieval device transitions from its radially constrained state to its expanded rest state and also when the retrieval device transitions from its expanded rest state to its expanded stressed state. According to some implementations the central through opening 71 of collar 70 has an inner diameter that is 5% to 20% greater than the outer diameter of the elongate wire 10. FIG. 8D shows the cylindrical collar 70 located in the annular through opening 68 of the proximal collar 22. The collar 70 may be placed in one or both of the proximal and distal collars of all retrieval devices disclosed and contemplated herein that are made from a slotted tube.

According to other implementations the slots 61 are cut such that the proximal and distal end sections 62a and 62b of the clot capturing elements 62 have different widths with the width of the distal end sections 62b being greater than the width of the proximal end sections 62a as shown in FIG. 8E. (The proximal end sections 61a of the slots 61 having a greater width than the width of the distal end section 61b of the slots 61.) The provision of the distal end sections 62b having a greater width results in smaller gaps existing between them when the resultant retrieval device is in an expanded/deployed state. This advantageously impedes to a greater extent the passage of dislodged clot fragments across the retrieval device during a clot retrieval procedure.

Figure 9A:
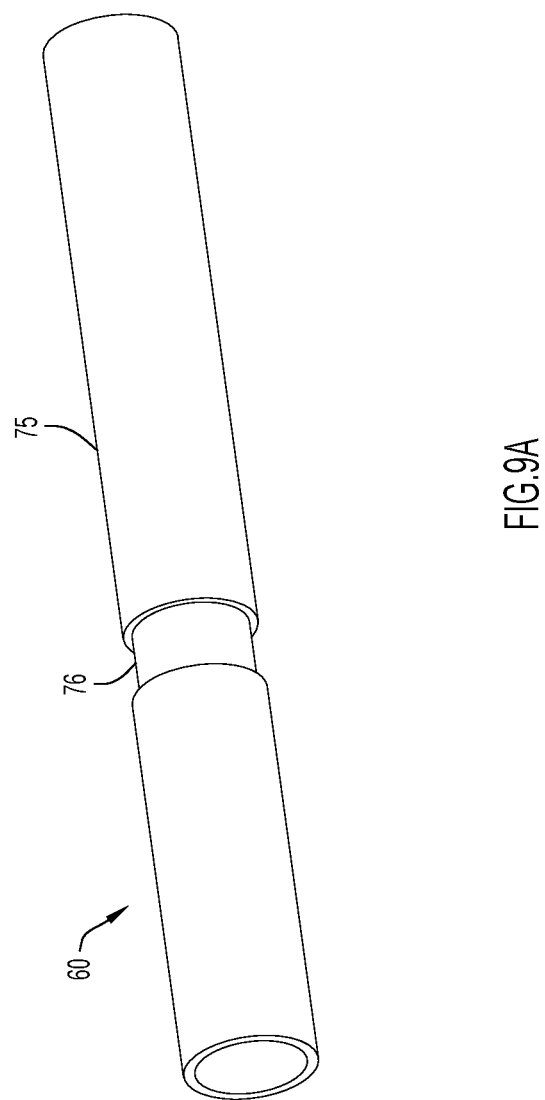
FIG. 9A illustrates a Nitinol tube having a thinned wall section along a portion of its length.

The formation of the inverted part of the retrieval device requires an initial buckling or outward bending of the clot capturing elements 62 somewhere along their length. As shown in FIGS. 9A and 9B, the slotted tube 60 may be provided with a reduced wall thickness region 69 somewhere along its length in order to control the location of the initial buckling or outward bending. The reduced wall thickness region 69 may take on any of a variety of shapes that result in an initial buckling or bending along the reduced wall thickness region of the tube when the distal force DF and/or proximal force PF is applied to the proximal and distal ends of the tube 60 like that shown in FIG. 8A.

FIG. 9A shows the Nitinol tube 60 prior to the slots 61 being formed therein. The tube 60 is cut to form a cylindrical recess 76 in its outer cylindrical surface 75. Thereafter, the slots 61 are formed in the tube as shown in FIGS. 8A and 8B. FIG. 9B shows the tube 60 of FIG. 9A in a flattened state (as if the tube cut were along its length and laid flat on a surface) after the formation of the slots 61. As shown if FIG. 9B, each of the clot capturing elements 62 possesses a zone of reduced wall thickness 69. FIG. 9B shows an implementation wherein the recesses 76 formed in the clot capturing elements 62 have a rectangular profile and FIG. 9C shows an implementation wherein the recesses 76 formed in the clot capturing elements 62 have a curved profile such as, for example, a semi-circular profile or a U-shaped profile.

According to some implementations the zones of reduced wall thickness 69 are located nearer the distal end 66 of the slotted tube than to the proximal end 65 as shown in FIG. 9B.

According to some implementations the recess 76 is cut in the tube 60 to reduce the wall thickness of the tube in the recessed area by 5-30% and preferably by 10-20%.

In the implementations of FIGS. 8A-D and 9A-C the slots 61 are cut to form clot capturing elements 62 that are each arranged parallel to the longitudinal axis 77 of the tube 60 along their entire length. As will be disclosed in more detail below, the slots 61 may but cut to form clot capturing elements with different geometries and/or with different orientations.

FIGS. 10A-E illustrate a method for making a retrieval device according to another implementations. According to some implementations the method includes laser cutting a Nitinol tube 80 to form a plurality of circumferentially spaced-apart longitudinally slots 81. Formed between the slots 81 are a plurality of elongate clot capturing elements 82 that extend continuously (i.e. without any breaks or interruptions) along a substantial length of the tube 80. According to some implementations the clot capturing elements 82 have a length L2 that is greater than 50% the length L1 of the slotted tube 80. According to other implementations the clot capturing elements 82 have a length L2 that is greater than 70% of the length L1 of the slotted tube 80. Each of the length distances L1 and L2 is a straight line distance that runs parallel to the longitudinal axis 145 of tube 80.

The proximal ends 86 of the slots 81 are spaced a distance away from the proximal end 83 of the tube 80 and the distal ends 87 of the slots 81 are spaced a distance away from the distal end 84 of the tube 80 to respectively form the proximal and distal collars 22 and 21. FIG. 10B shows the slotted tube 80 of FIG. 10A as if it were cut along its length and laid flat on a surface.

As discussed above, the slots 81 are cut to form between them the plurality of clot capturing elements 82. The entirety of the lengths of slots 81 are not cut in a singular straight path. Instead, each slot is cut to produce clot capturing elements 82 having a straight proximal section 82a and a straight distal section 82b that are circumferentially offset from one another. According to some implementations, as shown in FIG. 10B, the clot capturing elements 82 include an inflection 85 that connects the distal ends of the straight proximal sections 82a to the proximal ends of the straight distal sections 82b. According to some implementations the inflections 85 comprise straight segments arranged at an angle with respect to each of proximal and distal sections 82a and 82b of the clot capturing elements 82 as shown in FIG. 10B. According to other implementations the inflections 85 comprise curved segments that may bend in a clockwise or counter-clockwise direction. The slots 81, clot capturing elements 82 and inflections 85 are configured and arranged such that when a distal force DF is applied to the proximal collar 22 and/or a proximal force PF is applied to the distal collar 21, the tube 80 begins to bulge at or around the location of the inflections 85 as shown in FIG. 10C. According to some implementations, the inflections 85 are configured to cause the proximal collar 22 to rotate with respect to the distal collar 21 (such as when the inflections 85 helically bend) as the proximal and distal collars are moved nearer to one another as shown in FIG. 10D.

As shown in FIG. 10D, as the distal force DF and/or proximal force PF continues to be applied to the tube, an inversion of the clot capturing elements 82 occurs within a proximal end portion of the tube while at the same time each of the clot capturing elements 82 continue to bend to assume an arched configuration as shown in FIG. 10E. If necessary, one or both of the distal and proximal collars 21 and 22 may be rotated with respect to the other during or after the inversion process so that the clot capturing elements assume their arched configurations with adjacent arches 74 preferably overlapping one another as shown in FIG. 10E. Alternatively or in conjunction with the aforesaid shaping method, the clot capturing elements 82 may be constrained in their desired expanded rest state using a specially designed fixture. When the clot capturing elements 82 and collars 21 and 22 are properly oriented with respect to one another, the unit is heat treated to shape-set the resultant retrieval device in its expanded rest state. According to some implementations the length of the resultant retrieval device 20 in its expanded rest state is 50% to 70% the pre-inversion length of the tube 80.

According to some implementations zones of reduced wall thickness, like those discussed above, may be formed along a section of the clot capturing elements 82 to assist in inducing the proximal end portion of the tube 80 to invert. According to some implementations, each of the inflections 85 is provided with a zone of reduced wall thickness. In such instances, the zone of reduced wall thickness may span the entire length of the inflections or less than the entire length. In the latter case, the zone of reduced wall thickness may be located within a mid-section, proximal end section or distal end section of the inflection.

Figure 12:
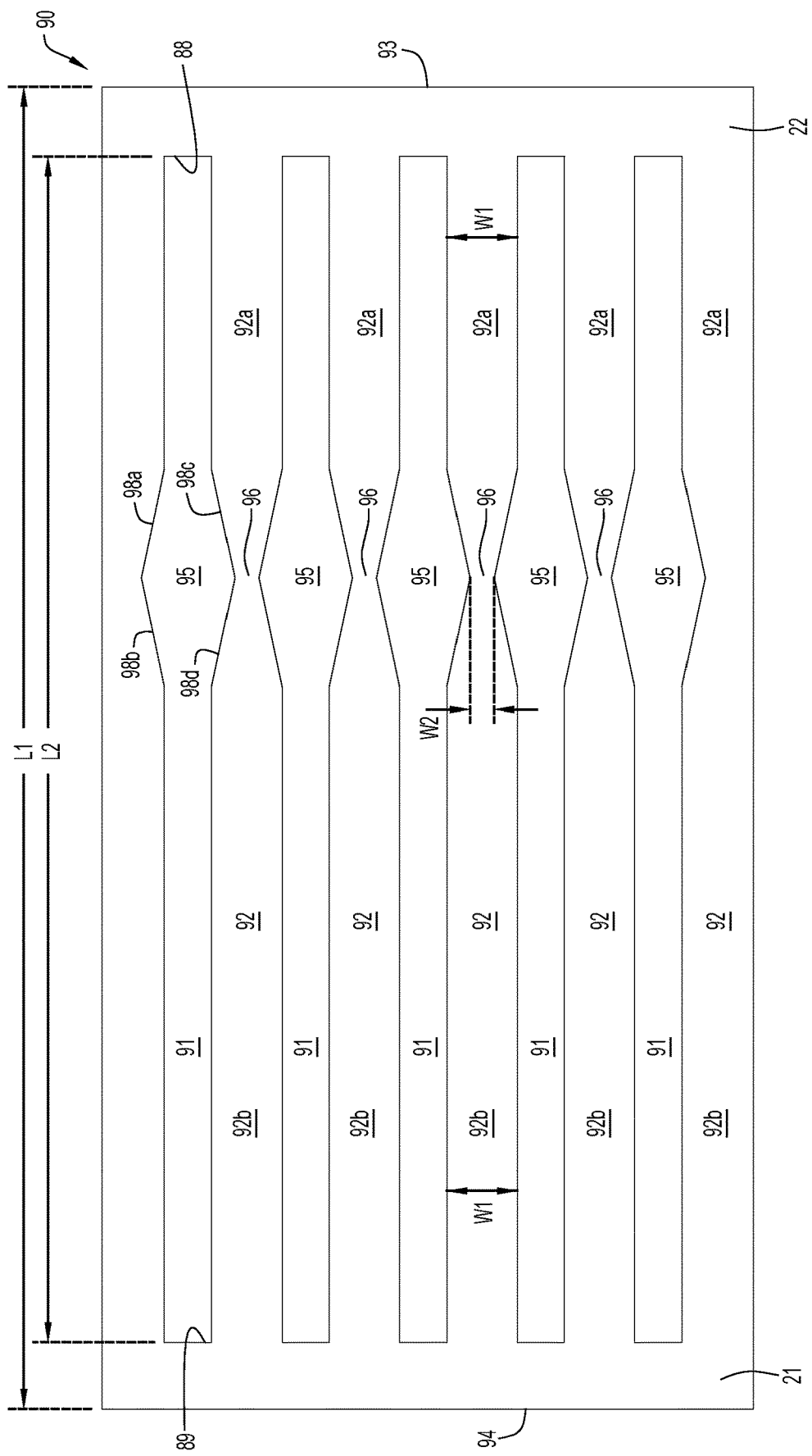
FIG. 12 shows a tubular member that is cut and laid flat on a surface from which a retrieval device may be made.

FIG. 12 depicts a Nitinol tube 90 that has been cut and laid flat on a surface. The tube 90 has a length L1 and includes a plurality of circumferentially spaced-apart longitudinally slots 91 that are cut into the tube 90 to form a plurality of elongate clot capturing elements 92 that extend continuously along a substantial length of the tube 90. According to some implementations the clot capturing elements have a length L2 that is greater than 50% of the length L1 of the slotted tube 90. According to other implementations the clot capturing elements have a length L2 that is greater than 70% of the length L1 of the slotted tube 90. The proximal ends 88 of slots 91 are spaced a distance away from the proximal end 93 of the tube 90 and the distal ends 89 of slots 91 are spaced a distance away from the distal end 94 of the tube 90 to respectively form the proximal and distal collars 22 and 21.

In the example of FIG. 12, each of the slots 91 respectively includes a flared portion 95 that creates in each of the clot capturing elements 92 a zone of reduced width 96. On each side of the zones of reduced width 96 the clot capturing elements 92 include a proximal section 92a and a distal section 92b that in the embodiment of FIG. 12 have a same width W1. In the example of FIG. 12 each of the zones of reduced width 96 comprises an area of minimum width W2 located in a mid-section thereof. According to some implementations width W2 is 5-25% less than width W1.

According to some implementations the proximal and distal sections 92a and 92b of the clot capturing elements 92 have different widths, with the width of the distal section 92b being greater than the width of the proximal section 2. According to some implementations the width of one or both of the proximal and distal sections 92a and 92b may vary along their lengths with the proximal section having a maximum width dimension along its length and the proximal section having a maximum width dimension along its length with the maximum width dimension of the distal section 92b being greater than the maximum width dimension of the proximal section 92a.

The slots 91, clot capturing elements 92 and zones of reduced width 96 are configured and arranged such that when a distal force DF is applied to the proximal collar 22 and/or a proximal force PF is applied to the distal collar 21, the tube 90 begins to bulge at or around the location of the zones of reduced width 96 to assist in facilitating an inversion of the clot capturing elements within a proximal end portion of the tube 90. According to other implementations, one or both of the first and second sections 92a and 92b of the clot capturing elements are not arranged parallel to the longitudinal axis of the tube 90 but may instead be curved (e.g. arranged in a helical pattern) about the longitudinal axis of the tube 90 as shown in FIGS. 15A-17B below.

In the example of FIG. 12 the width of the flared portions varies along its length in a linear fashion as a result of the flared portions being bound by ramped straight wall segments 98a, 98b, 98c and 98d. According to other implementations the flared portions are bound by curved wall segments that result in a non-linear width variation along the length of the flared portions. In the implementation of FIG. 12, proximal wall segments 98a and 98c diverge distally away from one another and distal wall segments 98b and 98d converge distally toward one another. According to some implementations the flared portion 95 of the slots 91 are shaped such that the resultant clot capturing elements 92 take the form of an hourglass along a portion of their lengths as shown in FIG. 12.

According to some implementations the zones of reduced width 96 of the clot capturing elements 92 are located nearer the proximal end 93 of the slotted tube 90 than to the distal end 94 as shown in FIG. 12. According to other implementations the zones of reduced width are located nearer the distal end 94 of the slotted tube 90 than to the proximal end 93.

As with the previously disclosed implementations, during or after an inversion of the proximal end portions 92a of the clot capturing elements 92 around the proximal collar 21, one or both of the distal collar 21 and proximal collar 22 may be rotated with respect to the other to cause a formation of a retrieval device similar to that depicted in FIGS. 8C and 8D.

Alternatively or in conjunction with the aforesaid shaping method, the clot capturing elements 92 may be constrained in their desired expanded rest state using a specially designed fixture. In any event, when the resultant retrieval device has been formed to assume its desired expanded rest state, the manufacturing process is followed by a defined heat treatment to shape-set the resultant clot retrieval device in its expanded rest state. According to some implementations the length of the resultant retrieval device in its expanded rest state is 50% to 70% the pre-inversion length of the tube 90.

Figure 13A:
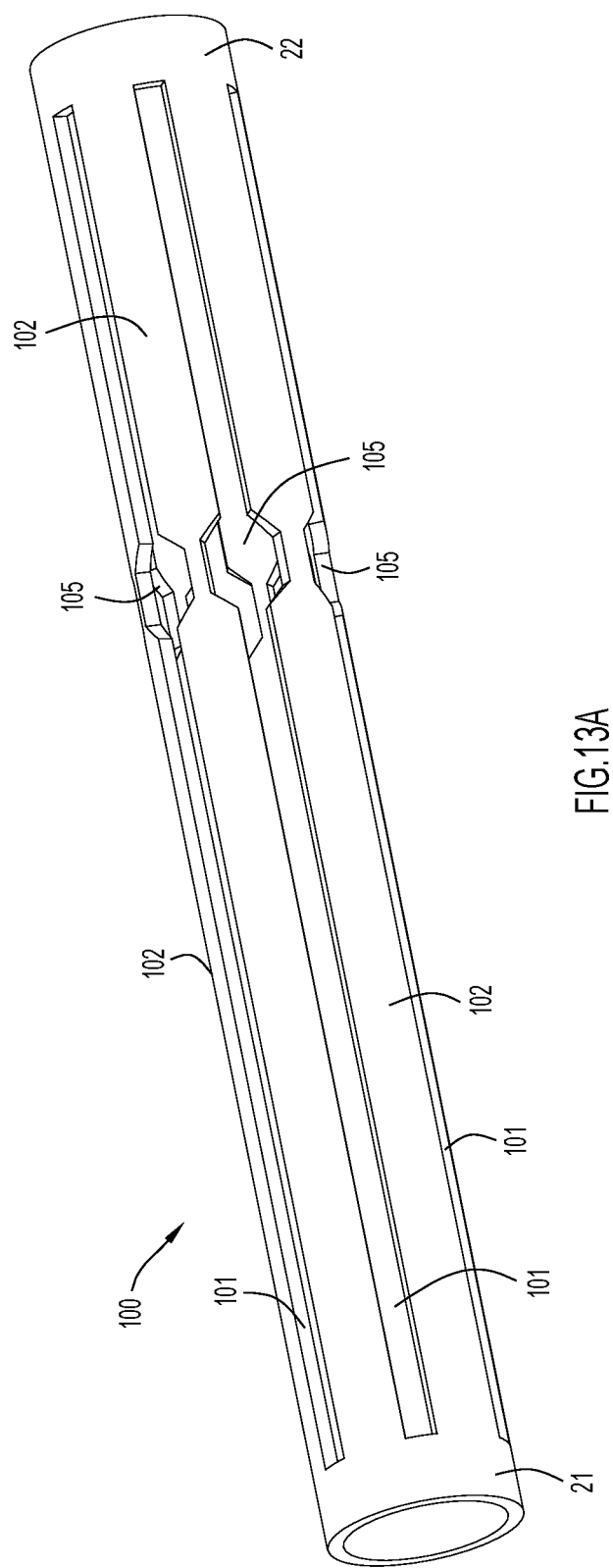
FIG. 13A illustrates a tubular member from which a retrieval device is unitarily made according to another implementation.
Figure 13B:
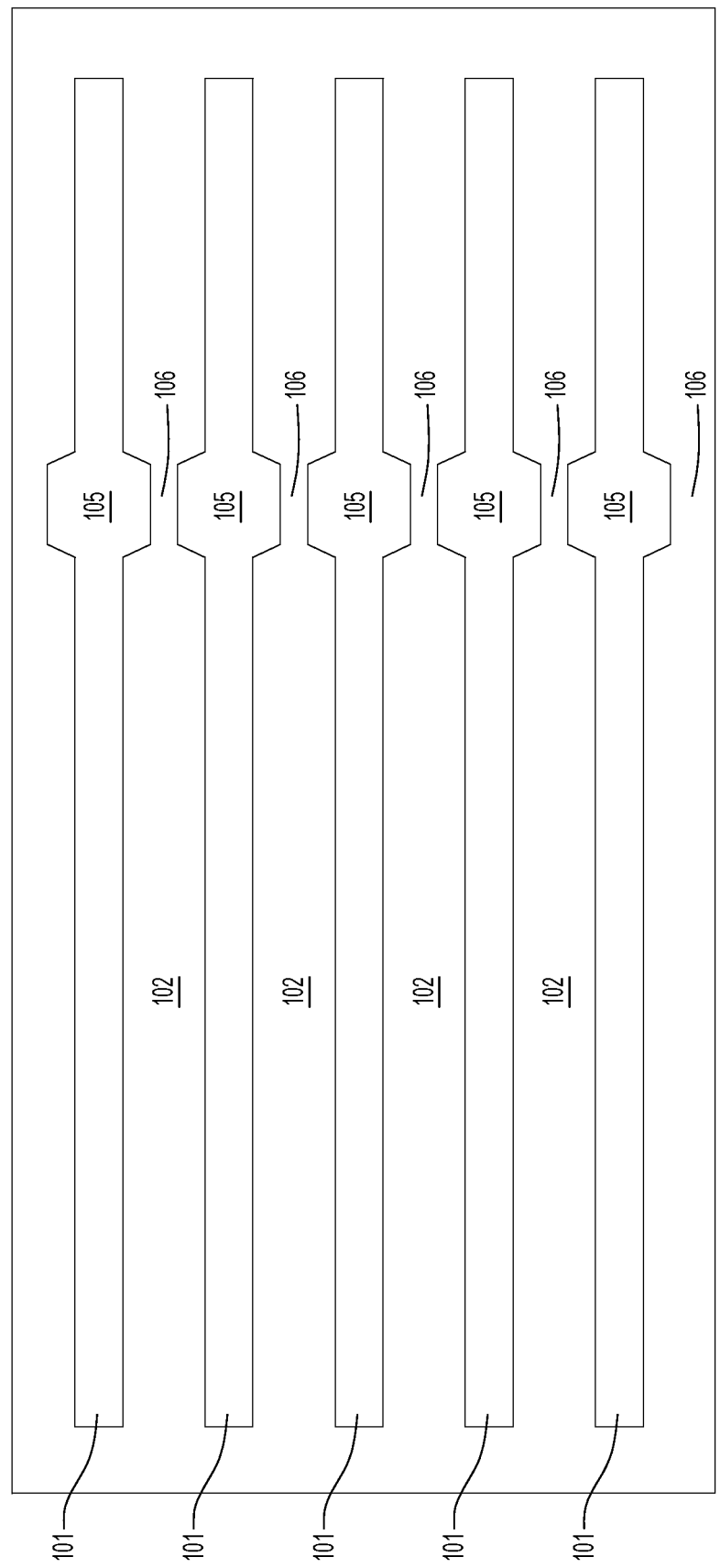
FIG. 13B shows the tubular member of FIG. 13A cut along its axial length and laid flat on a surface.

FIGS. 13A and 13B depict a variant of the slotted tube of FIG. 12. FIGS. 13A and 13B respectively show a slotted Nitinol tube 100 comprising a plurality of slots 101. Interposed between the slots 101 are clot capturing elements 102. FIG. 13A shows the tube 100 in its cylindrical configuration. FIG. 13B shows the slotted tube 100 as if it were cut along its length and laid flat on a surface. Like the example of FIG. 12, one or more or all of the slots 101 comprise flared portions 105 that result in the formation of zones of reduced width 106 along a portion of the length of the clot capturing elements 102. The flared portions 105 of FIGS. 13A-B differ from the flared portions 96 of FIG. 12 in both size and shape, being shorter in length and comprising a more rectangular shape.

Figure 14A:
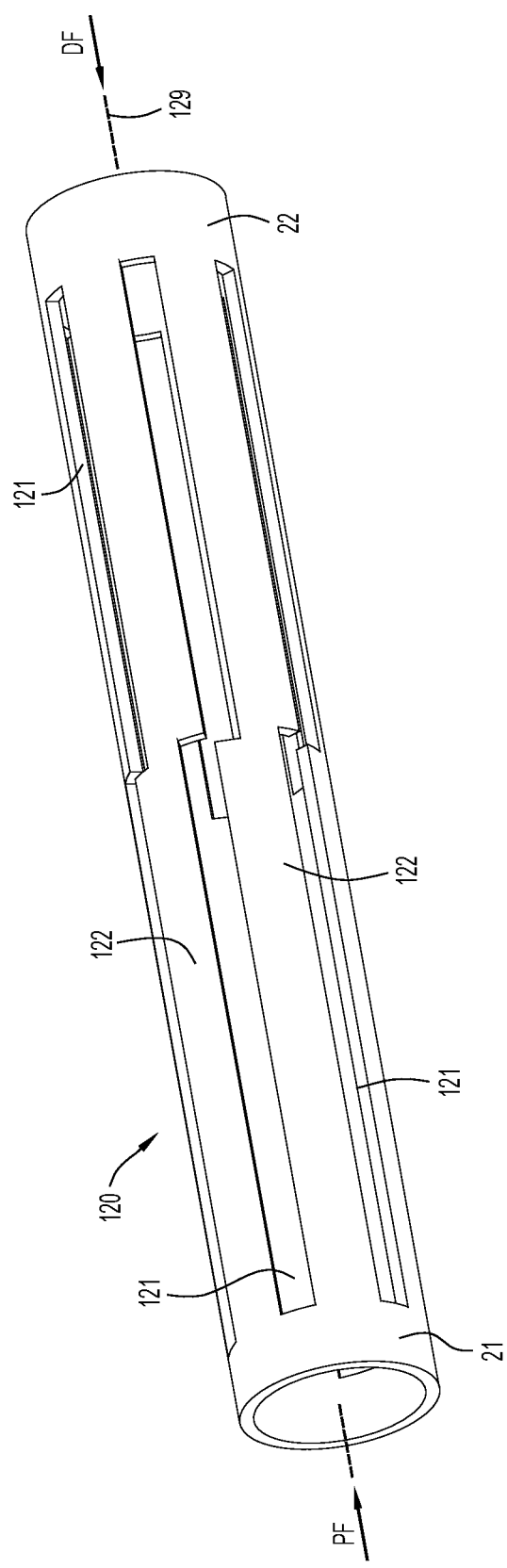
FIG. 14A illustrates a tubular member from which a retrieval device is unitarily made according to one implementation.
Figure 14B:
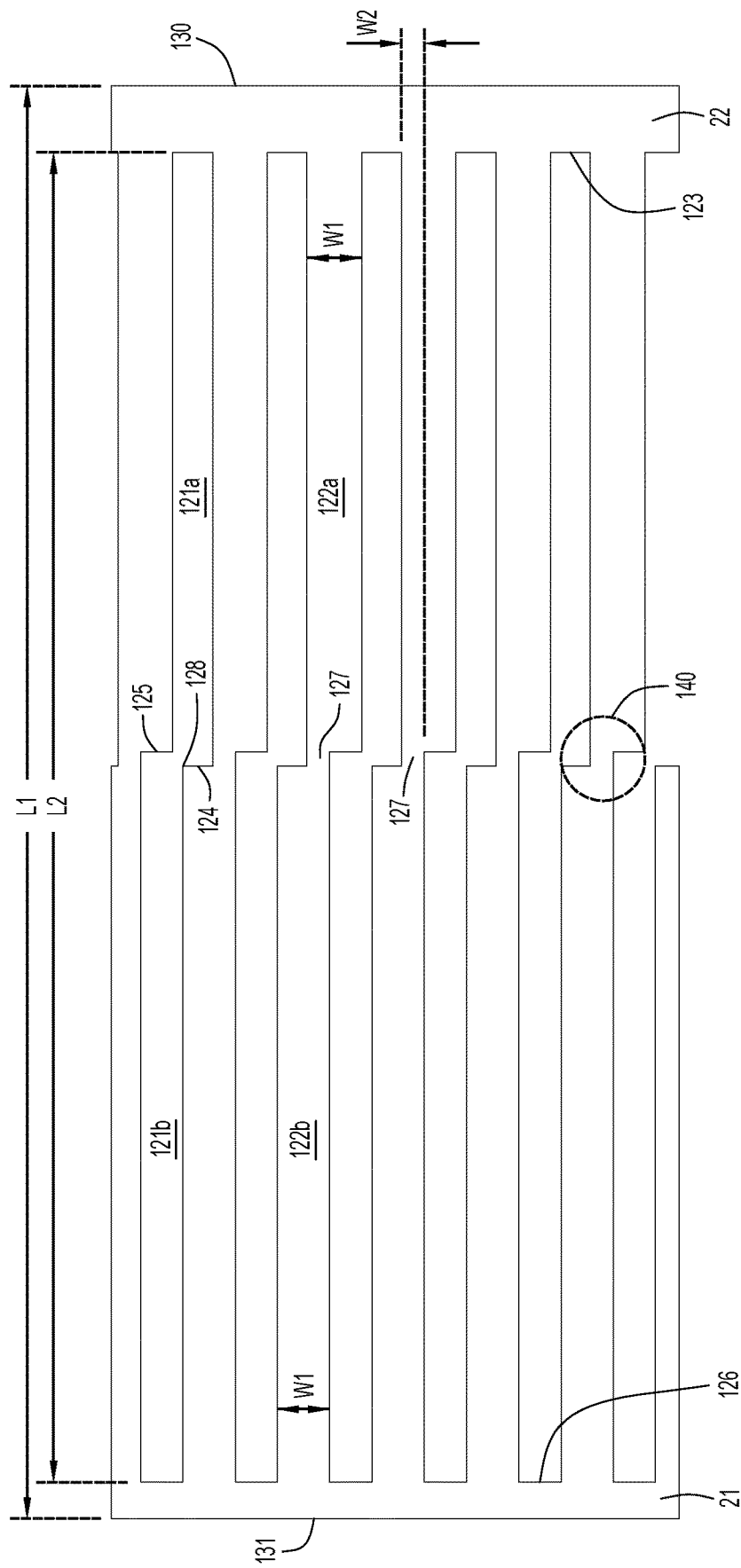
FIG. 14B shows the tubular member of FIG. 14A cut along its axial length and laid flat on a surface.

FIGS. 14A and 14B show a slotted Nitinol tube 120 used for making a retrieval device similar to those depicted in FIGS. 10D and 10E. FIG. 14A shows the tube 120 in its cylindrical configuration. FIG. 14B shows the tube 120 as if it were cut along its length and laid flat on a surface. The tube 120 has a length L1 between its proximal and distal ends 130 and 131.

The slotted tube 120 includes a plurality of circumferentially spaced-apart slots 121 that extend continuously across a substantial length of the tube 120. According to some implementations each of the slots 121 has a length L2 that is at least 50% the length L1 of the tube 120, and preferably a length L2 that is at least 70% the length of the tube 120. As shown in FIG. 12, each of the length distances L1 and L2 is a straight line distance that runs parallel to the longitudinal axis 129 of tube 120.

Each of the slots 121 includes a proximal segment 121a and a distal segment 121b that are circumferentially offset from one another and joined together at their respective overlapping distal and proximal ends 123 and 124 by a lateral passage 128. Circumferentially adjacent slots 121 form between them a clot capturing element 122 that includes circumferentially offset proximal and distal segments 122a and 122b of a first width W1 that are joined by a reduced width segment 127 having a width W2 that is less than the width W1. According to some implementations the width W2 is 5-50% the width W1 while according to other implementations the width W2 is 5-20% the width W1.

According to some implementations the reduced width segments 127 are located nearer the distal end 131 of the slotted tube 120 than to the proximal end 130.

The proximal end 123 of the slots 121 are spaced a distance away from the proximal end 130 of the tube 120 and the distal end 126 of the slots 121 are spaced a distance away from the distal end 131 of the tube 120 to respectively form the proximal and distal collars 22 and 21.

As shown in FIG. 14B, each of the clot capturing elements 122 includes a zone 140 in which the reduced width segment 127 coincides with a change of trajectory of the clot capturing element. As a result of the clot capturing element configurations, when an initial distal force DF is applied to the proximal collar 22 and/or an initial proximal force PF is applied to the distal collar 21, the tube 120 begins to bulge at or around the location of the zones 140.

As the distal force DF and/or proximal force PF continues to be applied to the tube 120, an inversion of the clot capturing elements 122 occurs within a proximal end portion of the tube similar to that shown in FIG. 10D. If necessary, during or after the inversion, one or both of the distal and proximal collars 21 and 22 may be rotated with respect to the other to cause the clot capturing elements 122 to assume a desired arched configuration with adjacent arches preferably overlapping one another as shown in FIG. 10E.

Alternatively or in conjunction with the aforesaid shaping method, the clot capturing elements 122 may be constrained in their desired expanded rest state using a specially designed fixture. In any event, when the resultant retrieval device has been formed to assume its desired expanded rest state, the manufacturing process is followed by a defined heat treatment to shape-set the resultant clot retrieval device in its expanded rest state. According to some implementations the length of the resultant retrieval device in its expanded rest state is 50% to 70% the pre-inversion length of the tube 120.

Figure 15A:
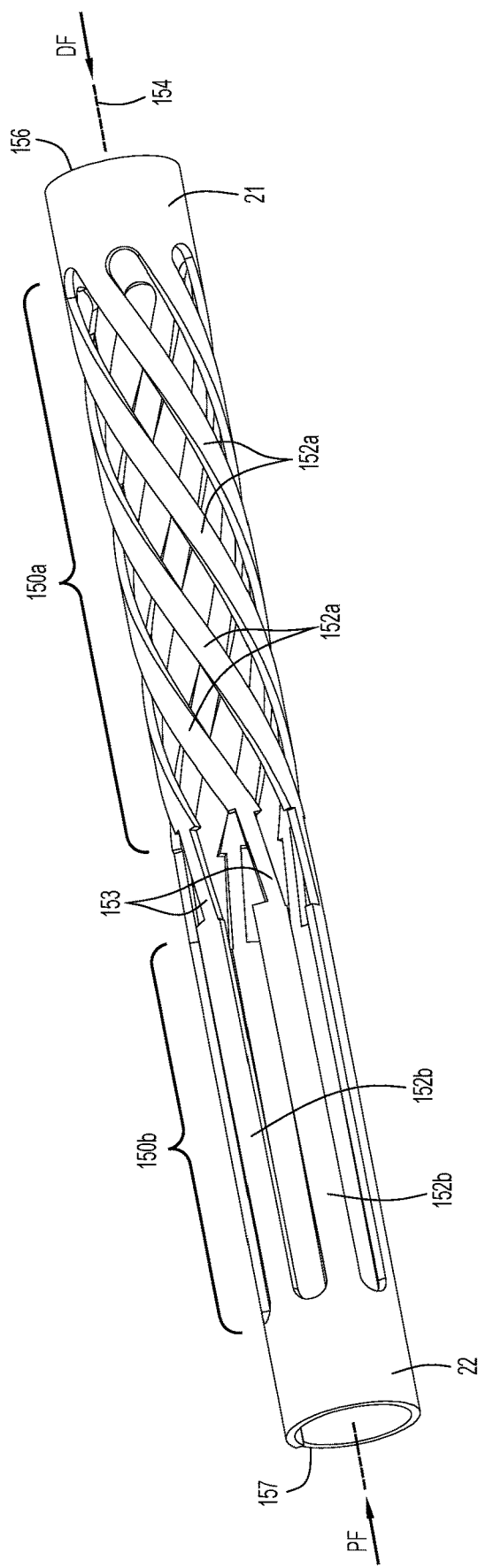
FIG. 15A illustrates a tubular member from which a retrieval device is unitarily made according to one implementation.
Figure 15B:
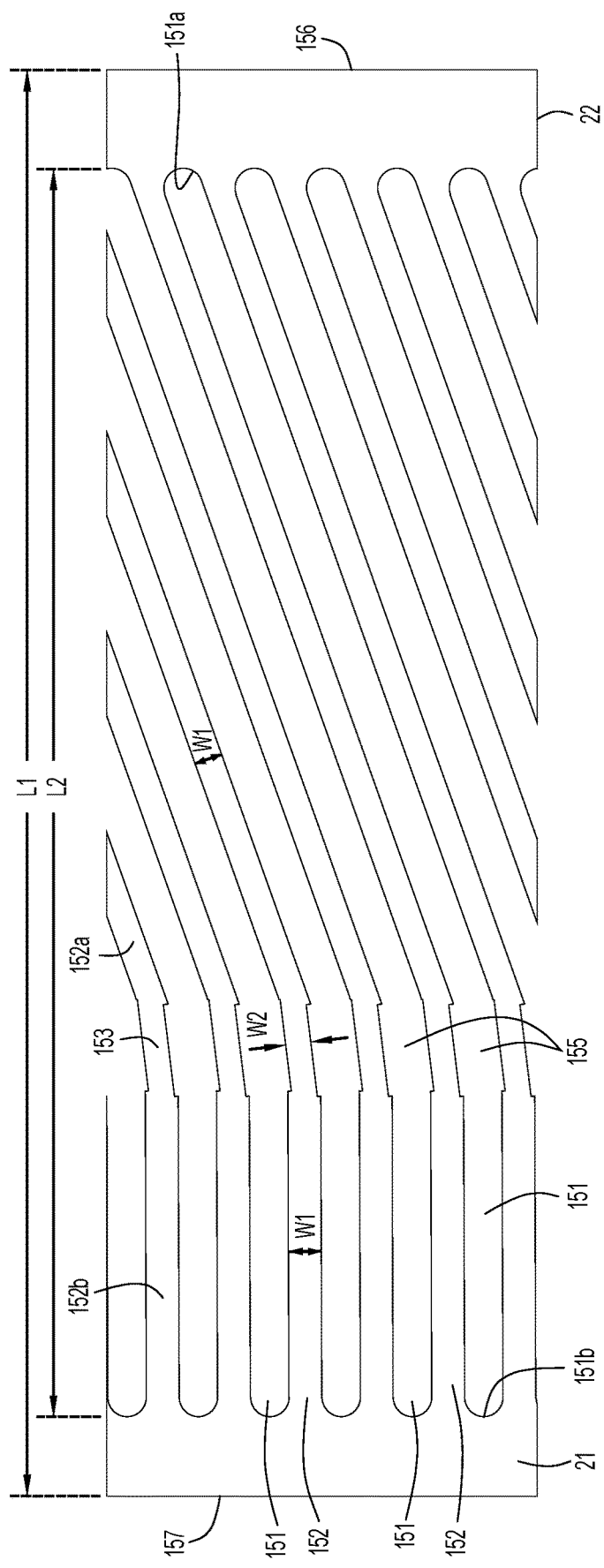
FIG. 15B shows the tubular member of FIG. 15A cut along its axial length and laid flat on a surface.

FIGS. 15A-B illustrate a slotted tube 150 from which a retrieval device like those depicted in FIGS. 10D and 10E may be made. FIG. 15A shows the slotted tube in its cylindrical configuration, FIG. 15B shows the tube 150 as if it has been cut along its length and laid flat on a surface. The tube has a length L1 between its proximal and distal ends 156 and 157.

Tube 150 includes a plurality of circumferentially spaced-apart slots 151 that form between them a plurality of circumferentially spaced-apart clot capturing elements 152. The tube 150 includes a proximal end portion 150a and a distal end portion 150b each having slots 151 cut therein to produce between circumferentially adjacent slots clot capturing elements 152. In the proximal end portion 150a of the tube 150 the clot capturing elements include a proximal end section 152a that curves around the longitudinal axis 154 of the tube 150 in, for example, a helical fashion. In the distal end portion 150b of the tube 150 the clot capturing elements include a distal end section 152b that is arranged substantially parallel to the longitudinal axis 154.

According to some implementations the slots 151 include a flared portion 155 that produces in the clot capturing elements 152 a zone of reduced width 153 that join the proximal and distal sections 152a and 152b. According to some implementations the zones of reduced width 153 are arranged non-parallel to the longitudinal axis 154 of the tube 150 and also non-parallel to each of the proximal and distal sections 152a and 152b of the clot capturing elements 152 as best seen in FIG. 15B.

According to some implementations the zones of reduced width 153 are located nearer the distal end 157 of the slotted tube 150 than to the proximal end 156.

According to some implementations, each of the helical proximal end section 152a and a straight distal end section 152b of the clot capturing elements 152 have a same first width W1 and the zone of reduced width 153 has a second width W2 that is less than the first width W1. According to some implementations the width W2 is 5-50% the width W1, while according to other implementations the width W2 is 5-20% the width W1.

Figure 15C:
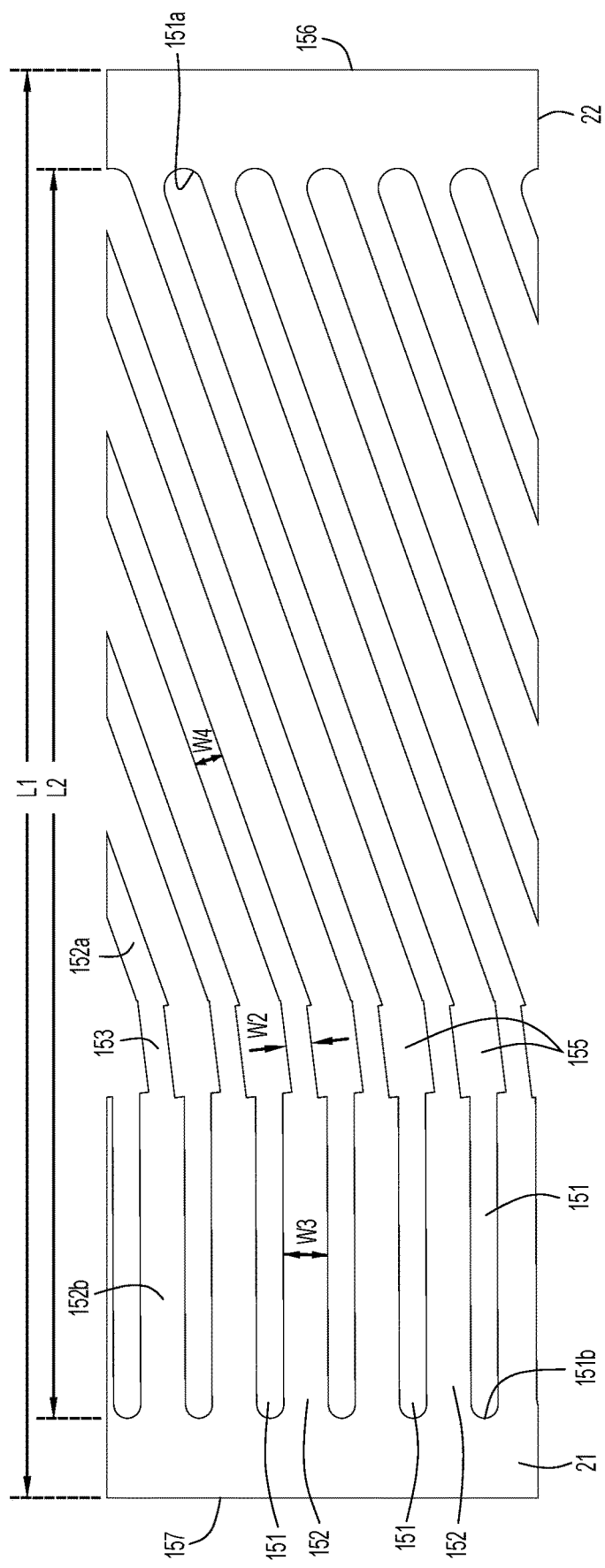
FIG. 15C shows the tubular member like that of FIG. 15B with the proximal and distal end sections of the clot capturing elements having different widths.

According to other implementations the slots 151 are cut such that the proximal and distal end sections 152a and 152b of the clot capturing elements 152 have different widths with the width W3 of the distal end sections 152b being greater than the width W4 of the proximal end sections 152a as shown in FIG. 15C. The provision of the distal end sections 152b having a greater width results in smaller gaps existing between them when the resultant retrieval device is in an expanded/deployed state. This advantageously impedes to a greater extent the passage of dislodged clot fragments across the retrieval device during a clot retrieval procedure.

With continued reference to FIGS. 15A-B, the slots 151 have proximal ends 151a that are spaced a distance away from the proximal end 156 of tube 150 in order to form the proximal collar 22. Likewise, the slots 151 have a distal end 151b that is spaced a distance away from the distal end 157 of tube 150 in order to form the distal collar 21. The length distance L2 between the proximal and distal ends 151a and 151b of the slot are thus less than the length L1 of the tube 150. Each of the length distances L1 and L2 is a straight line distance that runs parallel to the longitudinal axis 154 of tube 150. According to some implementations length L2 is at least 50% the length L1, and preferably at least 70% the length L1.

As disclosed above, according to some implementations the clot capturing elements 152 include a zone of reduced width 153 that coincides with a change of trajectory of the clot capturing elements. Due to such clot capturing element configurations, when an initial distal force DF is applied to the proximal collar 22 and/or an initial proximal force PF is applied to the distal collar 21, the tube 150 begins to bulge at or around the location of the zones of reduced width 153. By virtue of the helical nature of the proximal end section 152a of the clot capturing elements 152, as the distal and proximal collars 21 and 22 are brought closer together by the application of the proximal and/or distal forces, the proximal collar 22 rotates with respect to the distal collar 21.

As the distal force DF and/or proximal force PF continues to be applied to the tube 150, an inversion of the clot capturing elements 152 occurs at least within the proximal end portion 150a of the tube similar to what is shown in FIG. 10D, while at the same time each of the clot capturing elements 152 continues to bend to produce, for example, arched elements like those shown in FIG. 10D with adjacent arches preferably overlapping one another as shown in FIG. 10E.

Alternatively or in conjunction with the aforesaid shaping method, the clot capturing elements 152 may be constrained in their desired expanded rest state using a specially designed fixture. In any event, when the resultant retrieval device has been formed to assume its desired expanded rest state, the manufacturing process is followed by a defined heat treatment to shape-set the resultant clot retrieval device in its expanded rest state. According to some implementations the length of the resultant retrieval device in its expanded rest state is 50% to 70% the pre-inversion length of the tube 150.

Figure 16A:
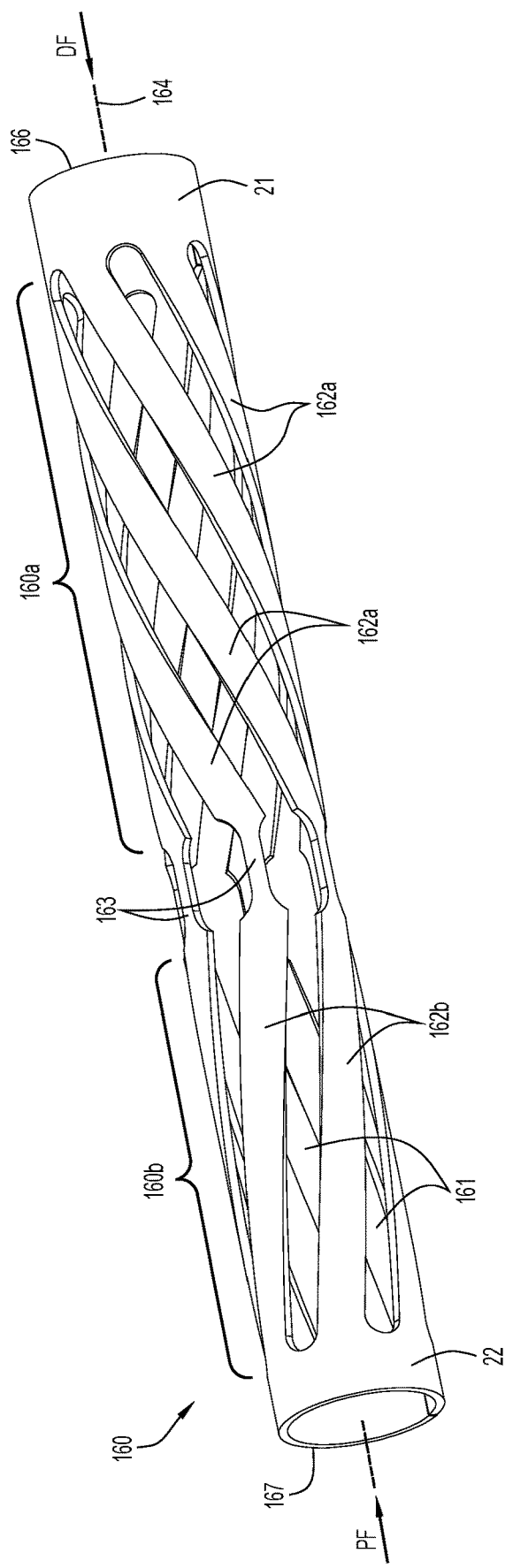
FIG. 16A illustrates a tubular member from which a retrieval device is unitarily made according to one implementation.

FIGS. 16A-B illustrate a slotted tube 160 from which a retrieval device like those depicted in FIGS. 10D and 10E may be made. FIG. 16A shows the slotted tube in its cylindrical configuration, FIG. 16B shows the tube 160 as if it has been cut along its length and laid flat on a surface. The tube has a length L1 between its proximal and distal ends 166 and 167.

Tube 160 includes a plurality of circumferentially spaced-apart slots 161 that form between them a plurality of circumferentially spaced-apart clot capturing elements 162. The tube 160 includes a proximal end portion 160a and a distal end portion 160b each having slots 161 cut therein to produce between circumferentially adjacent slots clot capturing elements 162. In the proximal end portion 160a of the tube 160 the clot capturing elements 162 include a proximal end section 162a that curves around the longitudinal axis 164 of the tube 160 in a first direction (e.g. counter clockwise direction) and a distal end section 162b that curves around the longitudinal axis 164 of the tube 160 in a second direction (e.g. clockwise direction) opposite the first direction.

According to some implementations the slots 161 include a flared portion 165 that produces in the clot capturing elements 162 a zone of reduced width 163 that join the proximal and distal sections 162a and 162b. According to some implementations the zones of reduced width 163 are arranged parallel to the longitudinal axis 164 of the tube 160.

According to some implementations the zones of reduced width 163 are located nearer the distal end 167 of the slotted tube 160 than to the proximal end 166.

According to some implementations, each of the proximal end section 162a and distal end section 162b of the clot capturing elements 162 have a same first width W1 and the zone of reduced width 163 has a second width W2 that is less than the first width W1. According to some implementations the width W2 is 5-50% the width W1, while according to other implementations the width W2 is 5-20% the width W1.

According to other implementations the slots 161 are cut such that the proximal and distal end sections 162a and 162b of the clot capturing elements 162 have different widths with the width of the distal end sections 162b being greater than the width of the proximal end sections 162a. The provision of distal end sections 162b having a greater width results in smaller gaps existing between them when the resultant retrieval device is in an expanded/deployed state. This advantageously impedes to a greater extent the passage of dislodged clot fragments across the retrieval device during a clot retrieval procedure.

With continued reference to FIGS. 16A-B, the slots 161 have proximal ends 161a that are spaced a distance away from the proximal end 166 of tube 160 in order to form the proximal collar 22. Likewise, the slots 161 have a distal end 161b that is spaced a distance away from the distal end 167 of tube 160 in order to form the distal collar 21. The length distance L2 between the proximal and distal ends 161a and 161b of the slot are thus less than the length L1 of the tube 160. Each of the length distances L1 and L2 is a straight line distance that runs parallel to the longitudinal axis 164 of tube 160. According to some implementations length L2 is at least 50% the length L1, and preferably at least 70% the length L1.

As disclosed above, according to some implementations the clot capturing elements 162 include a zone of reduced width 163 that coincides with a change of trajectory of the clot capturing elements. Due to such clot capturing element configurations, when an initial distal force DF is applied to the proximal collar 22 and/or an initial proximal force PF is applied to the distal collar 21, the tube 160 begins to bulge at or around the location of the zones of reduced width 163. By virtue of the curved nature of the proximal end section 162a of the clot capturing elements 162, as the distal and proximal collar 22 is brought axially closer to the distal collar 21, one or both of the proximal and distal collars 22 and 21 rotates with respect to the other.

As the distal force DF and/or proximal force PF continues to be applied to the tube 160, an inversion of the clot capturing elements 162 occurs at least within the proximal end portion 160a of the tube similar to what is shown in FIG. 10D, while at the same time each of the clot capturing elements 162 continues to bend to produce arched elements with adjacent arches preferably overlapping one another.

Alternatively or in conjunction with the aforesaid shaping method, the clot capturing elements 162 may be constrained in their desired expanded rest state using a specially designed fixture. In any event, when the resultant retrieval device has been formed to assume its desired expanded rest state, the manufacturing process is followed by a defined heat treatment to shape-set the resultant clot retrieval device in its expanded rest state. According to some implementations the length of the resultant retrieval device in its expanded rest state is 50% to 70% the pre-inversion length of the tube 160.

Figure 17A:
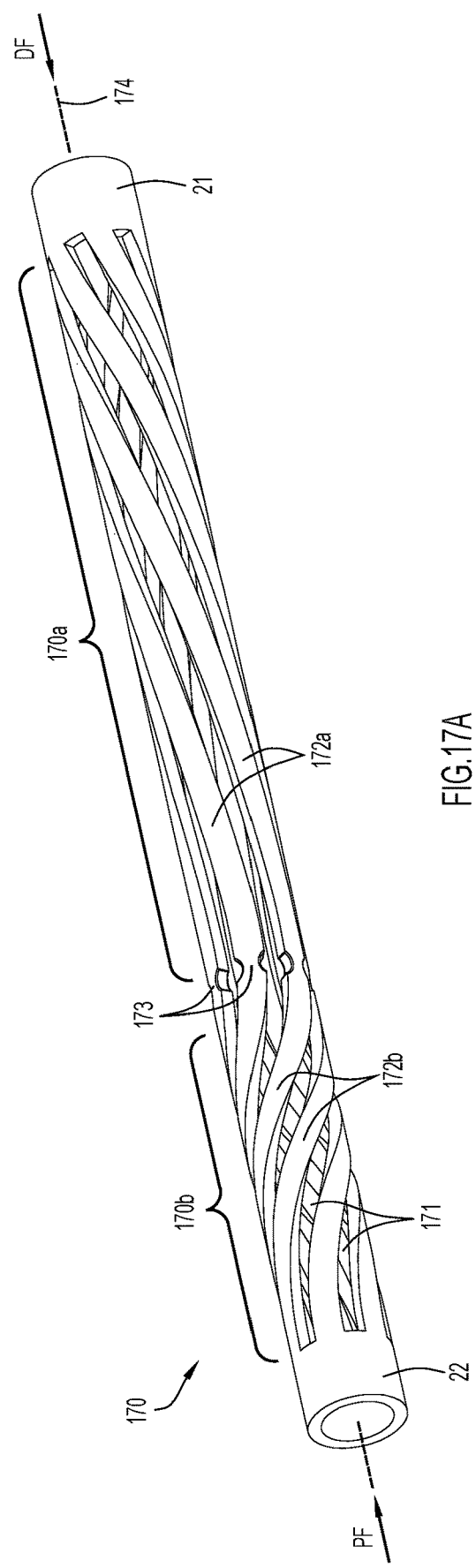
FIG. 17A illustrates a tubular member from which a retrieval device is unitarily made according to one implementation.

FIGS. 17A-B illustrate a slotted tube 170 from which a retrieval device like those depicted in FIGS. 10D and 10E may be made. FIG. 17A shows the slotted tube in its cylindrical configuration, FIG. 17B shows the tube 170 as if it has been cut along its length and laid flat on a surface. The tube has a length L1 between its proximal and distal ends 176 and 177.

Tube 170 includes a plurality of circumferentially spaced-apart slots 171 that form between them a plurality of circumferentially spaced-apart clot capturing elements 172. The tube 170 includes a proximal end portion 170a and a distal end portion 170b that each have slots 171 cut therein to produce between circumferentially adjacent slots the clot capturing elements 172. In the proximal end portion 170a of the tube 170 the clot capturing elements 172 include a curved proximal end section 172a as shown in FIG. 17B comprising a single bend. As also shown in FIG. 17B, in the distal end portion 170b of the tube 170 the clot capturing elements 172 include a curved distal end section 172b comprising multiple bends.

According to some implementations the slots 171 include flared portion 175 that produces in the clot capturing elements 172 a zone of reduced width 173 that joins the proximal and distal end sections 172a and 172b of the slots 172. According to some implementations the zones of reduced width 173 are located nearer the distal end 177 of the slotted tube 170 than to the proximal end 176.

According to some implementations, each of the proximal and distal end section 172a and 172b of the clot capturing elements 172 have a same first width W1 and the zone of reduced width 173 has a second width W2 that is less than the first width W1. According to some implementations the width W2 is 5-50% the width W1, while according to other implementations the width W2 is 5-20% the width W1.

According to other implementations the slots 171 are cut such that the proximal and distal end sections 172a and 172b of the clot capturing elements 172 have different widths with the width of the distal end sections 172b being greater than the width of the proximal end sections 172a. The provision of distal end sections 172b having a greater width results in smaller gaps existing between them when the resultant retrieval device is in an expanded/deployed state. This advantageously impedes to a greater extent the passage of dislodged clot fragments across the retrieval device during a clot retrieval procedure.

With continued reference to FIGS. 17A-B, the slots 171 have proximal ends 171a that are spaced a distance away from the proximal end 176 of tube 170 in order to form the proximal collar 22. Likewise, the slots 171 have a distal end 171b that is spaced a distance away from the distal end 177 of tube 170 in order to form the distal collar 21. The length distance L2 between the proximal and distal ends 171a and 171b of the slot are thus less than the length L1 of the tube 170. As shown in FIG. 17B, each of the length distances L1 and L2 is a straight line distance that runs parallel to the longitudinal axis 174 of tube 170. According to some implementations length L2 is at least 50% the length L1, and preferably at least 70% the length L1.

The zone of reduced width 163 in the clot capturing elements 172 coincides with a change of trajectory of the clot capturing elements as a result of being located in a curve of the clot capturing elements. Due to such clot capturing element configurations, when an initial distal force DF is applied to the proximal collar 22 and/or an initial proximal force PF is applied to the distal collar 21, the tube 170 begins to bulge at or around the location of the zones of reduced width 173. By virtue of the curved nature of the proximal end section 172a of the clot capturing elements 172, as the distal and proximal collars 21 and 22 are brought closer together by the application of the proximal and/or distal forces, one or both of the proximal and distal collars 22 and 21 rotate with respect to the other.

As the distal force DF and/or proximal force PF continues to be applied to the tube 170, an inversion of the clot capturing elements 172 occurs at least within the proximal end portion 170a of the tube similar to what is shown in FIG. 10D, while at the same time each of the clot capturing elements 172 continues to bend to produce arched elements with adjacent arches preferably overlapping one another. Alternatively or in conjunction with the aforesaid shaping method, the clot capturing elements 172 may be constrained in their desired expanded rest state using a specially designed fixture. In any event, when the resultant retrieval device has been formed to assume its desired expanded rest state, the manufacturing process is followed by a defined heat treatment to shape-set the resultant clot retrieval device in its expanded rest state. According to some implementations the length of the resultant retrieval device in its expanded rest state is 50% to 75% the pre-inversion length of the tube 170.

Figure 18A:
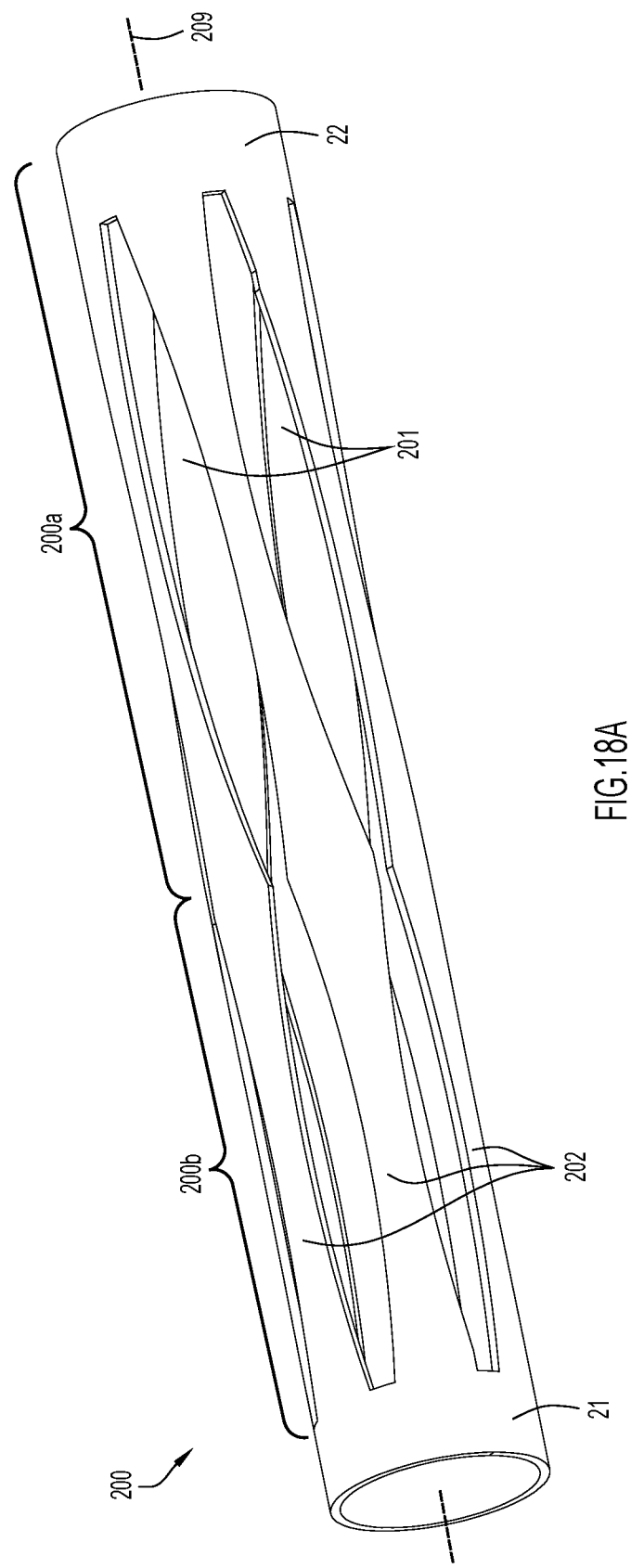
FIG. 18A illustrates a tubular member from which a retrieval device is unitarily made according to one implementation.

FIGS. 18A-B illustrate a slotted tube 200 from which a retrieval device like those depicted in FIGS. 10D and 10E may be made. FIG. 18A shows the slotted tube in its cylindrical configuration, FIG. 18B shows the tube 200 as if it has been cut along its length and laid flat on a surface. The tube has a length L1 between its proximal and distal ends 206 and 207.

Tube 200 includes a plurality of circumferentially spaced-apart slots 201 that form between them a plurality of circumferentially spaced-apart clot capturing elements 202. The tube 200 includes a proximal end portion 200a and a distal end portion 200b that each have slots 201 cut therein to produce between circumferentially adjacent slots the clot capturing elements 202. The slots 201 are cut such that their widths constantly vary along their length. As a result, the clot capturing elements 202 disposed between the slots 201 also have a constantly varying width along their lengths L2.

In the implementation of FIGS. 18A-B, the clot capturing elements 202 include a proximal end section 204 having a proximal end 204a and a distal end 204b. The clot capturing elements 202 also include a distal end section 205 having a distal end 205b and a proximal end 205a that coincides with the distal end 204b of the proximal end section 204. Each of the distal end sections 205 and distal end sections of the clot capturing elements are respectively defined by curved wall segments 204c, 204d and 205c, 205d. According to some implementations the curved wall segments are shaped so that the maximum width locations W1 of the proximal and distal sections 204 and 205 reside at each of their respective proximal and distal ends 204a/b and 205a/b. According to some implementations the curved wall segments are shaped to produce along the length of each of the proximal and distal end sections 204 and 205 a single minimum width location W2. According to some implementations the minimum width location W2 of each of the proximal and distal end sections 204 and 205 is disposed equidistantly between their respective proximal and distal ends 204a, 204b and 205a and 205b.

According to some implementations the width W2 is 30-90% the width W1, while according to other implementations the width W2 is 25-80% the width W1.

According to some implementations the distal end 204b of the proximal end section 204 of the clot capturing elements 202 meets with the proximal end 205a of the distal end section 205 at a point located nearer the distal end 208 of the tube 200 than to the proximal end 207 of the tube. According to other implementations the distal end 204b of the proximal end section 204 of the clot capturing elements 202 meets with the proximal end 205a of the distal end section 205 at a point located equidistantly between the proximal and distal ends 207 and 208 of tube 200.

With continued reference to FIGS. 18A-B, the slots 201 have proximal ends 201a that are spaced a distance away from the proximal end 207 of tube 200 in order to form the proximal collar 22. Likewise, the slots 201 have a distal end 201b that is spaced a distance away from the distal end 208 of tube 200 in order to form the distal collar 21. The length distance L2 between the proximal and distal ends 201a and 201b of the slots is thus less than the length L1 of the tube 200. As shown in FIG. 18B, each of the length distances L1 and L2 is a straight line distance that runs parallel to the longitudinal axis 209 of tube 200. According to some implementations length L2 is at least 50% the length L1, and preferably at least 70% the length L1.

Like with the slotted tube implementations disclosed above, the formation of a clot retrieval device similar in construction to those depicted in FIGS. 10D and 10E may be achieved by applying a distal force DF to the proximal collar 21 and/or proximal force PF to the distal collar 21 to induce an inversion of at least the proximal end sections 204 of the clot capturing elements 202. Also as disclosed above, during or after the inversion, one or both of the proximal and distal collars 22 and 21 may be rotated with respect to one another to cause the clot capturing elements 202 to achieve a desired arched configurations. Alternatively or in conjunction with the aforesaid shaping method, the clot capturing elements 202 may be constrained in their desired expanded rest state using a specially designed fixture. In any event, when the resultant retrieval device has been formed to assume its desired expanded rest state, the manufacturing process is followed by a defined heat treatment to shape-set the resultant clot retrieval device in its expanded rest state. According to some implementations the length of the resultant retrieval device in its expanded rest state is 50% to 75% the pre-inversion length of the tube 200.

Figure 20A:
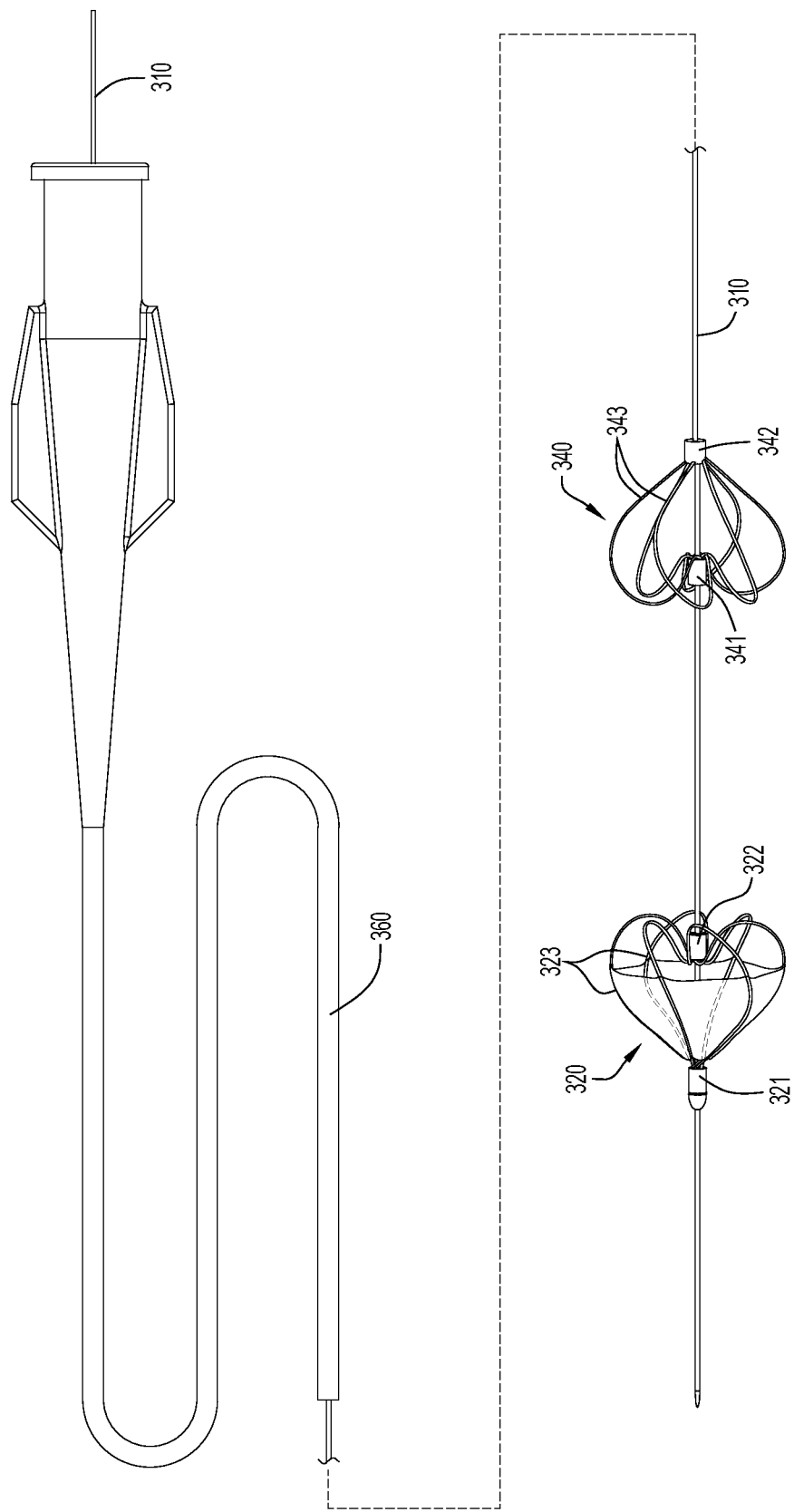
FIG. 20A illustrates an obstruction retrieval assembly having proximal and distal retrieval devices.
Figure 20C:
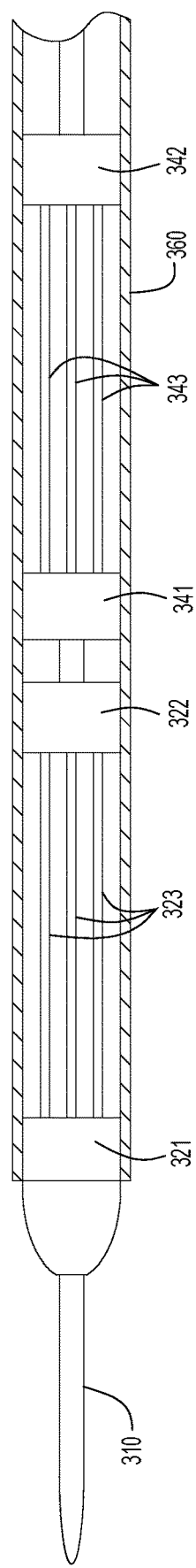
FIG. 20C is a cross-sectional side view of a distal end portion of the delivery catheter showing the proximal and distal retrieval devices in a radially constrained state inside the delivery catheter.

FIGS. 20A-C illustrate a clot retrieval assembly 300 that includes distal clot retrieval device 320 and a proximal clot retrieval device 340 mounted on an elongate wire 310. In use, the retrieval devices 320 and 340 are delivered to the site of an obstruction while being radially constrained inside a delivery catheter 360 as shown in FIG. 20C.

In some implementations distal retrieval device 320 includes a distal collar 321 fixed stationary to the elongate wire 310, and a proximal collar 322 that is slideable on the elongate wire 310. Extending between the proximal and distal collars are multiple shape memory elongate clot capturing elements 323 that are configured to engage the obstruction when the distal retrieval device 320 is in an expanded/deployed state as shown in FIGS. 20A and 20B. When the distal retrieval device 320 is an expanded/deployed state, the shape memory elongate clot capturing elements 323 assume a curved configuration that may be similar to or different than what is shown in FIGS. 20A and 20B.

In some implementations proximal retrieval device 340 includes a proximal collar 342 fixed stationary to the elongate wire 310, and a distal collar 341 that is slideable on the elongate wire 310. Extending between the proximal and distal collars 342 and 341 are multiple shape memory elongate clot capturing elements 343 that are configured to engage the obstruction when the proximal retrieval device 340 is in an expanded/deployed state as shown in FIGS. 20A and 20B. When proximal retrieval device 340 is an expanded/deployed state, the shape memory elongate clot capturing elements 343 assume a curved configuration similar to or different than what is shown in FIGS. 20A and 20B.

According to some implementations each of the distal and proximal retrieval devices 320 and 340 are constructed from a collection of independent parts like those depicted in FIGS. 4A-6. According to other implementations, each of the distal and proximal retrieval devices 320 and 340 are made from a slotted tube like those discussed above in conjunction with FIGS. 8A-18B.

When the distal retrieval device 320 is deployed from the delivery catheter 360 to assume an expanded state, it includes a proximal inverted portion 324 and a distal non-inverted portion 325. When the distal retrieval device 340 is deployed from the delivery catheter 360 to assume an expanded state, it includes a distal inverted portion 344 and a proximal non-inverted portion 345. As shown in FIG. 20A, according to some implementations the distal non-inverted portion 325 of the distal retrieval device 320 is provided with a permeable cover 327 made of a biocompatible material. The purpose of the permeable cover 327 is to capture fragments of the clot that may become dislodged during the clot retrieval process. According to some implementations the biocompatible material is encapsulated polytetrafluoroethylene (ePTFE) with a thickness of 0.0008 to 0.016 inches.

According to some implementations, when the distal retrieval device 320 is in its unconstrained expanded rest state, as shown in FIGS. 20A and 20B, the shape memory elongate clot capturing elements 323, as viewed from a proximal end of the distal retrieval device 320, form a plurality of arch structures like those shown in FIG. 7C and FIG. 8D, with adjoining arch structures preferably, but not necessarily, overlapping with one another.

According to some implementations, when the proximal retrieval device 340 is in its unconstrained expanded rest state, as shown in FIGS. 20A and 20B, the shape memory elongate clot capturing elements 343, as viewed from a distal end of the distal retrieval device 340, form a plurality of arch structures like those shown in FIG. 7C and FIG. 8D, with adjoining arch structures preferably, but not necessarily, overlapping with one another.

FIG. 20C is a side cross-sectional view of the distal end portion of the delivery catheter 360 showing the distal and proximal retrieval devices 320 and 340 radially constrained inside the delivery catheter. The distal retrieval device 320 functions like the retrieval device 20 discussed above in conjunction with the description of FIGS. 1A-3, being transitional between a radially constrained state, an expanded rest state, and an expanded stressed state. The proximal retrieval device 340 functions similar to the distal retrieval device 320, but in reversal.

According to some implementations, one or both of the distal collar 321 and proximal collar 322 of the distal retrieval device 320 and/or one or both of the distal collar 341 and proximal collar 342 of the proximal retrieval device 340 are made of a radiopaque material or are coated with a radiopaque material that enables their locations to be observed under fluoroscopy.

In use, the distal end portion of the delivery catheter 360 is delivered distal to the site of the clot over a guidewire like that shown in FIG. 19A. With the delivery catheter in place, the retrieval devices 320 and 340 are loaded in their radially constrained state into the delivery catheter 360 as shown in FIG. 20C. Thereafter, the distal and proximal retrieval devices are deployed distal to the clot by either withdrawing the delivery catheter in a proximal direction while holding the elongate wire 10 fixed or by holding the delivery catheter 30 fixed while distally advancing the elongate wire 10.

When in their deployed states inside the passageway of the patient, the arched structures of the retrieval devices 320 and 340 press against the arterial wall of the vessel. After the retrieval devices 320 and 340 are deployed, the elongate wire 310 to which the retrieval devices are attached is pulled proximally to first engage the proximal retrieval device 340 with the clot to entrap at least a portion of the clot between the clot capturing elements 343. After at least a portion of the clot is entrapped in the proximal retrieval device 340, the elongate wire 310 is further advanced proximally to engage the distal retrieval device 320 with any remaining portion of the clot. In some implementations the clot capturing elements 323 of the distal retrieval device 320 are configured to sweep along the arterial wall to which the clot is attached to cause the clot, or remnants of the clot, to be moved centrally towards the center of the affected vessel.

According to some implementations the distal collar 341 of the proximal retrieval device 340 and the proximal collar 322 of the distal retrieval device 320 move distally along the elongate wire 310 as the retrieval devices are pulled proximally through the clot. According to some implementations the proximal retrieval device 340 may be positioned proximal to the clot and pushed against or into the clot during the clot removal process. In such instances its distal collar 341 moves proximally along the elongate wire 310 as the retrieval device is pushed distally into the clot. As discussed above, the movement of the collars on the elongate wire during the clot capturing process stresses the clot capturing elements, enhancing their ability to entrap the clot.

Upon the clot being captured by one or both of the retrieval devices 320 and 340, removal of the clot may be accomplished, at least in part, by the elongate wire 10 being pulled proximally to move the clot to a mouth of an aspiration catheter or into the delivery catheter 360.

Figure 21:
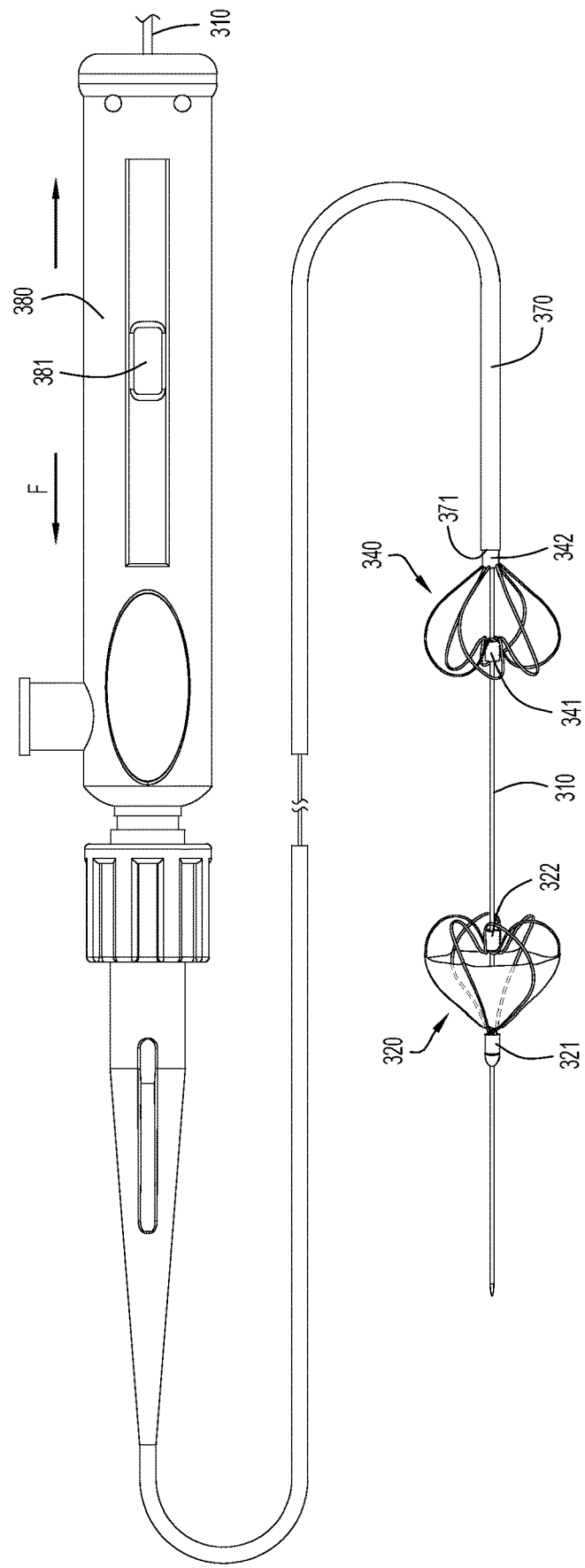
FIG. 21 illustrates an obstruction retrieval assembly according to another implementation wherein the proximal retrieval device is axially movable along a length of the elongate member.

FIG. 21 show a clot capturing assembly that includes distal and proximal retrieval devices 320 and 340 that may be made by any of a number of methods, including those disclosed above. The clot capturing assembly differs from the assembly of FIG. 20A-C in that the proximal retrieval device 340 is axially moveable along a length of the elongate wire 310 so that the distance that separates it from the distal retrieval device 320 may be varied. In all other respects the distal and proximal retrieval devices function as described above.

As with the implementations of FIGS. 20A-C, distal retrieval device 320 is mounted to the elongate wire 310 with its distal collar 321 fixed stationary to the elongate wire and its proximal collar 322 slideable on the elongate wire. On the other hand, the distal collar 341 and proximal collar 342 of the proximal retrieval device 340 are both slideable on the elongate wire 310 with the proximal collar 342 being fixed to a distal end 371 of an elongate hypotube 370 through which the elongate wire 310 passes. A proximal end portion of the hypotube 370 is attached to a sliding tab 381 located inside a user handle 380. The user handle 380 is configured such that when the handle is gripped by the user, the user's thumb may act on the sliding tab 381 to move the tab in a forward direction F or a rearward direction R. With the elongate wire 310 held stationary, when the tab 381 is moved in the forward direction F, the hypotube 370 is advanced distally to cause the proximal retrieval device 340 to move distally along the elongate wire 310 nearer the distal retrieval device 320. Conversely, when the tab 381 is moved in the rearward direction R, the hypotube 370 is advanced proximally to cause the proximal retrieval device 340 to move proximally along the elongate wire 310 away from the distal retrieval device 320.

Figure 22:
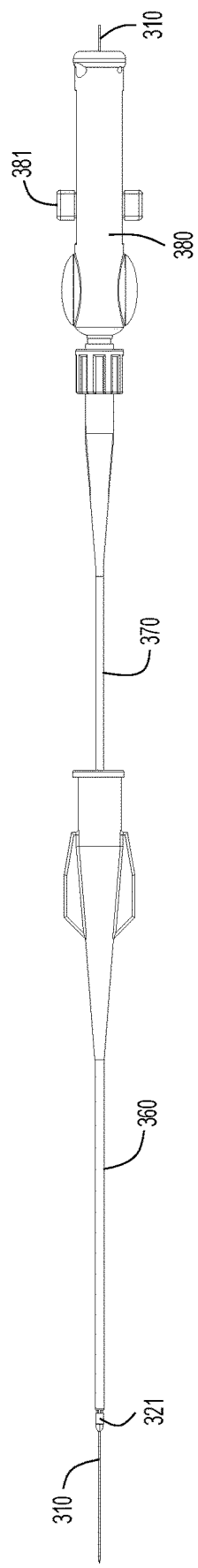
FIG. 22 is a side view of the obstruction retrieval assembly of FIG. 22 with the proximal and distal retrieval devices located inside the delivery catheter.
Figure 23:
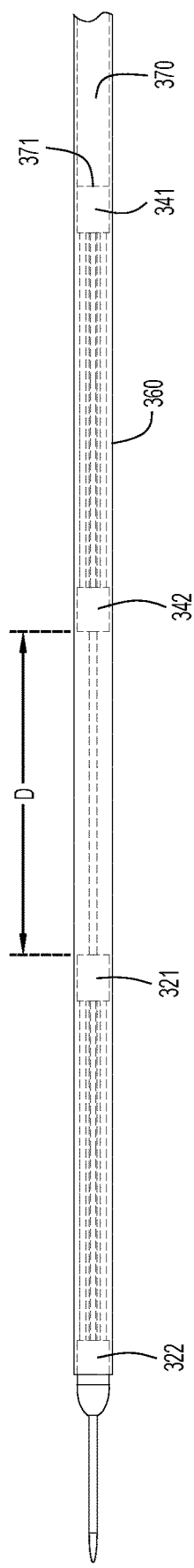
FIG. 23 is a cross-sectional side view of a distal end portion of the delivery catheter of FIG. 22 showing the proximal and distal retrieval devices in a radially constrained state inside the delivery catheter.
Figure 24:
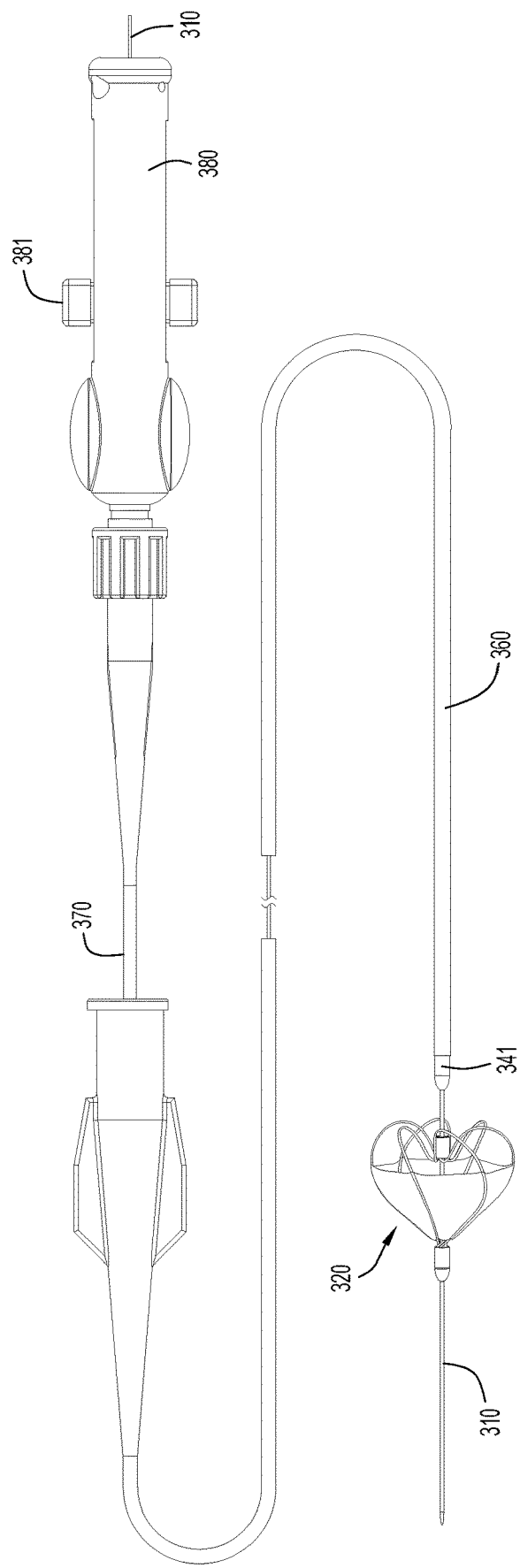
FIG. 24 shows the distal retrieval device after being deployed from the delivery catheter.
Figure 25A:
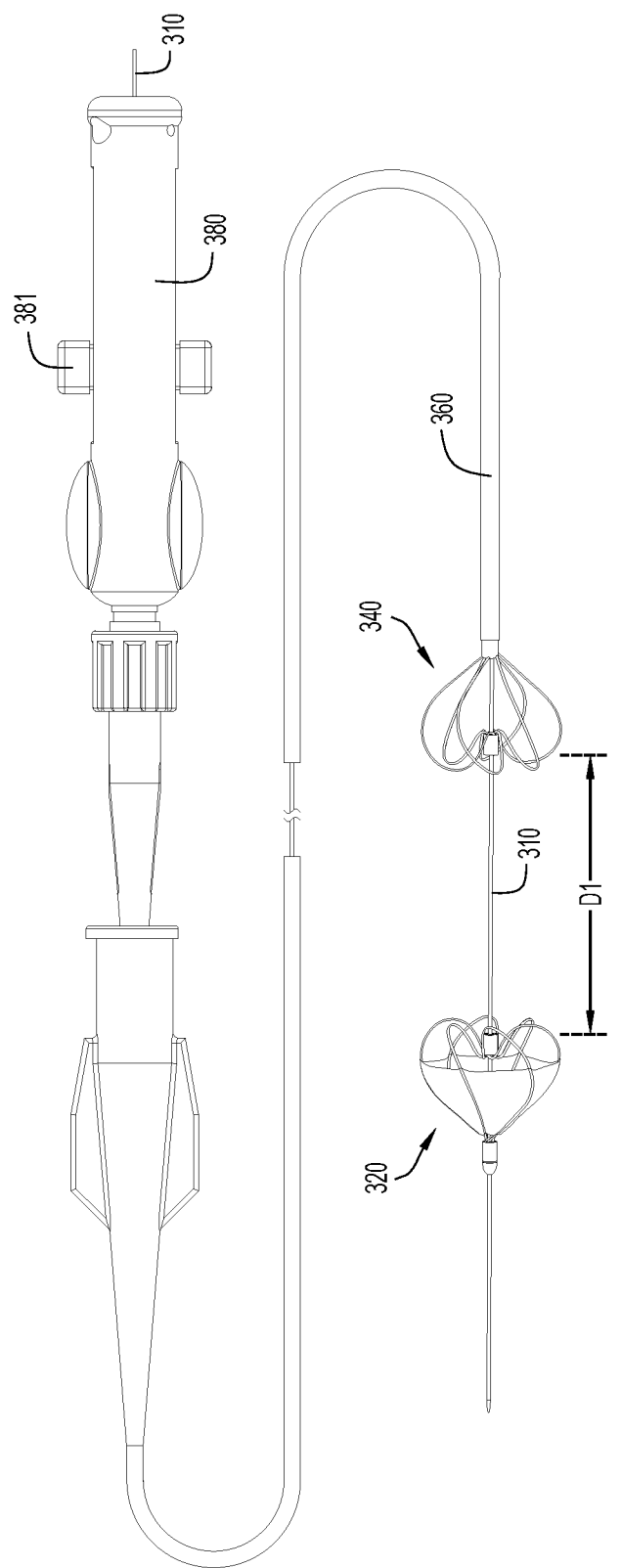
FIG. 25A shows the proximal and distal retrieval devices after being deployed from the delivery catheter with the proximal retrieval device spaced a first distance apart from the distal retrieval device.

The retrieval devices 320 and 340 are typically delivered to the site of the clot through a previously placed delivery catheter 360. FIG. 22 shows a side view and FIG. 23 shows a cross-sectional side view of the retrieval devices 320 and 340 radially constrained inside the lumen of the delivery catheter 360. When the sliding tab 381 of the user handle 380 is in a center position as shown in FIG. 21, the distal and proximal retrieval devices 320 and 340 are separated inside the lumen of the delivery catheter 360 by a distance D. Prior to deploying one or both of the retrieval devices 320 and 340 from the delivery catheter 360, the user may increase or decrease the distance D between them by respectively moving the sliding tab 381 in the rearward direction R or the forward direction F. Upon the proximal retrieval device 340 being placed in a desired position with respect to the distal retrieval device 320, the sliding tab 381 is locked in position to prevent any axial movement of the hypotube 370. Thereafter, the distal retrieval device 320 is deployed outside the delivery catheter 360 as shown in FIG. 24, and in some instances is followed by a deployment of the proximal retrieval device 340 outside the delivery catheter as shown in FIG. 25A. One or both of the retrieval device 320 and 340 may be deployed out the distal end of the delivery catheter 360 by either withdrawing the delivery catheter in a proximal direction while holding the elongate wire 310 fixed or by holding the delivery catheter fixed while distally advancing the elongate wire 310.

Figure 25B:
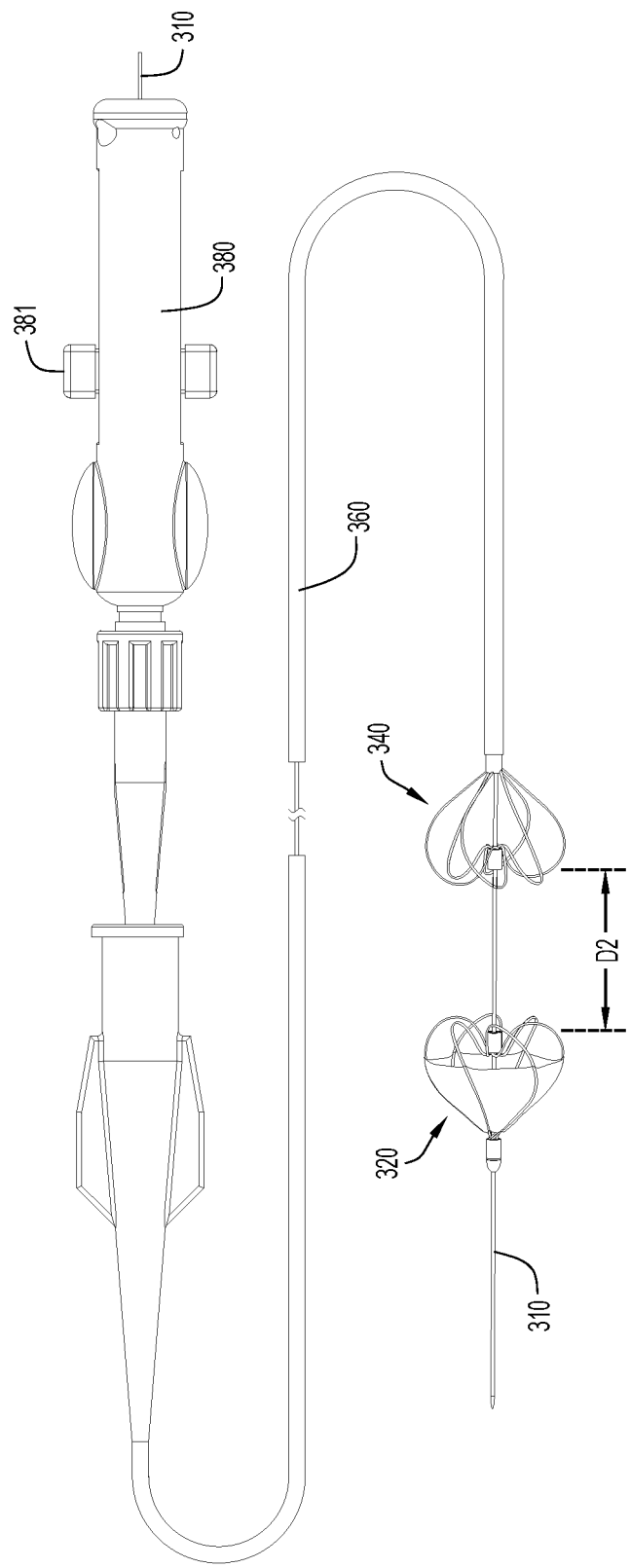
FIG. 25B shows the proximal and distal retrieval devices after being deployed from the delivery catheter with the proximal retrieval device spaced a second distance apart from the distal retrieval device, the second distance being less than the first distance.

FIG. 25A shows the distal and proximal retrieval devices 320 and 340 deployed outside the delivery catheter 360 and being separated by a first distance D1. FIG. 25B shows the distal and proximal retrieval devices 320 and 340 deployed outside the delivery catheter 360 and being separated by a second distance D2 that is less than the first distance.

According to some implementations the hypotube 170 has a length of about 180 centimeters and an inner diameter of between about 0.010 to 0.016 inches.

The following Group A-E clauses disclose in an unlimited way additional implementations.

Group A Clauses:

Clause 1. A clot retrieval assembly comprising:
an elongate wire having a length and a longitudinal axis;
a first retrieval device comprising:
  a distal collar fixed stationary on the elongate wire;
  a proximal collar being slideable along a portion of the length of the elongate wire; and
  a plurality of shape memory elongate clot capturing elements that each has a proximal end coupled to the proximal collar and a distal end coupled to the distal collar, each of the plurality of shape memory elongate capturing elements having a proximal end portion and a distal end portion;
the first retrieval device being configured to automatically transition from a radially constrained state to an expanded rest state, in the radially constrained state no portion of the plurality of shape memory elongate clot capturing elements is located proximal to the proximal collar and the proximal collar is located at a first axial position on the elongate wire proximal to the distal collar and is spaced apart from the distal collar by a first distance, in the expanded rest state the proximal collar is located at a second axial position on the elongate wire proximal to the distal collar and is spaced apart from the distal collar by a second distance that is less than the first distance and at least some of the proximal portions of the plurality of shape memory elongate clot capturing elements are inverted around the proximal collar with at least some of the proximal portions of the plurality of shape memory elongate clot capturing elements being disposed proximal to the proximal collar.

Clause 2. The clot retrieval assembly according to clause 1, wherein when the first retrieval device is in the expanded rest state the proximal collar is movable distally to a third axial position on the elongate wire proximal to the distal collar and is spaced apart from the distal collar by a third distance that is less than the second distance.

Clause 3. The clot retrieval assembly according to clause 2, wherein when the proximal collar of the first retrieval device is in the third axial position on the elongate wire, the first retrieval device is in an expanded stressed state.

Clause 4. The clot retrieval assembly according to clause 1, wherein when the first retrieval device is in the radially constrained state no portion of each of the plurality of shape memory elongate clot capturing elements bends back on itself.

Clause 5. The clot retrieval assembly according to any of the preceding clauses, wherein the second length is 30% to 60% the first length.

Clause 6. The clot retrieval assembly according to any of the preceding clauses, wherein when the first retrieval device is in the expanded rest state at least some of the plurality of shape memory elongate clot capturing elements take a zigzag path from the proximal collar to the distal collar with a first portion of the path extending in a proximal direction and a second portion of the path extending in a distal direction.

Clause 7. The clot retrieval assembly according to any of the preceding clauses, wherein when the first retrieval device in the expanded rest state the first retrieval device includes a proximal inverted portion where the shape memory elongated clot capturing elements are inverted around the proximal collar, and a distal non-inverted portion, the distal non-inverted portion being composed of distal end portions of the shape memory elongate clot capturing elements.

Clause 8. The clot retrieval assembly according to clause 2, wherein when the proximal collar is in the second axial position one or more of the shape memory elongate clot capturing elements has a first stiffness, and when the proximal collar is in the third axial position the one or more shape memory elongate clot capturing elements has a second stiffness greater than the first stiffness.

Clause 9. The clot retrieval assembly according to clause 7, wherein the distal non-inverted portion of the first retrieval device includes a permeable cover.

Clause 10. The clot retrieval assembly according to any of the preceding clauses, wherein each of the plurality of shape memory elongate clot capturing elements has a proximal end and a distal end that are respectively attached to the proximal and distal collars by an adhesive.

Clause 11. The clot retrieval assembly according to any of the preceding clauses, wherein each of the plurality of shape memory elongate clot capturing elements has a proximal end and a distal end that are respectively attached to the proximal and distal collars by a solder.

Clause 12. The clot retrieval assembly according to any of the preceding clauses, wherein each of the plurality of shape memory elongate clot capturing elements has a proximal end and a distal end that are respectively welded to the proximal and distal collars.

Clause 13. The clot retrieval assembly according to any of the preceding clauses, wherein the plurality of shape memory elongate clot capturing elements and the proximal and distal collars are formed from a single piece of material.

Clause 14. The clot retrieval assembly according to any of the preceding clauses, wherein the distal collar has an atraumatic distal tip.

Clause 15. The clot retrieval assembly according to any of the preceding clauses, further comprising:
 a second retrieval device located on the elongate wire distal to the first retrieval device, the second retrieval device comprising:
  a distal collar fixed stationary on the elongate wire;
  a proximal collar being slideable along a portion of the length of the elongate wire; and
  a plurality of shape memory elongate clot capturing elements that each has a proximal end coupled to the proximal collar of the second retrieval device and a distal end coupled to the distal collar of the second retrieval device, each of the plurality of shape memory elongate capturing elements having a proximal end portion and a distal end portion;
  the second retrieval device being configured to transition from a radially constrained state to an expanded rest state, in the radially constrained state the proximal collar of the second retrieval device is located at a first axial position on the elongate wire proximal to the distal collar of the second retrieval device and is spaced apart from the distal collar of the second retrieval device by a first distance, in the expanded rest state the proximal collar of the second retrieval device is located at a second axial position on the elongate wire proximal to the distal collar of the second retrieval device and is spaced apart from the distal collar of the second retrieval device by a second distance that is less than the first distance.

Clause 16. The clot retrieval assembly according to clause 15, wherein when the second retrieval device is in the radially constrained state no portion of the plurality of shape memory elongate clot capturing elements is located proximal to the proximal collar and when the second retrieval device is in the radially expanded state at least some of the proximal portions of the plurality of shape memory elongate clot capturing elements are inverted around the proximal collar with at least some of the proximal portions of the plurality of shape memory elongate clot capturing elements being disposed proximal to the proximal collar.

Clause 17. The clot retrieval assembly according to clauses 15 and 16, wherein when the second retrieval device is in the expanded rest state the proximal collar is movable distally to a third axial position on the elongate wire proximal to the distal collar and is spaced apart from the distal collar by a third distance that is less than the second distance.

Clause 18. The clot retrieval assembly according to clause 1, further comprising:
 a second retrieval device located on the elongate wire proximal to the first retrieval device, the second retrieval device comprising:
  a proximal collar fixed stationary on the elongate wire;
  a distal collar being slideable along a portion of the length of the elongate wire; and
  a plurality of shape memory elongate clot capturing elements that each has a proximal end coupled to the proximal collar of the second retrieval device and a distal end coupled to the distal collar of the second retrieval device, each of the plurality of shape memory elongate capturing elements having a proximal end portion and a distal end portion;
  the second retrieval device being configured to transition from a radially constrained state to an expanded rest state, in the radially constrained state the distal collar of the second retrieval device is located at a first axial position on the elongate wire proximal to the proximal collar of the second retrieval device and is spaced apart from the proximal collar of the second retrieval device by a first distance, in the expanded rest state the distal collar of the second retrieval device is located at a second axial position on the elongate wire distal to the proximal collar of the second retrieval device and is spaced apart from the proximal collar of the second retrieval device by a second distance that is less than the first distance.

Clause 19. The clot retrieval assembly according to clause 18, wherein when the second retrieval device is in the radially constrained state no portion of the plurality of shape memory elongate clot capturing elements is located distal to the distal collar and when the second retrieval device is in eh expanded rest state at least some of the distal portions of the plurality of shape memory elongate clot capturing elements are inverted around the distal collar with at least some of the distal portions of the plurality of shape memory elongate clot capturing elements being disposed distal to the distal collar.

Group B Clauses:

Clause 1. A clot retrieval assembly comprising:
 an elongate wire having a length and a longitudinal axis;
 a first retrieval device comprising:
  a distal collar fixed stationary on the elongate wire;
  a proximal collar being slideable along a portion of the length of the elongate wire; and
  a plurality of shape memory elongate clot capturing elements that each has a proximal end coupled to the proximal collar and a distal end coupled to the distal collar;

the first retrieval device being configured to transition from a radially constrained state to an expanded rest state and from the expanded rest state to an expanded stressed state, in the radially constrained state the proximal collar is located at a first axial position on the elongate wire proximal to the distal collar and is spaced apart from the distal collar by a first distance, in the expanded rest state the proximal collar is located at a second axial position on the elongate wire proximal to the distal collar and is spaced apart from the distal collar by a second distance that is less than the first distance, in the expanded stressed state the proximal collar is located at a third axial position on the elongate wire proximal to the distal collar and is spaced apart from the distal collar by a third distance that is less than the second distance.

Clause 2. The clot retrieval assembly according to clause 1, wherein when the first retrieval device is in the radially constrained state no portion of each of the plurality of shape memory elongate clot capturing elements bends back on itself.

Clause 3. The clot retrieval assembly according to clause 1, wherein when the first retrieval device is in the radially constrained state no portion of the plurality of shape memory elongate clot capturing elements is located proximal to the proximal collar.

Clause 4. The clot retrieval assembly according to any of the preceding clauses, wherein the second length is 30% to 60% the first length.

Clause 5. The clot retrieval assembly according to any of the preceding clauses, wherein when the first retrieval device is in the expanded rest state at least portions of some of the plurality of shape memory elongate clot capturing elements extend proximal to the proximal collar.

Clause 6. The clot retrieval assembly according to any of the preceding clauses, wherein when the first retrieval device is in the expanded rest state at least some of the plurality of shape memory elongate clot capturing elements take a path from the proximal collar to the distal collar with a first portion of the path extending in a proximal direction and a second portion of the path extending in a distal direction.

Clause 7. The clot retrieval assembly according to clause 1, wherein when the first retrieval device in the expanded rest state the first retrieval device includes a proximal inverted portion and a distal non-inverted portion, the proximal inverted portion being composed of proximal end portions of the shape memory elongate clot capturing elements, the distal non-inverted portion being composed of distal end portions of the shape memory elongate clot capturing elements.

Clause 8. The clot retrieval assembly according to clause 7, wherein the proximal inverted portion does not exists when the first retrieval device is in the radially constrained state.

Clause 9. The clot retrieval assembly according to any of the preceding clauses, wherein when the proximal collar is in the second axial position one or more of the shape memory elongate clot capturing elements has a first stiffness, and when the proximal collar is in the third axial position the one or more shape memory elongate clot capturing elements has a second stiffness greater than the first stiffness.

Clause 10. The clot retrieval assembly according to clause 7, wherein the distal non-inverted portion of the first retrieval device includes a permeable cover.

Clause 11. The clot retrieval assembly according to any of the preceding clauses, wherein each of the plurality of shape memory elongate clot capturing elements has a proximal end and a distal end that are respectively attached to the proximal and distal collars by an adhesive.

Clause 12. The clot retrieval assembly according to any of the preceding clauses, wherein each of the plurality of shape memory elongate clot capturing elements has a proximal end and a distal end that are respectively attached to the proximal and distal collars by a solder.

Clause 13. The clot retrieval assembly according to any of the preceding clauses, wherein each of the plurality of shape memory elongate clot capturing elements has a proximal end and a distal end that are respectively welded to the proximal and distal collars.

Clause 14. The clot retrieval assembly according to any of the preceding clauses, wherein plurality of the shape memory elongate clot capturing elements and the proximal and distal collars are formed from a single piece of material.

Clause 15. The clot retrieval assembly according to any of the preceding clauses, wherein the distal collar has an atraumatic distal tip.

Clause 16. The clot retrieval assembly according to clause 1, further comprising:
a second retrieval device located on the elongate wire distal to the first retrieval device, the second retrieval device comprising:
a distal collar fixed stationary on the elongate wire;
a proximal collar being slideable along a portion of the length of the elongate wire; and
a plurality of shape memory elongate clot capturing elements that each has a proximal end coupled to the proximal collar of the second retrieval device and a distal end coupled to the distal collar of the second retrieval device;
the second retrieval device being configured to transition from a radially constrained state to an expanded rest state, in the radially constrained state the proximal collar of the second retrieval device is located at a first axial position on the elongate wire proximal to the distal collar of the second retrieval device and is spaced apart from the distal collar of the second retrieval device by a first distance, in the expanded rest state the proximal collar of the second retrieval device is located at a second axial position on the elongate wire proximal to the distal collar of the second retrieval device and is spaced apart from the distal collar of the second retrieval device by a second distance that is less than the first distance.

Clause 17. The clot retrieval assembly according to clause 16, wherein when the second retrieval device is in the expanded rest state the proximal collar is movable distally to a third axial position on the elongate wire proximal to the distal collar and is spaced apart from the distal collar by a third distance that is less than the second distance.

Clause 18. The clot retrieval assembly according to clause 1, further comprising:
a second retrieval device located on the elongate wire proximal to the first retrieval device, the second retrieval device comprising:
a proximal collar fixed stationary on the elongate wire;
a distal collar being slideable along a portion of the length of the elongate wire; and
a plurality of shape memory elongate clot capturing elements that each has a proximal end coupled to the proximal collar of the second retrieval device and a distal end coupled to the distal collar of the second retrieval device;
the second retrieval device being configured to transition from a radially constrained state to an expanded rest state, in the radially constrained state the distal collar of the second retrieval device is located at a first axial position on the elongate wire proximal to the proximal collar of the second retrieval device and is spaced apart from the proximal collar of the second retrieval device by a first distance, in the expanded rest state the distal collar of the second retrieval device is located at a second axial position on the elongate wire distal to the proximal collar of the second retrieval device and is spaced apart from the proximal collar of the second retrieval device by a second distance that is less than the first distance.

Group C Clauses:

Clause 1. A method of making a clot retrieval assembly, the method comprising:
- obtaining a first collar having a proximal end, a distal end, a central longitudinal through opening extending between and through the proximal and distal ends, and a plurality of longitudinal channels located in the proximal end around the central longitudinal through opening, the central longitudinal through opening having a central axis;
- obtaining a second collar having a proximal end, a distal end, a central through opening extending between and through the proximal and distal ends of the second collar, and a plurality of channels located in the distal end of the second collar around the central through opening of the second collar, the central longitudinal through opening of the second collar having a central axis;
- obtaining a plurality of elongate elements that each has a proximal end, a distal end and a length;
- fixing the first end of each of the plurality of elongate elements inside a respective one of the plurality of channels in the first collar;
- fixing the second end of each of the plurality of elongate elements inside a respective one of the plurality of channels in the second collar;
- axially aligning the central axes of the central through openings of the first and second collars;
- after axially aligning the central axes of the central through openings of the first and second collars, applying an axial force to one or both of the first and second collars to cause one or both of the first and second collars to move axially towards the other so that the plurality of elongate elements invert around the second collar;
- shape-setting the plurality of elongate elements while the plurality of elongate elements are inverted around the second collar; and
- mounting the proximal and distal collars on a distal end portion of an elongate wire with the distal collar being fixed stationary on the elongate wire and the proximal collar being slideable on the elongate wire.

Clause 2. The method according to clause 1, further comprising rotating one or both of the first and second collars with respect to the other while the plurality of elongate elements invert around the second collar.

Clause 3. The method according to clause 1, further comprising rotating one or both of the first and second collars with respect to the other after the plurality of elongate elements invert around the second collar.

Clause 4. The method according to any of the preceding clauses, wherein one or both of the first and second collars is made of a radiopaque material.

Clause 5. The method according to any of the preceding clauses, wherein one or both of the first and second collars is coated with a radiopaque material.

Clause 6. The method according to any of the preceding clauses, wherein the plurality of elongate elements are made of Nitinol.

Clause 7. The method according to any of the preceding clauses, further comprising attaching to one or more of the plurality of elongate elements a permeable cover that extends circumferentially around a portion of the plurality of elongate elements.

Clause 8. The method according to any of the preceding clauses, further comprising shaping the plurality of elongate elements by use of a fixture prior to shape-setting the plurality of elongate elements.

Clause 9. The method according to any of the preceding clauses, wherein the plurality of the elongate elements comprise wires.

Clause 10. The method according to any of the preceding clauses, wherein the plurality of the elongate elements comprise ribbons.

Clause 11. The method according to clause 9, wherein some of the wires have a first diameter and some of the wires have a second diameter less than the first diameter.

Clause 12. The method according to clause 10, wherein some of the plurality of ribbons have a first width and some of the plurality of elongate elements have a second width less than the first width.

Clause 13. The method according to any of the preceding clauses, wherein the first collar has an atraumatic tip.

Clause 14. The method according to any of the preceding clauses wherein the first collar has an atraumatic tip and the second collar has an atraumatic tip.

Clause 15. The method according to any of the preceding clauses, further comprising radially constraining the retrieval device inside a sheath.

Clause 16. The method according to clause 15, wherein the retrieval device is radially constrained inside the sheath such that no portions of the shape memory elongate clot capturing elements reside proximal to the proximal collar.

Group D Clauses:

Clause 1. A method of making a clot retrieval device, the method comprising:
- obtaining a cylindrical tube having a proximal end, a distal end, a length and a central longitudinal axis, the tube having a plurality of circumferentially spaced-apart continuous elongate slots that each extends along a portion of the length of the tube, residing between each adjacent set of spaced-apart elongate slots is an elongate clot capturing element, each of the elongate slots having a proximal end and a distal end that are respectively spaced-apart from the proximal and distal ends of the tube, the tube including a proximal collar disposed between the proximal ends of the elongate slots and the proximal end of the tube, the tube including a distal collar disposed between the distal ends of the elongate slots and the distal end of the tube, each of the elongate clot capturing elements having a proximal end portion and a distal end portion;
- applying a distally directed force to the proximal collar and/or the distal collar to cause at least some of the proximal portions of the elongate clot capturing elements to invert around the proximal collar;
- shape-setting the plurality of elongate elements while the plurality of elongate elements are inverted around the proximal collar.

Clause 2. The method according to clause 1, further comprising rotating one or both of the proximal and distal collars with respect to the other while the plurality of elongate elements invert around the second collar.

Clause 3. The method according to clause 1, further comprising rotating one or both of the proximal and distal collars with respect to the other after the plurality of elongate elements invert around the second collar.

Clause 4. The method according to any of the preceding clauses, wherein one or both of the proximal and distal collars is coated with a radiopaque material.

Clause 5. The method according to any of the preceding clauses, wherein the tube is made of Nitinol.

Clause 6. The method according to any of the preceding clauses, further comprising attaching to one or more of the clot capturing elements a permeable cover that extends circumferentially around the distal end portions of elongate clot capturing elements.

Clause 7. The method according to any of the preceding clauses, further comprising shaping the plurality of elongate clot capturing elements by use of a fixture prior to shape-setting the elongate clot capturing elements.

Clause 8. The method according to any of the preceding clauses, wherein each of the elongate clot capturing elements includes an area of reduced thickness.

Clause 9. The method according to clause 8, wherein the areas of reduced thickness are configured to cause an initial buckling of the elongate clot capturing elements in the areas of reduced thickness when the distally directed force is applied to the proximal collar and/or the proximally directed force is applied to the distal collar.

Clause 10. The method according to any of the preceding clauses, wherein the proximal end portions of the elongate clot capturing elements have a first width and the distal end portions of the elongate clot capturing elements have a second width different than the first width.

Clause 11. The method according to clause 10, wherein the second width is greater than the first width.

Clause 12. The method according to any of the preceding clauses, wherein prior to the distally directed force be applied to the proximal collar and/or the proximally directed force being applied to the distal collar, the proximal end portions of the elongate clot capturing elements curve about the longitudinal axis of the tube.

Clause 13. The method according to any of the preceding clauses, wherein the proximal end portions of the elongate clot capturing elements are arranged helical with respect to the longitudinal axis of the tube.

Clause 14. The method according to any of the preceding clauses, wherein the distal end portions of the elongate clot capturing elements are straight.

Clause 15. The method according to clause 14, wherein the straight distal end portions of the elongate clot capturing elements are arranged parallel to the longitudinal axis of the tube.

Clause 16. The method according to clause 12, wherein the distal end portions of the elongate clot capturing elements are curved.

Clause 17. The method according to clause 12, wherein the proximal end portions of the elongate capturing elements have a first length and the distal end portions of the elongate capturing elements have a second length shorter than the first length.

Clause 18. The method according to clause 1, wherein each of the elongate clot capturing elements includes an area of reduced width.

Clause 19. The method according to clause 18, wherein the areas of reduced width are configured to cause an initial buckling of the elongate clot capturing elements in the areas of reduced width when the distally directed force is applied to the proximal collar and/or the proximally directed force is applied to the distal collar.

Clause 20. The method according to clause 1, wherein the elongate clot capturing elements include an intermediate portion located between the proximal and distal end portions, the proximal and distal end portions of the elongate capturing elements being arranged circumferentially offset from one another and being joined by the intermediate portion.

Clause 21. The method according to clause 1, wherein prior to the distally directed force be applied to the proximal collar and/or the proximally directed force being applied to the distal collar, each of the circumferentially spaced-apart continuous elongate slots has a length that is greater than or equal to 70% the length of the cylindrical tube.

Group E Clauses:

Clause 1. A method of making a clot retrieval device, the method comprising:
  obtaining a cylindrical tube having a proximal end, a distal end, a length and a central longitudinal axis, the tube having a plurality of circumferentially spaced-apart continuous elongate slots that each extends along a portion of the length of the tube, residing between each adjacent set of spaced-apart elongate slots is an elongate clot capturing element, each of the elongate slots having a proximal end and a distal end that are respectively spaced-apart from the proximal and distal ends of the tube, the tube including a proximal collar disposed between the proximal ends of the elongate slots and the proximal end of the tube, the tube including a distal collar disposed between the distal ends of the elongate slots and the distal end of the tube, each of the elongate clot capturing elements having a proximal end portion and a distal end portion;
  applying a distally directed force to the proximal collar and/or the distal collar to cause at least some of the proximal portions of the elongate clot capturing elements to invert around the proximal collar;
  shape-setting the plurality of elongate elements while the plurality of elongate elements are inverted around the proximal collar; and
  mounting the proximal and distal collars on a distal end portion of an elongate wire with the distal collar being fixed stationary on the elongate wire and the proximal collar being slideable on the elongate wire.

Clause 2. The method according to clause 1, further comprising rotating one or both of the proximal and distal collars with respect to the other while the plurality of elongate clot capturing elements invert around the second collar.

Clause 3. The method according to clause 1, further comprising rotating one or both of the proximal and distal collars with respect to the other after the plurality of elongate clot capturing elements invert around the second collar and prior to shape-setting the plurality of elongate clot capturing elements.

Clause 4. The method according to any of the preceding clauses, wherein one or both of the proximal and distal collars is coated with a radiopaque material.

Clause 5. The method according to any of the preceding clauses, wherein the tube is made of Nitinol.

Clause 6. The method according to any of the preceding clauses, further comprising attaching to one or more of the elongate clot capturing elements a permeable cover that extends circumferentially around the distal end portions of elongate clot capturing elements.

Clause 7. The method according to any of the preceding clauses, further comprising shaping the plurality of elongate clot capturing elements by use of a fixture prior to shape-setting the elongate clot capturing elements.

Clause 8. The method according to any of the preceding clauses, wherein each of the elongate clot capturing elements includes an area of reduced thickness.

Clause 9. The method according to clause 8, wherein the areas of reduced thickness are configured to cause an initial buckling of the elongate clot capturing elements in the areas of reduced thickness when the distally directed force is applied to the proximal collar and/or the proximally directed force is applied to the distal collar.

Clause 10. The method according to clause 1, wherein the proximal end portions of the elongate clot capturing elements have a first width and the distal end portions of the elongate clot capturing elements have a second width different first width.

Clause 11. The method according to clause 10, wherein the second width is greater than the first width.

Clause 12. The method according to any of the preceding clauses, wherein prior to the distally directed force be applied to the proximal collar and/or the proximally directed force being applied to the distal collar, the proximal end portions of the elongate clot capturing elements curve about the longitudinal axis of the tube.

Clause 13. The method according to any of the preceding clauses, wherein the proximal end portions of the elongate clot capturing elements are arranged helical with respect to the longitudinal axis of the tube.

Clause 14. The method according to clause 12, wherein the distal end portions of the elongate clot capturing elements are straight.

Clause 15. The method according to clause 14, wherein the straight distal end portions of the elongate clot capturing elements are arranged parallel to the longitudinal axis of the tube.

Clause 16. The method according to clause 12, wherein the distal end portions of the elongate clot capturing elements are curved.

Clause 17. The method according to clause 12, wherein the proximal end portions of the elongate capturing elements have a first length and the distal end portions of the elongate capturing elements have a second length shorter than the first length.

Clause 18. The method according to any of the preceding clauses, wherein each of the elongate clot capturing elements includes an area of reduced width.

Clause 19. The method according to clause 18, wherein the areas of reduced width are configured to cause an initial buckling of the elongate clot capturing elements in the areas of reduced width when the distally directed force is applied to the proximal collar and/or the proximally directed force is applied to the distal collar.

Clause 20. The method according to clause 1, wherein the elongate clot capturing elements include an intermediate portion located between the proximal and distal end portions, the proximal and distal end portions of the elongate capturing elements being arranged circumferentially offset from one another and being joined by the intermediate portion.

Clause 21. The method according to clause 1, wherein prior to the distally directed force be applied to the proximal collar and/or the proximally directed force being applied to the distal collar, each of the circumferentially spaced-apart continuous elongate slots has a length that is greater than or equal to 70% the length of the cylindrical tube.

What is claimed is:

1. A clot retrieval assembly comprising:
an elongate wire having a length and a longitudinal axis;
a first retrieval device comprising:
  a distal collar fixed stationary on the elongate wire;
  a proximal collar being slideable along a portion of the length of the elongate wire;
  a plurality of shape memory elongate clot capturing elements that each has a proximal end coupled to the proximal collar and a distal end coupled to the distal collar, each of the plurality of shape memory elongate clot capturing elements having a proximal end portion and a distal end portion, the plurality of the shape memory elongate clot capturing elements and the proximal and distal collars being formed from a single piece of material; and
  the first retrieval device being configured to automatically transition from a radially constrained state to a radially unconstrained expanded rest state, in the radially constrained state no portion of the plurality of shape memory elongate clot capturing elements is located proximal to the proximal collar and the proximal collar is located at a first axial position on the elongate wire proximal to the distal collar and is spaced apart from the distal collar by a first distance, in the radially unconstrained expanded rest state the proximal collar is located at a second axial position on the elongate wire proximal to the distal collar and is spaced apart from the distal collar by a second distance that is less than the first distance and at least some of the plurality of shape memory elongate clot capturing elements are inverted around the proximal collar with at least a part of some of the plurality of shape memory elongate clot capturing elements being disposed over the proximal collar; and
a second retrieval device located on the elongate wire distal to the first retrieval device, the second retrieval device comprising:
  a distal collar fixed stationary on the elongate wire;
  a proximal collar being slideable along a portion of the length of the elongate wire; and
  a plurality of shape memory elongate capturing elements that each has a proximal end coupled to the proximal collar of the second retrieval device and a distal end coupled to the distal collar of the second retrieval device;
  the second retrieval device being configured to transition from a radially constrained state to an expanded rest state, in the radially constrained state the proximal collar of the second retrieval device is located at a fourth axial position on the elongate wire proximal to the distal collar of the second retrieval device and is spaced apart from the distal collar of the second retrieval device by a fourth distance, in the expanded rest state the proximal collar of the second retrieval device is located at a fifth axial position on the elongate wire proximal to the distal collar of the second retrieval device and is spaced apart from the distal collar of the second retrieval device by a fifth distance that is less than the fourth distance.

2. The clot retrieval assembly according to claim 1, wherein when the first retrieval device is in the radially unconstrained expanded rest state the proximal collar of the first retrieval device is movable distally to a third axial position on the elongate wire proximal to the distal collar and is spaced apart from the distal collar of the first retrieval device by a third distance that is less than the second distance.

3. The clot retrieval assembly according to claim 2, wherein when the proximal collar of the first retrieval device is in the third axial position on the elongate wire, the first retrieval device is in an expanded stressed state.

4. The clot retrieval assembly according to claim 1, wherein when the first retrieval device is in the radially constrained state no portion of each of the plurality of shape memory elongate clot capturing elements of the first retrieval device bends back on itself.

5. The clot retrieval assembly according to claim 1, wherein when the first retrieval device is in the radially unconstrained expanded rest state at least some of the plurality of shape memory elongate clot capturing elements of the first retrieval device take a zigzag path from the proximal collar of the first retrieval device to the distal collar of the first retrieval device with a first portion of the path extending in a proximal direction and a second portion of the path extending in a distal direction.

6. The clot retrieval assembly according to claim 1, wherein the distal collar of the first retrieval device has an atraumatic distal tip.

7. The clot retrieval assembly according to claim 1, wherein when the proximal collar of the first retrieval device is in the second axial position no portion of the proximal collar of the first retrieval device touches the distal end portions of the plurality of shape memory elongate clot capturing elements of the first retrieval device.

8. The assembly according to claim 1, wherein when the second retrieval device is in the expanded rest state the proximal collar of the second retrieval device is movable distally to a sixth axial position on the elongate wire proximal to the distal collar of the second retrieval device and is spaced apart from the distal collar of the second retrieval device by a sixth distance that is less than the fifth distance.

9. The assembly according to claim 1, wherein the first retrieval device comprises a plurality of circumferential spaced-apart slots separated by the plurality of shape memory elongate capturing elements.

10. The assembly according to claim 1, wherein a thickness of one or more of the plurality of shape memory elongate capturing elements of the first retrieval device differs along a length of the one or more of the plurality of shape memory elongate capturing elements of the first retrieval device.

11. The assembly according to claim 1, wherein a width of one or more of the plurality of shape memory elongate capturing elements of the first retrieval device differs along a length of the one or more of the plurality of shape memory elongate capturing elements of the first retrieval device.

* * * * *